(12) United States Patent
Jacobs et al.

(10) Patent No.: US 6,852,752 B2
(45) Date of Patent: Feb. 8, 2005

(54) UREA COMPOUNDS, COMPOSITIONS AND METHODS OF USE AND PREPARATION

(75) Inventors: Jeffrey W. Jacobs, San Mateo, CA (US); Dinesh Patel, Fremont, CA (US); Jason Lewis, Hayward, CA (US); Zhi-Jie Ni, Fremont, CA (US)

(73) Assignee: Vicuron Pharmaceuticals Inc., Fremont, CA (US)

( * ) Notice: Subject to any disclaimer, the term of this patent is extended or adjusted under 35 U.S.C. 154(b) by 16 days.

(21) Appl. No.: 09/738,376

(22) Filed: Dec. 13, 2000

(65) Prior Publication Data

US 2002/0119962 A1 Aug. 29, 2002

Related U.S. Application Data

(60) Provisional application No. 60/266,329, filed on Dec. 17, 1999.

(51) Int. Cl.[7] .................... A61K 31/40; C07D 285/12; C07D 277/04; C07D 207/00; C07D 409/02

(52) U.S. Cl. .................. 514/422; 514/423; 548/139; 548/195; 548/518; 548/519; 548/527; 548/538

(58) Field of Search ................................. 548/538, 527, 548/518, 519, 195, 139; 514/422, 423

(56) References Cited

FOREIGN PATENT DOCUMENTS

JP  56-97266  *  8/1981

OTHER PUBLICATIONS

Hemmi et al. (WO 97/47599), 1997. Abstract.*

* cited by examiner

*Primary Examiner*—Bruck Kifle
(74) *Attorney, Agent, or Firm*—Morrison & Foerster LLP

(57) ABSTRACT

Novel hydroxamic acid compounds are disclosed. These hydroxamates inhibit peptide deformylase (PDF), an enzyme present in prokaryotes and are therefore useful as antimicrobials and antibiotics. Methods of synthesis and of use of the compounds are also disclosed.

26 Claims, No Drawings

UREA COMPOUNDS, COMPOSITIONS AND METHODS OF USE AND PREPARATION

CROSS-REFERENCE TO RELATED APPLICATIONS

The application claims priority under 35 U.S.C. 119(e) to U.S. Provisional Application Serial No. 60/266,329, which was converted pursuant to 37 C.F.R. §1.53(b)(2)(ii) from U.S. patent application Ser. No. 09/466,402, filed on Dec. 17, 1999, the disclosure of which is incorporated herein in its entirety.

BACKGROUND OF THE INVENTION

1. Field of the Invention

This invention is directed to novel urea compounds. This invention is also directed to uses of these compounds in various medicinal applications, including treating disorders amenable to treatment by peptide deformylase inhibitors. This invention is still further directed to pharmaceutical compounds comprising these compounds and methods of synthesis thereof.

2. State of the Art

Treatment of microbial infection in host organisms requires an effective means to kill the microbe while doing as little harm to the host as possible. Accordingly, agents which target characteristics unique to a pathology-causing microorganism are desirable for treatment. Penicillin is an extremely well known example of such an agent. Penicillin acts by inhibiting biosynthesis of bacterial cell walls. Since mammalian cells do not require cell walls for survival, administration of penicillin to a human infected with bacteria can kill the bacteria without affecting human cells.

However, the use of antibiotics and antimicrobials has also resulted in increased resistance to these agents. As bacteria become resistant to older, more widely used antimicrobial agents, new antimicrobials must be developed in order to provide effective treatments for human and non-human animals suffering from microbial infection.

Peptide deformylase is a metallopeptidase found in prokaryotic organisms such as bacteria. Protein synthesis in prokaryotic organisms begins with N-formyl methionine (fMet). After initiation of protein synthesis, the formyl group is removed by the enzyme peptide deformylase (PDF); this activity is essential for maturation of proteins. It has been shown that PDF is required for bacterial growth (Chang et al. *J. Bacteriol.* 171:4071–4072 (1989); Meinnel T, Blanquet S, *J. Bacteriol.* 176(23):7387–90 (1994); Mazel D et al., *EMBO J.* 13(4):914–23 (1994)). Since protein synthesis in eukaryotic organisms does not depend on fMet for initiation, agents that will inhibit PDF are attractive candidates for development of new antimicrobial and antibacterial drugs. Prokaryotic organisms, including disease-causing prokaryotes, are described in Balows, A., H. G. Truper, M. Dworkin, W. Harder, and K.-H. Schleifer (eds.), *The Prokaryotes*, 2nd ed., New York: Springer-Verlag, 1992; and Holt, J. G. (editor-in-chief). *Bergey's Manual of Systematic Bacteriology*, Vols. 1–4, Baltimore: Williams & Wilkins, 1982, 1986, 1989.

PDF is part of the metalloproteinase superfamily. While PDF clearly shares many of the features which characterize metalloproteinases, it differs from other members of the superfamily in several important respects. First, the metal ion in the active enzyme appears to be Fe (II), or possibly another divalent cationic metal, instead of the zinc ion more commonly encountered. Rajagopalan et al., *J. Am. Chem. Soc.*, 119:12418–19 (1997). Second, the divalent ion appears to play an important role, not only in catalysis, but also in the structural integrity of the protein. Third, the third ligand of the divalent ion is a cysteine, rather than a histidine or a glutamate, as in other metalloproteinases and is not located at the C-terminal side of the HEXXH motif but far away along the amino acid sequence and N-terminal to the motif. Finally, the solution structure shows significant differences in the secondary and tertiary structure of PDF compared to other prototypical metalloproteinases see Meinnel et al. *J. Mol. Biol.* 262:375–386 (1996). PDF from *E. coli*, *Bacillus stearothermophilus*, and *Thermus thermophilus* have been characterized see Meinnel et al., *J. Mol. Biol.* 267:749–761 (1997). The enzyme studied by Meinnel et al. contained a zinc ion as the divalent ion and the structural features summarized above were obtained from zinc-containing proteins. The structure of the protein has also been determined by NMR (see O'Connell et al., *J. Biomol. NMR* 13(4): 311–24 (1999)).

Metalloproteinases are critical to many aspects of normal metabolism. The class known as matrix metalloproteinases (MMPs) are involved in tissue remodeling, such as degradation of the extracellular matrix. These enzymes are believed to play a role in normal or beneficial biological events such as the formation of the corpus luteum during pregnancy (see Liu et al., *Endocrinology* 140(11):5330–8 (1999)), wound healing (Yamagiwa et al., *Bone* 25(2): 197–203 (1999)), and bone growth in healthy children (Bord et al., *Bone* 23(1):7–12 (1998)). Disorders involving metalloproteinases have been implicated in several diseases such as cancer, arthritis, and autoimmune diseases.

Because of the importance of MMPs in normal physiological processes, it would be preferable to develop agents that inhibit PDF, a metalloproteinase present only in prokaryotes, while avoiding significant inhibition of MMPs. Alternatively, PDF inhibitors which also inhibit MMPs can be of use where the therapeutic benefits of inhibiting PDF outweigh the risk of side effects from MMP inhibition.

A wide variety of compounds have been developed as candidate inhibitors of MMPs and other metalloproteinases, and much effort has also been directed at synthetic methods for these compounds and related compounds. See Izquierdo-Martin et al. (1992) *J. Am. Chem. Soc.* 114:325–331; Cushman et al. (1981) Chapter 5 "*Specific Inhibitors of Zinc Metallopeptidases*" in *Topics in Molecular Pharmacology* (Burgen & Roberts, eds.); Mohler et al. *Nature* 370:218–220 (1994); Gearing et al., *Nature* 370:555–557 (1994); McGeehan et al., *Nature* 370:558–561 (1994); U.S. Pat. Nos. 4,052,511, 4,303,662, 4,311,705, 4,321,383, 4,599,361, 4,804,676, 5,128,346, 5,256,657, 5,268,384, 5,447,929, 5,453,423, 5,552,419, 5,614,625, 5,643,908, 5,712,300, and 5,869,518; European patent publications EP 236872, EP 274453, EP 334244, EP 423943, EP 489577, EP 489579, EP 497192, EP 574758; and International PCT Patent Applications Publication Nos. WO 90/05716, WO 90/05719, WO 91/02716, WO 92/13831, WO 92/22523, WO 93/09090, WO 93/09097, WO 93/20047, WO 93/24449, WO 93/24475, WO 94/02446, WO 94/02447, WO 94/21612, WO 94/25434, WO 94/25435, WO 95/33731, WO 96/25156, WO 96/26918 WO 97/30707, WO 97/49674, WO 98/55449, and WO 99/02510.

Research on inhibitors of PDF is much less extensive than that for inhibitors of MMPs. N-formyl hydroxylamine derivatives are described in International Patent Application WO 99/39704. Peptide aldehyde inhibitors of PDFs are described in Durand et al., *Arch. Biochem. Biophys.*, 367(2): 297–302 (1999). The PDF inhibitor (S)-2-O-(H- phosphonoxy)-L-caproyl-L-leucyl-p-nitroanilide is described in Hao et al., *Biochemistry* 38:4712–4719 (1999), and peptidyl H-phosphonate inhibitors of PDF are discussed in Hu et al., *Bioorg. Med. Chem. Lett.* 8:2479–2482 (1998). Formylated peptides and pseudopeptides are described in Meinnel et al., *Biochemistry* 38(14):4288–4295 (1999) as inhibitors of PDF.

In view of the importance of identifying new antibiotics to treat bacteria resistant to existing antibiotics, and the relatively small amount of work that has been carried out on PDF inhibitors, it is desirable to develop novel inhibitors of PDF for evaluation and use as antibacterial and antimicrobial agents. The present invention fulfills this need.

SUMMARY OF THE INVENTION

In one aspect, this invention is directed to a compound of Formula (I):

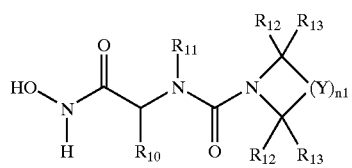

(I)

wherein:

$R_{10}$ is selected from the group consisting of hydrogen, $R_{14}$, $R_{15}OH$, and $R_{15}$—O—$R_{16}$, where $R_{14}$ and $R_{16}$ are independently selected from the group consisting of —($C_1$–$C_{12}$) alkyl, substituted alkyl, or heteroalkyl, —($C_1$–$C_{12}$) alkenyl, substituted alkenyl, or heteroalkenyl, —($C_1$–$C_{12}$) alkynyl, substituted alkynyl, or heteroalkynyl, or —($C_0$–$C_8$) alkylene or substituted alkylene)-($C_3$–$C_{12}$) arylene or heteroarylene)-($C_0$–$C_8$ alkyl or substituted alkyl); and $R_{15}$ is selected from the group consisting of —($C_1$–$C_{12}$) alkylene, substituted alkylene, or heteroalkylene, —($C_1$–$C_{12}$) alkenylene, substituted alkenylene, or heteroalkenylene, —($C_1$–$C_{12}$) alkynylene, substituted alkynylene, or heteroalkynylene, or —($C_0$–$C_8$) alkylene or substituted alkylene)-($C_3$–$C_{12}$) arylene or heteroarylene)-($C_0$–$C_8$ alkylene or substituted alkylene);

$R_{11}$ is selected from the group consisting of hydrogen, —($C_1$–$C_{12}$) alkyl, substituted alkyl, or heteroalkyl, —($C_1$–$C_{12}$) alkenyl, substituted alkenyl, or heteroalkenyl, —($C_1$–$C_{12}$) alkynyl, substituted alkynyl, or heteroalkynyl, or —($C_0$–$C_{12}$) alkylene or substituted alkylene)-($C_3$–$C_{12}$) arylene or heteroarylene)-($C_0$–$C_{12}$ alky or substituted alkyl);

$n_1$ is an integer from 1 to 5;

zero or one Y is selected from the group consisting of —O—, —$NR_{17}$—, and —S—, and all remaining Y are —$CR_{12}R_{13}$—; where $R_{12}$ and $R_{13}$ are each independently hydrogen, $R_{17}$, —OH, —$OR_{17}$, —SH, —$SR_{17}$, —$NH_2$, —$NHR_{17}$, —$NR_{17}R_{18}$, —C(=O)$R_{17}$, —C(=O)$NR_{17}R_{18}$, —C(=O)$OR_{17}$, —C(=O)$SR_{17}$, —C(=O)$CR_{17}R_{18}R_{19}$, —C(=O)$OCR_{17}R_{18}R_{19}$, —S(=O)$_2NR_{17}R_{18}$, —N($R_{17}$)C(=O)$R_{18}$, —N($R_{17}$)C(=O)$OR_{18}$, —N($R_{17}$)S(=O)$_2R_{18}$, or —N($R_{17}$)S(=O)$_2$ $OR_{18}$, or where two vicinal $R_{12}$ or $R_{13}$ groups combine to form a substituted or unsubstituted —($C_4$–$C_{10}$) cyclic alkyl, cyclic heteroalkyl, aryl or heteroaryl group; where $R_{17}$, $R_{18}$ and $R_{19}$ are each independently hydrogen, —($C_1$–$C_{12}$) alkyl, substituted alkyl, or heteroalkyl, —($C_1$–$C_{12}$) alkenyl, substituted alkenyl, or heteroalkenyl, —($C_1$–$C_{12}$) alkynyl, substituted alkynyl, or heteroalkynyl, alkoxy, or —($C_0$–$C_8$ alkylene or substituted alkylene)-($C_3$–$C_{12}$ arylene or heteroarylene)-($C_0$–$C_8$ alkyl or substituted alkyl), or where, when two or three of $R_{17}$, $R_{18}$ and $R_{19}$ are attached to the same atom, two or three of $R_{17}$, $R_{18}$ and $R_{19}$ can combine to form a substituted or unsubstituted —($C_4$–$C_{10}$) cyclic alkyl, cyclic heteroalkyl, aryl or heteroaryl group; or a pharmaceutically acceptable salt thereof.

Preferably the compound of Formula (I) inhibits peptide deformylase at an $IC_{50}$ of less than or equal to about 100 nm, preferably of less than or equal to 10 nm, more preferably of less than or equal to 1 nm.

Preferably the compound of Formula (I) displays a selectivity for peptide deformylase over at least one metalloproteinase selected from the group consisting of ACE and Matrilysin of greater than or equal to about 10 times, more preferably of greater than or equal to about 100 times, still more preferably of greater than or equal to about 1000 times.

In a second aspect, this invention is directed to pharmaceutical compositions comprising a therapeutically effective amount of a compound of Formula (I) or a pharmaceutically acceptable salt thereof and a pharmaceutically acceptable excipient.

In a third aspect, this invention is directed to a method of treatment of a disease in a mammal treatable by administration of a peptide deformylase inhibitor which method comprises administration of a therapeutically effective amount of a pharmaceutical composition comprising a therapeutically effective amount of a compound of Formula (I) or a pharmaceutically acceptable salt thereof and a pharmaceutically acceptable excipient either alone or in combination with other pharmacologically active agents. In particular, the compounds of this invention are useful in treating microbial diseases. The microbial infection can be due to bacteria, other prokaryotes, or other organisms, including parasites, dependent on peptide deformylase for growth or survival.

In a fourth aspect, this invention is directed to the use of a compound of Formula (I) or a pharmaceutically acceptable salts thereof in the preparation of a medicament for use in the treatment of diseases mediated by peptide deformylase enzyme.

In a fifth aspect, this invention is directed to a method for identifying compounds useful in treating microbial infections, comprising performing an assay to identify compounds which meet the criterion of either i) an $IC_{50}$ for peptide deformylase of less than or equal to about 1 µM, or ii) an MIC for a disease-causing pathogen of less than or equal to about 32 µg/ml; performing an assay to identify compounds which meet the criterion of iii) displaying a selectivity for peptide deformylase over at least one metalloproteinase selected from the group consisting of Angiotensin Converting Enzyme (ACE) and Matrilysin of greater than or equal to about 10 times; and selecting compounds which meet either both criteria i) and iii), or both criteria ii) and iii). More preferably, the compounds so identified meet the criterion of either i) an $IC_{50}$ for peptide deformylase of less than or equal to about 100 nM, or ii) an MIC for a disease-causing pathogen of less than or equal to about 10 µg/ml.

DETAILED DESCRIPTION OF THE INVENTION

Unless otherwise stated, the following terms as used in the specification have the following meaning.

The term "alkyl" refers to saturated aliphatic groups including straight-chain, branched-chain, cyclic groups, and combinations thereof, having the number of carbon atoms specified, or if no number is specified, having 1 to 12 carbon atoms. Examples of alkyl groups include, but are not limited to, groups such as methyl, ethyl, n-propyl, isopropyl, n-butyl, isobutyl, sec-butyl, t-butyl, n-pentyl, neopentyl, cyclopropyl, cyclobutyl, cyclopentyl, cyclohexyl, cyclobutylmethyl, cyclobutylethyl, cyclopentylmethyl, cyclopentylethyl, and adamantyl. Cyclic groups can consist of one ring, including, but not limited to, groups such as cycloheptyl, or multiple fused rings, including, but not limited to, groups such as adamantyl or norbornyl.

The term "alkylene" means a saturated divalent aliphatic groups including straight-chain, branched-chain, cyclic groups, and combinations thereof, having the number of carbon atoms specified, or if no number is specified, having 1 to 12 carbon atoms, e.g., methylene, ethylene, 2,2-dimethylethylene, propylene, 2-methylpropylene, butylene, pentylene, and the like.

The term "substituted alkyl" means an alkyl group as defined above that is substituted with one or more substituents, preferably one to three substituents, selected from the group consisting of halogen (fluoro, chloro, bromo, and iodo, preferably fluoro, chloro, or bromo), alkoxy, acyloxy, amino, mono or dialkylamino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. The phenyl group may optionally be substituted with one to three substituents selected from the group consisting of halogen (fluoro, chloro, bromo, and iodo, preferably fluoro, chloro, or bromo), alkoxy, acyloxy, amino, mono or dialkylamino, hydroxyl, mercapto, carboxy, benzyloxy, benzyl, cyano, nitro, thioalkoxy, carboxaldehyde, carboalkoxy and carboxamide. Examples of substituted alkyl groups include, but are not limited to, —CF$_3$, —CF$_2$—CF$_3$, hydroxymethyl, 1- or 2-hydroxyethyl, methoxymethyl, 1- or 2-ethoxyethyl, carboxymethyl, 1- or 2-carboxyethyl, benzyl, and the like.

The term "substituted alkylene" means an alkylene group as defined above that is substituted with one or more substituents, preferably one to three substituents, selected from the group consisting of halogen (fluoro, chloro, bromo, and iodo, preferably fluoro, chloro, or bromo), alkoxy, acyloxy, amino, mono or dialkylamino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. The phenyl group may optionally be substituted with one to three substituents selected from the group consisting of halogen (fluoro, chloro, bromo, and iodo, preferably fluoro, chloro, or bromo), alkoxy, acyloxy, amino, mono or dialkylamino, hydroxyl, mercapto, carboxy, benzyloxy, benzyl, cyano, nitro, thioalkoxy, carboxaldehyde, carboalkoxy and carboxamide. Examples of substituted alkyl groups include, but are not limited to, —CF$_2$—, —CF$_2$—CF$_2$—, hydroxymethylene, 1- or 2-hydroxyethylene, methoxymethylene, 1- or 2-ethoxyethylene, carboxymethylene, 1- or 2-carboxyethylene, and the like.

The term "alkenyl" refers to unsaturated aliphatic groups including straight-chain, branched-chain, cyclic groups, and combinations thereof, having the number of carbon atoms specified, or if no number is specified, having 1 to 12 carbon atoms, which contain at least one double bond (—C═C—). Examples of alkenyl groups include, but are not limited to, allyl vinyl, —CH$_2$—CH═CH—CH$_3$, —CH$_2$—CH$_2$-cyclopentenyl and —CH$_2$—CH$_2$-cyclohexenyl where the ethyl group can be attached to the cyclopentenyl, cyclohexenyl moiety at any available carbon valence.

The term "alkenylene" refers to unsaturated divalent aliphatic groups including straight-chain, branched-chain, cyclic groups, and combinations thereof, having the number of carbon atoms specified, or if no number is specified, having 1 to 12 carbon atoms, which contain at least one double bond (—C═C—). Examples of alkenyl groups include, but are not limited to, —CH═CH—, —CH$_2$—CH═CH—CH$_2$—, —CH$_2$—CH(cyclopentenyl)- and the like.

The term "alkynyl" refers to unsaturated aliphatic groups including straight-chain, branched-chain, cyclic groups, and combinations thereof, having the number of carbon atoms specified, or if no number is specified, having 1 to 12 carbon atoms, which contain at least one triple bond (—C≡C—). Examples of alkenyl groups include, but are not limited to, acetylene, 2-butynyl, and the like.

The term "alkynylene" refers to unsaturated divalent aliphatic groups including straight-chain, branched-chain, cyclic groups, and combinations thereof, having the number of carbon atoms specified, or if no number is specified, having 1 to 12 carbon atoms, which contain at least one triple bond (—C≡C—). Examples of alkenyl groups include, but are not limited to, —C≡C—, —C≡C—CH$_2$—, and the like.

The term "substituted alkenyl" or "substituted alkynyl," refers to the alkenyl and alkynyl groups as defined above that are substituted with one or more substituents, selected from the group consisting of halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. Examples of substituted alkyl groups include, but are not limited to, —CH═CF$_2$, hydroxyethenyl, methoxypropenyl, and the like.

The term "substituted alkenylene" or "substituted alkynylene," refers to the alkenylene and alkynylene groups as defined above that are substituted with one or more substituents, selected from the group consisting of halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group.

The term "aryl" or "Ar" refers to an aromatic carbocyclic group of 6 to 14 carbon atoms having a single ring (including, but not limited to, groups such as phenyl) or multiple condensed rings (including, but not limited to, groups such as naphthyl or anthryl), and includes both unsubstituted and substituted aryl groups. Substituted aryl is an aryl group that is substituted with one or more substituents, preferably one to three substituents selected from the group consisting of alkyl, alkenyl, alkynyl, halogen, alkoxy, acyloxy, amino, mono or dialkylamino, hydroxyl, mercapto, carboxy, benzyloxy, phenyl, aryloxy, benzyl, cyano, nitro, thioalkoxy, carboxaldehyde, carboalkoxy and carboxamide, or a functionality that can be suitably blocked, if necessary for purposes of the invention, with a protecting group.

The term "arylene" refers to the diradical derived from aryl (including substituted aryl) as defined above and is exemplified by 1,2-phenylene, 1,3-phenylene, 1,4-phenylene, 1,2-naphthylene and the like.

The term "amino" refers to the group —NH$_2$.

The term "thioalkoxy" means a radical —SR where R is an alkyl as defined above e.g., methylthio, ethylthio, propylthio, butylthio, and the like.

The term "mono and "dialkylamino" means a radical —NHR and —NRR' respectively where R and R' independently represent an alkyl group as defined herein. Representative examples include, but are not limited to dimethylamino, methylethylamino, di(1-methylethyl)amino, (cyclohexyl)(methyl)amino, (cyclohexyl)(ethyl)amino, (cyclohexyl)(propyl)amino, (cyclohexylmethyl)(methyl)amino, (cyclohexylmethyl)(ethyl)amino, and the like.

The term "acyloxy" means a radical —OC(O)R, where R is hydrogen, alkyl, aryl, heteroaryl or substituted alkyl wherein alkyl, aryl, heteroaryl, and substituted alkyl are as defined herein. Representative examples include, but are not limited to formyl, acetyloxy, cylcohexylcarbonyloxy, cyclohexylmethylcarbonyloxy, benzoyloxy, benzylcarbonyloxy, and the like.

The term "heteroalkyl," "heteroalkenyl," and "heteroalkynyl" refers to alkyl, alkenyl, and alkynyl groups respectively as defined above, that contain the number of carbon atoms specified (or if no number is specified, having 1 to 12 carbon atoms) which contain one or more heteroatoms, preferably one to three heteroatoms, as part of the main, branched, or cyclic chains in the group. Heteroatoms are independently selected from the group consisting of —NR— where R is hydrogen or alkyl, —S—, —O—, and —P—; preferably —NR— where R is hydrogen or alkyl and/or —O—. Heteroalkyl, heteroalkenyl, and heteroalkynyl groups may be attached to the remainder of the molecule either at a heteroatom (if a valence is available) or at a carbon atom. Examples of heteroalkyl groups include, but are not limited to, groups such as —O—$CH_3$, —$CH_2$—O—$CH_3$, —$CH_2$—$CH_2$—O—$CH_3$, —S—$CH_2$—$CH_2$—$CH_3$, —$CH_2$—$CH(CH_3)$—S—$CH_3$, —$CH_2$—$CH_2$—NH—$CH_2$—$CH_3$, 1-ethyl-6-proplypiperidino, 2-ethylthiophenyl, piperazino, pyrrolidino, piperidino, and morpholino. Examples of heteroalkenyl groups include, but are not limited to, groups such as —CH=CH—NH—$CH(CH_3)$—$CH_3$.

The term "carboxaldehyde" means —CHO.

The term "carboalkoxy" means —C(O)OR where R is alkyl as defined above and include groups such as methoxycarbonyl, ethoxycarbonyl, and the like.

The term "carboxamide" means —C(O)NHR where R is alkyl as defined above.

The term "heteroaryl" or "HetAr" refers to an aromatic carbocyclic group of 3 to 9 ring atoms forming a single ring and having at least one hetero atom, preferably one to three heteroatoms including, but not limited to, heteroatoms such as N, O, P, or S, within the ring. Representative examples include, but are not limited to single ring such as imidazolyl, pyrazolyl, pyrazinyl, pyridazinyl, pyrimidinly, pyrrolyl, pyridyl, thiophene, and the like, or multiple condensed rings such as indolyl, quinoline, quinazoline, benzimidazolyl, indolizinyl, benzothienyl, and the like.

The heteroalkyl, heteroalkenyl, heteroalkynyl and heteroaryl groups can be unsubstituted or substituted with one or more substituents, preferably one to three substituents, selected from the group consisting of alkyl, alkenyl, alkynyl, benzyl, halogen, alkoxy, acyloxy, amino, mono or dialkylamino, hydroxyl, mercapto, carboxy, benzyloxy, phenyl, aryloxy, cyano, nitro, thioalkoxy, carboxaldehyde, carboalkoxy and carboxamide, or a functionality that can be suitably blocked, if necessary for purposes of the invention, with a protecting group. Examples of such substituted heteroalkyl groups include, but are not limited to, piperazine, pyrrolidine, morpholine, or piperidine, substituted at a nitrogen or carbon by a phenyl or benzyl group, and attached to the remainder of the molecule by any available valence on a carbon or nitrogen, —NH—$SO_2$-phenyl, —NH—(C=O)O-alkyl, —NH—(C=O)O-alkyl-aryl, and the like. The heteroatom(s) as well as the carbon atoms of the group can be substituted. The heteroatom(s) can also be in oxidized form.

The term "heteroarylene" refers to the diradical group derived from heteroaryl (including substituted heteroaryl), as defined above, and is exemplified by the groups 2,6-pyridylene, 2,4-pyridinylene, 1,2-quinolinylene, 1,8-quinolinylene, 1,4-benzofuranylene, 2,5-pyridnylene, 2,5-indolenyl, and the like.

The term "heteroalkylene", "heteroalkenylene", and "heteroalkynylene" refers to the diradical group derived from heteroalkyl, heteroalkenyl, and heteroalkynyl (including substituted heteroalkyl, heteroalkenyl, and heteroalkynyl), as defined above.

The term "alkylaryl" refers to an alkyl group having the number of carbon atoms designated, appended to one, two, or three aryl groups.

The term "alkoxy" as used herein refers to an alkyl, alkenyl, or alkynyl linked to an oxygen atom and having the number of carbon atoms specified, or if no number is specified, having 1 to 12 carbon atoms. Examples of alkoxy groups include, but are not limited to, groups such as methoxy, ethoxy, tert-butoxy, and allyloxy.

The term "aryloxy" as used herein refers to an aryl group linked to an oxygen atom at one of the ring carbons. Examples of alkoxy groups include, but are not limited to, groups such as phenoxy, 2-, 3-, or 4-methylphenoxy, and the like.

The term "halogen" as used herein refer to Cl, Br, F or I substituents, preferably fluoro or chloro.

The term "—$(C_1–C_{12})$ alkyl, substituted alkyl, or heteroalkyl" means an alkyl, substituted alkyl or heteroalkyl group respectively as defined above and having 1 to 12 carbon atoms. For example, when $R_{11}$ is —$(C_1–C_{12})$ alkyl, substituted alkyl, or heteroalkyl it means that $R_{11}$ can be —$(C_1–C_{12})$ alkyl or —$(C_1–C_{12})$substituted alkyl, or —$(C_1–C_{12})$heteroalkyl.

The term "—$(C_1–C_{12})$ alkenyl, substituted alkenyl, or heteroalkenyl" means an alkenyl, substituted alkenyl, or heteroalkenyl group as defined above and having 1 to 12 carbon atoms.

The term "—$(C_1–C_{12})$ alkynyl, substituted alkynyl, or heteroalkynyl" means an alkynyl, substituted alkynyl, or heteroalkynyl group as defined above and having 1 to 12 carbon atoms.

The term "—$(C_1–C_{12})$ alkylene, substituted alkylene, or heteroalkylene" means an alkylene, substituted alkylene, or heteroalkylene group as defined above and having1 to 12 carbon atoms.

The term "—$(C_1–C_{12})$ alkenylene, substituted alkenylene, or heteroalkenylene" means that the alkenylene, substituted alkenylene, or heteroalkenylene group as defined above and having 1 to 12 carbon atoms.

The term "—$(C_1–C_{12})$ alkynylene, substituted alkynylene, or heteroalkynylene" means that the alkynylene, substituted alkynylene, or heteroalkynylene groups have 1 to 12 carbon atoms.

The term "—(C$_0$–C$_8$alkylene or substituted alkylene)-(C$_3$–C$_{12}$arylene or heteroarylene)-(C$_0$–C$_8$ alkyl or substituted alkyl)" means that "—(C$_0$–C$_8$alkylene or substituted alkylene)-" is a covalent bond when there are zero carbon atoms i.e., C$_0$; or the alkylene or substituted alkylene group can have 1 to 8 carbon atoms. Similarly, —(C$_0$–C$_8$ alkyl or substituted alkyl)- means that "—(C$_0$–C$_8$ alkyl or substituted alkyl)-" is a covalent bond when there are zero carbon atoms i.e., C$_0$; or the alkyl or substituted alkyl group can have 1 to 8 carbon atoms. The term —(C$_3$–C$_{12}$ arylene or heteroarylene)- means that the arylene has 6 to 12 carbon atoms (e.g., phenyl, naphtyl, and the like) and heteroarylene groups have 3 to 12 carbons atoms and additionally contain one to three heteroatoms including, but not limited to, heteroatoms such as N, O, P, or S, within the ring (e.g., 2,6-pyridylene, 2,4-pyridinylene, 1,2-quinolinylene, 1,8-quinolinylene, 1,4-benzofuranylene, 2,5-pyridylene, 2,5-indolenyl, and the like) in accordance with the definition of heteroarylene above. Additionally, it will be recognized by a person skilled in the art that when "—(C$_0$–C$_8$ alkylene or substituted alkylene)-" and "—(C$_0$–C$_8$ alkyl or substituted alkyl)-" are a covalent bond then —(C$_3$–C$_{12}$ arylene or heteroarylene)- is an aryl or heteroaryl group as defined above.

"Protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Greene et al. (1991) *Protective Groups in Organic Synthesis*, 2nd Ed. (John Wiley & Sons, Inc., New York). Preferred amino protecting groups include, but are not limited to, benzyloxycarbonyl (CBz), t-butyloxycarbonyl (Boc), t-butyldimethylsilyl (TBDIMS), 9-fluorenylmethyloxycarbonyl (Fmoc), or suitable photolabile protecting groups such as 6-nitroveratryloxy carbonyl (Nvoc), nitropiperonyl, pyrenylmethoxycarbonyl, nitrobenzyl, dimethyl dimethoxybenzil, 5-bromo-7-nitroindolinyl, and the like. Preferred hydroxyl protecting groups include Fmoc, TBDIMS, photolabile protecting groups (such as nitroveratryl oxymethyl ether (Nvom)), Mom (methoxy methyl ether), and Mem (methoxy ethoxy methyl ether). Particularly preferred protecting groups include NPEOC (4-nitrophenethyloxycarbonyl) and NPEOM (4-nitrophenethyloxymethyloxycarbonyl).

"Inhibitor" refers to a compound that interferes with the interaction between a target and its respective substrate(s) or endogenous ligand(s). Target molecules include, but are not limited to, enzymes and receptors. Enzyme inhibitors have been extensively studied from kinetic and mechanistic standpoints; see, e.g., Fersht, A., *Enzyme Structure and Mechanism*, 2nd Ed., New York, W. H. Freeman, 1985. A useful measure of the effectiveness of a compound at inhibiting enzyme catalysis is the IC$_{50}$ of that compound. The IC$_{50}$ of a compound can determined by the equation $y=y_o/(1+[In]/IC_{50})$ where y is the measured reaction velocity, y$_o$ is the reaction velocity in the absence of inhibitor, and [In] is the inhibitor concentration. Solving this equation at the inhibitor concentration [In] when y=y$_o$/2 yields IC$_{50}$ of the inhibitor for the enzyme under study. Useful inhibitors have an IC$_{50}$ equal to or less than about 10 μM, preferably equal to or less than about 1 μM. More preferably, the inhibitor has an IC$_{50}$ equal to or less than about 100 nM, still more preferably equal to or less than about 10 nM, even more preferably equal to or less than about 1 nM. Most preferably, inhibitors have an IC$_{50}$ equal to or less than about 100 pM, or equal to or less than about 10 pM.

A selective inhibitor refers to an inhibitor that will inhibit the activity of one macromolecule, typically an enzyme, while exhibiting little or no inhibitory effect on another macromolecule, typically another enzyme. The compounds of the invention are particularly useful in that they display selective inhibition of peptide deformylase while exhibiting much lower inhibitory activity towards metalloproteinases such as matrilysin. The selectivity of an enzyme inhibitor can be indicated by dividing the IC$_{50}$ of the compound for the enzyme which is not intended to be inhibited, by the IC$_{50}$ of the compound for the enzyme which is intended to be inhibited. Thus, if a compound has an IC$_{50}$ for matrilysin of 1 μM, and an IC$_{50}$ for peptide deformylase of 0.01 μM, the compound displays a 100-fold (or 100 times) selectivity for peptide deformylase over matrilysin, or alternatively is said to be 100 times more selective for peptide deformylase compared to matrilysin. Useful compounds display a selectivity of greater than or equal to about 10 times, preferably greater than or equal to about 100 times, more preferably greater than or equal to about 1000 times, still more preferably greater than or equal to about 10,000, for peptide deformylase over one or more other metalloproteinases, for example for peptide deformylase over matrilysin.

The compounds of the invention are intended for use in eukaryotic animals. Preferably, the animal is a vertebrate; more preferably, the animal is a mammal; most preferably, the animal is a human.

By "hydroxamic acid derivative," "hydroxamic acid derivative compound," "hydroxamic acid compound," "hydroxamate derivative," "hydroxamate derivative compound," or "hydroxamate compound" is meant any compound containing the functional group HN(OH)—C (=O)—.

Compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. For example, if the R$_{12}$ substituent in a compound of formula (I) is 2-hydroxyethyl, then the carbon to which the hydroxy group is attached is an asymmetric center and therefore the compound of Formula (I) can exist as an (R)- or (S)-stereoisomer. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-napthalenesulfonic acid, 4-toluenesulfonic acid, camphorsulfonic acid, 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A compound of Formula (I) may act as a pro-drug. Prodrug means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy, amino, or sulfhydryl group in compound (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of Formula (I), and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Inhibiting bacterial growth" means arresting or reducing the development of the bacteria or killing bacteria.

A "inert diluent" means an excipient that is useful in preparing a composition that is generally safe, non-toxic and neither biologically nor otherwise undesirable.

PREFERRED EMBODIMENTS

While the broadest definition of this invention is set forth in the Summary of the Invention, certain compounds of Formula (I) are preferred.

(A) A preferred group of compounds is that wherein the embodiments of (i), (ii) and (iii) defined below are employed either singularly or in any combination:

(i) $R_{10}$ is hydrogen, alkyl or -alkylene-OH, preferably hydrogen, methyl, -hydroxymethyl, more preferably hydrogen.

(ii) $R_{11}$ is alkyl, substituted alkyl, alkenyl, heteroaralkyl, or heteroalkyl. Preferably, methyl, ethyl, butyl, 3-methylbutyl, pentyl, 2-cyclohex-1-enylethyl, 2-(2-fluorophenyl)ethyl, 3-ethoxypropyl, 2-(thiophenyl-2-yl)ethyl, 2-cyclopentylethyl, 1-napthylmethyl, 4-fluorobenzyl, 2-ethylthioethyl, or 2-(4-chlorophenyl)ethyl. Even more preferably, $R_{11}$ is 3-methylbutyl or 2-cyclopentylethyl.

(iii) the

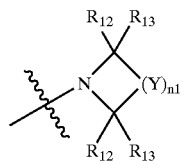

group is a group of formula:

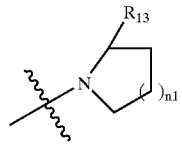

wherein:

n1 is 1 or 2, preferably 1.

$R_{13}$ is $-C(=O)NR_{17}R_{18}$, $-N(R_{17})C(=O)OR_{18}$ or $-C(=O)OR_{17}$ where $R_{17}$ and $R_{18}$ are each independently hydrogen, $-(C_1-C_{12})$ alkyl, substituted alkyl, or heteroalkyl, $-(C_1-C_{12})$ alkenyl, substituted alkenyl, or heteroalkenyl, $-(C_1-C_{12})$ alkynyl, substituted alkynyl, or heteroalkynyl, alkoxy, or $-(C_0-C_8$ alkyl or substituted alkyl)-$(C_3-C_{12}$ arylene or heteroarylene)-$(C_0-C_8$ alkyl or substituted alkyl), or when $R_{17}$ and $R_{18}$ are attached to the same atom, they can combine to form a substituted or unsubstituted $-(C_4-C_{10})$cyclic alkyl, cyclic heteroalkyl, aryl or heteroaryl group. Preferably, $R_{13}$ is $-C(=O)NR_{17}R_{18}$, $-N(R_{17})C(=O)OR_{18}$ or $-C(=O)OR_{17}$ where $R_{17}$ and $R_{18}$ are each independently hydrogen or $-(C_1-C_{12})$ alkyl, alkoxy, aryl, heteroaryl or $R_{17}$ and $R_{18}$, when attached to the same carbon, combine to form a cyclic heteroalkyl, aryl or heteroaryl group. More preferably, $R_{13}$ is —C(=O)NHR$_{18}$ where $R_{18}$ is H or —(C$_1$–C$_{12}$) alkyl, aryl, heteroaryl, —C(=O)NR$_{17}$R$_{18}$ where $R_{17}$ and $R_{18}$ form a substituted or unsubstituted —(C$_4$–C$_{10}$) cyclic heteroalkyl or —C(=O)OR$_{17}$ where $R_{17}$ is alkyl, even more preferably $R_{13}$ is 3-phenoxyphenylaminocarbonyl, phenylaminocarbonyl, 2-methyl-1,3,4-thiadiazol-5-yl-aminocarbonyl, thiazol-2-ylaminocarbonyl, 6-phenylimidazol-2-ylaminocarbonyl, pyrazin-2-ylaminocarbonyl, 3-methylbutylaminocarbonyl, imidazol-2-ylaminocarbonyl, 4,5-dimethylthiazol-2-ylaminocarbonyl, tert-butoxycarbonylamino, piperidin-1-ylcarbonyl, tert-butoxycarbonyl, methylaminocarbonyl, or 4-benzylpiperazin-1-ylcarbonyl. Particularly preferably, $R1_{13}$ is 3-phenoxyphenylaminocarbonyl, 2-methyl-1,3,4-thiadiazol-5-yl-aminocarbonyl, thiazol-2-ylaminocarbonyl, 6-phenylimidazol-2-ylaminocarbonyl, pyrazin-2-ylaminocarbonyl, 3-methylbutylaminocarbonyl, imidazol-2-ylaminocarbonyl, or 4,5-dimethylthiazol-2-ylaminocarbonyl.

(B) Another preferred group of compounds is represented by Formula (Ia):

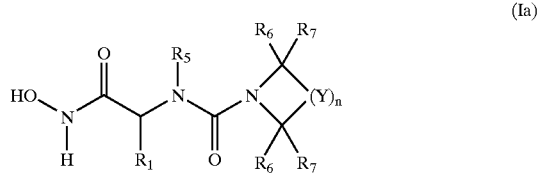

(Ia)

wherein:

$R_1$ is selected from the group consisting of hydrogen, $R_s$, and —R$_t$—O—R$_s$ where $R_s$ is selected from the group consisting of —(C$_1$–C$_{12}$) alkyl, —(C$_1$–C$_{12}$) alkenyl, and —(C$_1$–C$_{12}$) alkynyl; and $R_t$ is selected from the group consisting of —(C$_1$–C$_{12}$) alkylene, —(C$_1$–C$_{12}$) alkenylene, and —(C$_1$–C$_{12}$) alkynylene;

$R_5$ is selected from the group consisting of hydrogen, —(C$_1$–C$_{12}$) alkyl, substituted alkyl, or heteroalkyl, —(C$_1$–C$_{12}$) alkenyl, substituted alkenyl, or heteroalkenyl, —(C$_1$–C$_{12}$) alkynyl, substituted alkynyl, or heteroalkynyl, and —(C$_0$–C$_{12}$ alkylene or substituted alkylene)-(C$_3$–C$_{12}$ arylene or heteroarylene)-(C$_0$–C$_{12}$ alkyl or substituted alkyl);

n is an integer from 1 to 5;

zero or one Y is selected from the group consisting of —O—, —NR$_a$—, and —S—, and all remaining Y are —CR$_6$R$_7$—; and where $R_6$ and $R_7$ are each independently hydrogen, $R_c$, —OH, —OR$_c$, —SH, —SR$_c$, —NH$_2$, —NHR$_c$, —NR$_c$R$_d$, —C(=O)R$_c$, —C(=O) NR$_c$R$_d$, —C(=O)OR$_c$, —C(=O)SR$_c$, —C(=O) CR$_c$R$_d$R$_e$, —C(=O)OCR$_c$R$_d$R$_e$, —S(=O)$_2$NR$_c$R$_d$, —N(R$_c$)C(=O)R$_d$, —N(R$_c$)C(=O)OR$_d$, —N(R$_c$)S (=O)$_2$R$_d$, or —N(R$_c$)S(=O)$_2$OR$_d$, or where two vicinal $R_6$ or $R_7$ groups combine to form a substituted or unsubstituted C$_4$–C$_{10}$ cyclic alkyl, cyclic heteroalkyl, aryl or heteroaryl group; where $R_c$, $R_d$ and $R_e$ are each independently hydrogen, —(C$_1$–C$_{12}$) alkyl, substituted alkyl, or heteroalkyl, —(C$_1$–C$_{12}$) alkenyl, substituted alkenyl, or heteroalkenyl, —(C$_1$–C$_{12}$) alkynyl, substituted alkynyl, or heteroalkynyl, or —(C$_0$–C$_8$ alkylene or substituted alkylene)-(C$_3$–C$_{12}$ arylene or heteroarylene)-(C$_0$–C$_8$ alkyl or substituted alkyl), or where, when two or three of $R_c$, $R_d$ and $R_e$ are attached to the same atom, two or three of $R_c$, $R_d$ and $R_e$ can combine to form a substituted or unsubstituted —(C$_4$–C$_{10}$) cyclic alkyl, cyclic heteroalkyl, aryl or heteroaryl group; and all salts and stereoisomers thereof.

In one embodiment of this series of compounds, $R_1$ is hydrogen, alkyl, or -alkylene-OH, preferably hydrogen, methyl, or hydroxymethyl, more preferably hydrogen. In another embodiment of this series of compounds, $R_5$ is is alkyl, substituted alkyl, alkenyl, heteroaralkyl, or heteroalkyl. Preferably, methyl, ethyl, butyl, 3-methylbutyl, pentyl, 2-cyclohex-1-enylethyl, 2-(2-fluorophenyl)ethyl, 3-ethoxypropyl, 2-(thiophenyl-2-yl)ethyl, 2-cyclohexylethyl, 1-napthylmethyl, 4-fluorobenzyl, 2-ethylthioethyl, 2-cyclopentylethyl, or 2-(4-chlorophenyl)-ethyl. Even more preferably, $R_5$ is 3-methylbutyl or 2-cyclopentylethyl.

In yet another embodiment of this series of compounds, the

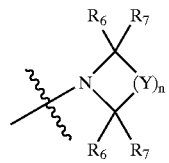

group is a group of formula:

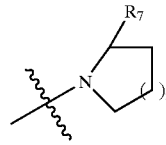

wherein:

n is 1 or 2, preferably 1; and $R_7$ is —C(=O)NR$_c$R$_d$, —N(R$_c$)C(=O)OR$_d$ or —C(=O) OR$_c$ where $R_c$ and $R_d$ are each independently hydrogen, —(C$_1$–C$_{12}$) alkyl, substituted alkyl, or heteroalkyl, —(C$_1$–C$_{12}$) alkenyl, substituted alkenyl, or heteroalkenyl, —(C$_1$–C$_{12}$) alkynyl, substituted alkynyl, or heteroalkynyl, alkoxy, or —(C$_0$–C$_8$ alkylene or substituted alkylene)-(C$_3$–C$_{12}$ arylene or heteroarylene)-(C$_0$–C$_8$ alkyl or substituted alkyl), or where $R_c$ and $R_d$ are attached to the same atom, they can combine to form a substituted or unsubstituted —(C$_4$–C$_{10}$)cyclic alkyl, cyclic heteroalkyl, aryl or heteroaryl group. Preferably, $R_7$ is —C(=O)NR$_c$R$_d$, —N(R$_c$)C(=O)OR$_d$ or —C(=O)OR$_c$ where $R_c$ and $R_d$ are each independently hydrogen, —(C$_1$–C$_{12}$) alkyl, or aryl, or when $R_c$ and $R_d$ are attached to the same atom, they can combine to form a cyclic heteroalkyl, aryl or heteroaryl group. Even more preferably, $R_7$ is hydrogen, —(C$_1$–C$_{12}$) alkyl, aryl, or heteroaryl or $R_c$ and $R_d$, when attached to the same carbon, combine to form a cyclic heteroalkyl, aryl or heteroaryl group. More preferably, $R_7$ is —C(=O)NHR$_d$ where $R_d$ is hydrogen, —(C$_1$–C$_{12}$) alkyl, aryl, heteroaryl, —C(=O)NR$_c$R$_d$ where $R_c$ and $R_d$, when attached to the same carbon, combine to form a cyclic heteroalkyl or —C(=O)OR$_c$ where $R_c$ is —(C$_1$–C$_{12}$) alkyl. $R_7$ is even more preferably 3-phenoxyphenylaminocarbonyl, phenylaminocarbonyl, 2-methyl-1,3,4-thiadiazol-5-ylaminocarbonyl, thiazol-2-ylaminocarbonyl, 6-phenylimidazol-2-ylaminocarbonyl, pyrazin-2-ylaminocarbonyl, 3-methylbutylaminocarbonyl, imidazol-2-ylaminocarbonyl, 4,5-dimethylthiazol-2-ylaminocarbonyl, tert-butoxycarbonylamino, piperidin-1-ylcarbonyl, tert-butoxycarbonyl, methylaminocarbonyl, or 4-benzylpiperazin-1-ylcarbonyl. Particularly preferably, $R_7$ is 3-phenoxyphenylaminocarbonyl, 2-methyl-1,3,4-thiadiazol-5-ylaminocarbonyl, thiazol-2-ylaminocarbonyl, 6-phenylimidazol-2-ylaminocarbonyl, pyrazin-2-ylaminocarbonyl, 3-methylbutylaminocarbonyl, imidazol-2-ylaminocarbonyl, or 4,5-dimethylthiazol-2-ylaminocarbonyl.

In yet another embodiment of this series of compounds, the

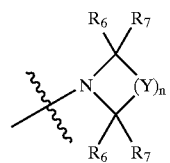

group is a group of formula:

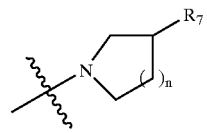

wherein:
n is 1 or 2, preferably 1; and
$R_7$ is —C(═O)$NR_cR_d$, —N($R_c$)C(═O)$OR_d$ or —C(═O)$OR_c$ where $R_c$ and $R_d$ are each independently hydrogen, —($C_1$–$C_{12}$) alkyl, substituted alkyl, or heteroalkyl, —($C_1$–$C_{12}$) alkenyl, substituted alkenyl, or heteroalkenyl, —($C_1$–$C_{12}$) alkynyl, substituted alkynyl, or heteroalkynyl, alkoxy, or —($C_0$–$C_8$) alkylene or substituted alkylene)-($C_3$–$C_{12}$ arylene or heteroarylene)-($C_0$–C8 alkyl or substituted alkyl), or where $R_c$ and $R_d$ are attached to the same atom, they can combine to form a substituted or unsubstituted —($C_4$–$C_{10}$)cyclic alkyl, cyclic heteroalkyl, aryl or heteroaryl group. Preferably, $R_7$ is —C(═O)$NR_cR_d$, —N($R_c$)C(═O)$OR_d$ or —C(═O)$OR_c$ where $R_c$ and $R_d$ are each independently hydrogen or —($C_1$–$C_{12}$) alkyl, aryl, or when $R_c$ and $R_d$ are attached to the same atom, they can combine to form a cyclic heteroalkyl, aryl or heteroaryl group. Even more preferably, $R_7$ is hydrogen or —($C_1$–$C_{12}$) alkyl, aryl, or heteroaryl or $R_c$ and $R_d$, when attached to the same carbon, combine to form a cyclic heteroalkyl, aryl or heteroaryl group. More preferably, $R_7$ is —C(═O)$NHR_d$ where $R_d$ is hydrogen or —($C_1$–$C_{12}$) alkyl, aryl, heteroaryl, —C(═O)$NR_cR_d$ where $R_c$ and $R_d$, when attached to the same carbon, combine to form a cyclic heteroalkyl or —C(═O)$OR_c$ where $R_c$ is —($C_1$–$C_{12}$) alkyl. $R_7$ is even more preferably 3-phenoxyphenylaminocarbonyl, phenylaminocarbonyl, 2-methyl-1,3,4-thiadiazol-5-ylaminocarbonyl, thiazol-2-ylaminocarbonyl, 6-phenylimidazol-2-ylaminocarbonyl, pyrazin-2-ylaminocarbonyl, 3-methylbutylaminocarbonyl, imidazol-2-ylaminocarbonyl, 4,5-dimethylthiazol-2-ylaminocarbonyl, tert-butoxycarbonylamino, piperidin-1-ylcarbonyl, tert-butoxycarbonyl, methylaminocarbonyl, or 4-benzylpiperazin-1-ylcarbonyl. Particularly preferably, $R_7$ is 3-phenoxyphenylaminocarbonyl, 2-methyl-1,3,4-thiadiazol-5-ylaminocarbonyl, thiazol-2-ylaminocarbonyl, 6-phenylimidazol-2-ylaminocarbonyl, pyrazin-2-ylaminocarbonyl, 3-methylbutylaminocarbonyl, imidazol-2-ylaminocarbonyl, or 4,5-dimethylthiazol-2-ylaminocarbonyl.

(C) Another preferred group of compounds is represented by Formula (Ib):

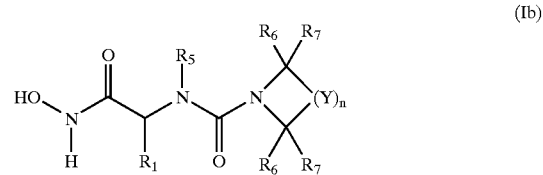

(Ib)

wherein:
$R_1$ is selected from the group consisting of hydrogen, $R_a$, —$R_b$—OH, and —$R_b$—O—$R_a$ where $R_a$ is selected from the group consisting of —($C_1$–$C_{12}$) alkyl, substituted alkyl, or heteroalkyl, —($C_1$–$C_{12}$) alkenyl, substituted alkenyl, or heteroalkenyl, —($C_1$–$C_{12}$) alkynyl, substituted alkynyl, or heteroalkynyl, or —($C_0$–$C_8$ alkyl or substituted alkyl)-($C_3$–$C_{12}$ aryl or heteroaryl)-($C_0$–$C_8$ alkyl or substituted alkyl); and $R_b$ is selected from the group consisting of —($C_1$–$C_{12}$) alkylene, substituted alkylene, or heteroalkylene, —($C_1$–$C_{12}$) alkenylene, substituted alkenylene, or heteroalkenylene, —($C_1$–$C_{12}$) alkynylene, substituted alkynylene, or heteroalkynylene, or —($C_0$–$C_8$ alkylene or substituted alkylene)-($C_3$–$C_{12}$ arylene or heteroarylene)-($C_0$–$C_8$ alkyl or substituted alkyl);

$R_5$ is selected from the group consisting of hydrogen, —($C_1$–$C_{12}$) alkyl, substituted alkyl, or heteroalkyl, —($C_1$–$C_{12}$) alkenyl, substituted alkenyl, or heteroalkenyl, —($C_1$–$C_{12}$) alkynyl, substituted alkynyl, or heteroalkynyl, or —($C_0$–$C_{12}$ alkyl or substituted alkyl)-($C_3$–$C_{12}$ aryl or heteroaryl)-($C_0$–$C_{12}$ alkyl or substituted alkyl);

n is an integer from 1 to 5;

zero or one Y is selected from the group consisting of —O—, —$NR_a$—, and —S—, and all remaining Y are —$CR_6R_7$—; and $R_6$ and $R_7$ are each independently —H, —$R_h$, —OH, —$OR_h$, —SH, —$SR_h$, —$NH_2$, —$NHR_h$, —$NR_hR_i$, —C(═O)H, —C(═O)$R_h$, —C(═O)$NH_2$, —C(═O)$NHR_h$, —C(═O)$NR_hR_i$, —C(═O)OH, —C(═O)$OR_h$, —C(═O)SH, —C(═O)$SR_h$, —C(═O)$CH_3$, —C(═O)$CH_2R_h$, —C(═O)$CHR_hR_i$, —C(═O)$CR_hR_iR_j$, —C(═O) $OCH_3$, —C(═O)$OCH_2R_h$, —C(═O)$OCHR_hR_i$, —C(═O)$OCR_hR_iR_j$, —S(═O)$_2NH_2$, —S(═O)$_2$ $NHR_h$, —S(═O)$_2NR_hR_i$, —NHC(═O)H, —N($R_h$)C (═O)H, —NHC(═O)$R_i$, —NHC(═O)$OR_i$, —N($R_h$) C(═O)$R_i$, —N($R_h$)C(═O)$OR_i$, —NHS(═O)$_2$H, —N($R_h$)S(═O)$_2$H, —NHS(═O)$_2OR_i$, —N($R_h$)S (═O)$_2OR_i$, —N(H)S(═O)$_2R_i$, or —N($R_h$)S(═O)$_2R_i$; where $R_h$, $R_i$ and $R_j$ are each independently —($C_1$–$C_{12}$) alkyl, substituted alkyl, or heteroalkyl, —($C_1$–$C_{12}$)

alkenyl, substituted alkenyl, or heteroalkenyl, —(C₁–C₁₂) alkynyl, substituted alkynyl, or heteroalkynyl, alkoxy, or —(C₀–C₈ alkylene or substituted alkylene)-(C₃–C₁₂ arylene or heteroarylene)-(C₀–C₈ alkyl or substituted alkyl) or a pharmaceutically acceptable salt thereof.

In one embodiment of this series of compounds, R₁ is hydrogen, alkyl, or -alkylene-OH, preferably hydrogen, methyl, or hydroxymethyl, more preferably hydrogen. In another embodiment of this series of compounds, R₅ is is alkyl, substituted alkyl, alkenyl, heteroaralkyl, or heteroalkyl. Preferably, methyl, ethyl, butyl, 3-methylbutyl, pentyl, 2-cyclohex-1-enylethyl, 2-(2-fluorophenyl)ethyl, 3-ethoxypropyl, 2-(thiophenyl-2-yl)ethyl, 2-cyclohexylethyl, 1-napthylmethyl, 4-fluorobenzyl, 2-ethylthioethyl, 2-cyclopentylethyl or 2-(4-chlorophenyl)-ethyl. Even more preferably, R₅ is 33-methylbutyl or 2-cyclopentylethyl.

In yet another embodiment of this series of compounds, the group

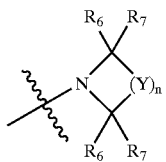

is a group of formula:

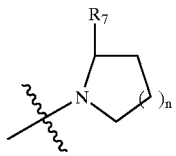

wherein:
n is 1 or 2, preferably 1; and
R₇ is —C(=O)NR_cR_d, —N(R_c)C(=O)OR_d or —C(=O)OR_c where R_c and R_d are each independently hydrogen, —(C₁–C₁₂) alkyl, substituted alkyl, or heteroalkyl, —(C₁–C₁₂) alkenyl, substituted alkenyl, or heteroalkenyl, —(C₁–C₁₂) alkynyl, substituted alkynyl, or heteroalkynyl, or —(C₀–C₈ alkyl or substituted alkyl)-(C₃–C₁₂ aryl or heteroaryl)-(C₀–C₈ alkyl or substituted alkyl), or where R_c and R_d are attached to the same atom, they can combine to form a substituted or unsubstituted (C₄–C₁₀)cyclic alkyl, cyclic heteroalkyl, aryl or heteroaryl group. Preferably, R₇ is —C(=O)NR_cR_d, —N(R_c)C(=O)OR_d or —C(=O)OR_c where R_c and R_d are each independently hydrogen or —(C₁–C₁₂) alkyl, aryl, or where R_c and R_d are attached to the same atom, they can combine to form a cyclic heteroalkyl, aryl or heteroaryl group. Even more preferably, R₇ is hydrogen, —(C₁–C₁₂) alkyl, aryl, or heteroaryl or R_c and R_d, when attached to the same carbon, combine to form a cyclic heteroalkyl, aryl or heteroaryl group. More preferably, R₇ is —C(=O)NHR_d where R_d is hydrogen, C₁–C₁₂ alkyl, aryl, or heteroaryl, even more preferably 3-phenoxyphenylaminocarbonyl, phenylaminocarbonyl, 2-methyl-1,3,4-thiadiazol-5-ylaminocarbonyl, thiazol-2-ylamino-carbonyl, 6-phenylimidazol-2-ylaminocarbonyl, pyrazin-2-ylaminocarbonyl, 3-methylbutyl-aminocarbonyl, imidazol-2-ylaminocarbonyl, 4,5-dimethylthiazol-2-ylaminocarbonyl, tert-butoxycarbonylamino, piperidin-1-ylcarbonyl, tert-butoxycarbonyl, methylaminocarbonyl, or 4-benzylpiperazin-1-ylcarbonyl. Particularly preferably, R₇ is 3-phenoxyphenyl-aminocarbonyl, 2-methyl-1,3,4-thiadiazol-5-ylaminocarbonyl, thiazol-2-ylaminocarbonyl, 6-phenylimidazol-2-ylaminocarbonyl, pyrazin-2-ylaminocarbonyl, 3-methylbutyl-aminocarbonyl, imidazol-2-ylaminocarbonyl, or 4,5-dimethylthiazol-2-ylaminocarbonyl.

In yet another embodiment of this series of compounds, the group

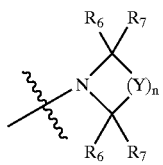

is a group of formula:

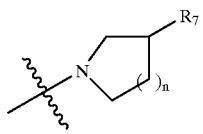

wherein:
n is 1 or 2, preferably 1; and
R₇ is —C(=O)NR_cR_d, —N(R_c)C(=O)OR_d or —C(=O)OR_c where R_c and R_d are each independently hydrogen, —(C₁–C₁₂) alkyl, substituted alkyl, or heteroalkyl, —(C₁–C₁₂) alkenyl, substituted alkenyl, or heteroalkenyl, —(C₁–C₁₂) alkynyl, substituted alkynyl, or heteroalkynyl, or —(C₀–C₈ alkyl or substituted alkyl)-(C₃–C₁₂ aryl or heteroaryl)-(C₀–C₈ alkyl or substituted alkyl), or where R_c and R_d are attached to the same atom, they can combine to form a substituted or unsubstituted (C₄–C₁₀)cyclic alkyl, cyclic heteroalkyl, aryl or heteroaryl group. Preferably, R₇ is —C(=O)NR_cR_d, —N(R_c)C(=O)OR_d or —C(=O)OR_c where R_c and R_d are each independantly hydrogen, —(C₁–C₁₂) alkyl, or aryl, or where R_c and R_d are attached to the same atom, they can combine to form a cyclic heteroalkyl, aryl or heteroaryl group. Even more preferably, R₇ is hydrogen or —(C₁–C₁₂) alkyl, aryl, heteroaryl or R_c and R_d, when attached to the same carbon, combine to form a cyclic heteroalkyl, aryl or heteroaryl group. More prefarably, R₇ is —C(=O)NHR_d where R_d is hydrogen or C₁–C₁₂ alkyl, aryl, heteroaryl. Even more preferably R₇ is 3-phenoxyphenylaminocarbonyl, phenylaminocarbonyl, 2-methyl-1,3,4-thiadiazol-5-ylaminocarbonyl, thiazol-2-ylamino-carbonyl, 6-phenylimidazol-2-ylaminocarbonyl, pyrazin-2-ylaminocarbonyl, 3-methylbutyl-aminocarbonyl, imidazol-2-ylamioncarbonyl, 4,5-dimethylthiazol-2-ylaminocarbonyl, tert-butoxycarbonylamino, piperidin-1-ylcarbonyl, tert-butoxycarbonyl, methylaminocarbonyl, or 4-benzylpiperazin-1-ylcarbonyl. Particularly preferably, R₇ is 3-phenoxyphenyl-aminocarbonyl, 2-methyl-1,3,4-thiadiazol-5-ylaminocarbonyl, thiazol-2- ylaminocarbonyl, 6-phenylimidazol-2-ylaminocarbonyl, pyrazin-2-ylaminocarbonyl, 3-methylbutyl-aminocarbonyl, imidazol-2-ylaminocarbonyl, or 4,5-dimethylthiazol-2-ylaminocarbonyl.

A number of different substituent preferences have been given in the list above, and following these substituent preferences results in a compound of this invention that is more preferred any one in which the particular substituent preference is not followed. However, these substituent preferences are generally independent, although some preferences are mutually exclusive, and following more than one of the substituent preferences results in a more preferred compound than one in which fewer of the substituent preferences are followed. Thus, particularly preferred compounds of this invention are those in which (to the extent possible) most of the above preferences are followed.

Preferred compounds of the Invention are shown below:

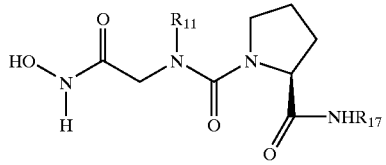

| Cpd # | $R_{11}$ | $R_{17}$ |
|---|---|---|
| 1 | 3-methylbutyl | 3-phenoxyphenyl |
| 2 | 2-cyclopentylethyl | 2-methyl-1,3,4-thiadiazol-5-yl |
| 3 | 2-cyclopentylethyl | thiazol-2-yl |
| 4 | 2-cyclopentylethyl | 6-phenylimidazol-2-yl |
| 5 | 2-cyclopentylethyl | pyrazin-2-yl |
| 6 | 3-methylbutyl | 3-methylbutyl |
| 7 | 2-cyclopentylethyl | imidazol-2-yl |
| 8 | 3-methylbutyl | 4,5-dimethylthiazol-2-yl |
| 9 | 2-cyclopentylethyl | 4,5-dimethylthiazol-2-yl | and are named as:

N-hydroxy-2-[N-(3-methylbutyl)-N-(2-(S)-3-phenoxyphenylaminocarbonyl)-pyrrolidin-1-carbonyl)amino]acetamide;

N-hydroxy-2-[N-(2-cyclopentylethyl)-N-(2-(S)-2-methyl-1,3,4-thiadiazol-5-ylaminocarbonyl)pyrrolidin-1-carbonyl)amino]acetamide;

N-hydroxy-2-[N-(2-cyclopentylethyl)-N-(2-(S)-thiazol-2-ylaminocarbonyl)-pyrrolidin-1-carbonyl)amino]acetamide;

N-hydroxy-2-[N-(2-cyclopentylethyl)-N-(2-(S)-6-phenylimidazol-2-ylaminocarbonyl)-pyrrolidin-1-carbonyl)amino]acetamide;

N-hydroxy-2-[N-(2-cyclopentylethyl)-N-(2-(S)-pyrazin-2-ylaminocarbonyl)-pyrrolidin-1-carbonyl)amino]acetamide;

N-hydroxy-2-[N-(3-methylbutyl)-N-(2-(S)-3-methylbutylaminocarbonyl)-pyrrolidin-1-carbonyl)amino]acetamide;

N-hydroxy-2-[N-(2-cyclopentylethyl)-N-(2-(S)-imidazol-2-ylaminocarbonyl)-pyrrolidin-1-carbonyl)amino]acetamide;

N-hydroxy-2-[N-(2-cyclopentylethyl)-N-(2-(S)-4,5-dimethylthiazol-2-ylaminocarbonyl)-pyrrolidin-1-carbonyl)amino]acetamide; and N-hydroxy-2-[N-(3-methylbutyl)-N-(2-(S)-4,5-dimethylthiazol-2-ylaminocarbonyl)-pyrrolidin-1-carbonyl)amino]acetamide.

General Synthetic Scheme

Compounds of this invention can be made by the methods depicted in the reaction schemes shown below.

The starting materials and reagents used in preparing these compounds are either available from commercial suppliers such as Aldrich Chemical Co., (Milwaukee, Wis., USA), Bachem (Torrance, Calif., USA), Emka-Chemie, or Sigma (St. Louis, Mo., USA) or are prepared by methods known to those skilled in the art following procedures set forth in references such as Fieser and Fieser's Reagents for Organic Synthesis, Volumes 1–15 (John Wiley and Sons, 1991); Rodd's Chemistry of Carbon Compounds, Volumes 1–5 and Supplementals (Elsevier Science Publishers, 1989), Organic Reactions, Volumes 1–40 (John Wiley and Sons, 1991), March's Advanced Organic Chemistry, (John Wiley and Sons, 4th Edition), and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Preparation of Compounds of Formula (I)

Compounds of Formula (I) can be prepared as described in Schemes A–D below.

In general, a compound of Formula (I) can be prepared as illustrated and described in Scheme A below.

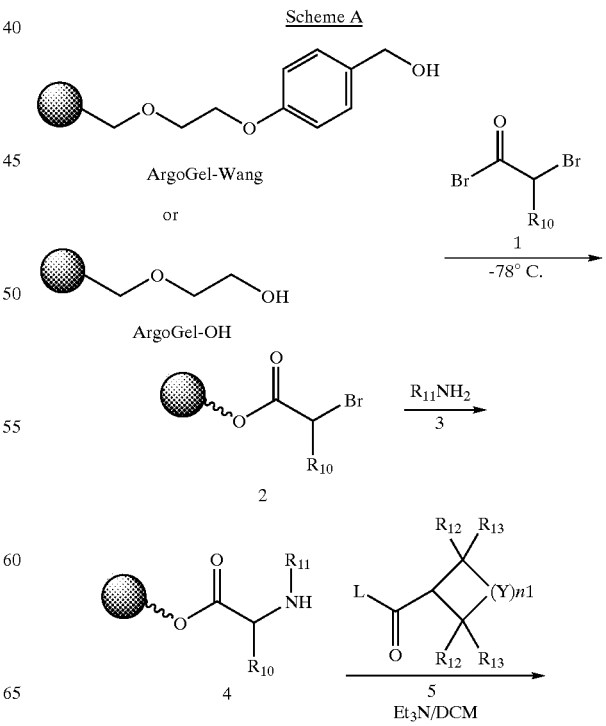

Scheme A

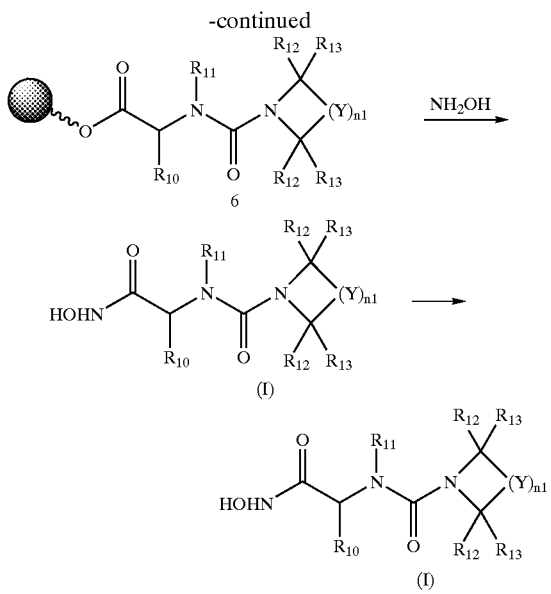

Treatment of a suspension of ArgoGel-Wang or ArgoGel-OH resin with a bromoacetyl derivative of formula 1 wherein $R_{10}$ is defined in the Summary of the Invention provides a resin bound bromoacetate derivative of formula 2. The reaction is typically carried out in the presence of a non-nucleophilic base such as 2,4,6-collidine, pyridine, and the like and in an inert organic solvent such as dichloromethane and the like. The reaction is carried out at a low temperature, preferably at about −78° C. Compounds of formula 1 are commercially available or they can be prepared by methods well known in the art. For examples, bromoacetyl bromide, 2-bromopropionyl bromide are commercially available. Others can be prepared from commercially available amino acids via diazotization of the alpha amine and displacement with bromide ion. The resulting alpha bromoacid can then be converted to a suitable acid halide such as acid chloride or bromide using, for example, thionyl chloride or thionyl bromide.

Substitution of the bromo group in 2 with an amine of formula 3 where $R_{11}$ is as defined in the Summary of the Invention provides a resin bound amino ester derivative of formula 4. The reaction is typically carried at ambient temperature and in a polar organic solvent such as dimethylformamide, and the like. Compounds of formula 3 are either commercially available or they can be prepared by methods well known in the art. For examples, butylamine and phenethylamine are commercially available from Aldrich.

Acylation of 4 with a compound of formula 5 where L is a suitable leaving group such as halo, N-methoxy-N-methylamine, and the like provides a compound of formula 6. The reaction is carried out in the presence of a base such as triethylamine, pyridine, and the like and in a chlorinated organic solvent such as dichloromethane, chloroform, and the like. The reaction is typically carried out between 0° C. and 80° C. Preferably, at 23° C. Compounds of formula 5 are either commercially available or they can be prepared by methods well known in the art. For example, compounds of formula 5 where L is chloro can be prepared by treating the corresponding N,N-dialkylamine with an acylating agent such as phosgene, and the like. The reaction is carried out in halogenated solvent such as dichloromethane, chloroform and the like at low temperature e.g., at 0° C. and in the presence of an acid scavenger such as diethyamine.

N,N-dialkylamines such as pyrrolidine, piperidine, piperazine, morpholine, thiomorpholine, homopiperidine, homopiperazine, proline t-butyl ester, pipecolinic acid, 1,2,3,4-tetrahydroquinoline, 1-hydroxyethylpiperazine, 2-hydroxyethylpiperidine, 3-hydroxypiperidine, 4-hydroxypiperidine, and 4-hydroxyproline are commercially available. It will be recognized by a person skilled in the art that if other reactive groups are present in N,N-dialkylamino compound they have to be suitably protected prior to carrying out the chlorination. Examples of suitable protecting groups and their introduction and removal are described in T. W. Greene and G. M. Wuts, "Protecting Groups in Organic Synthesis" Third Ed., Wiley, New York, 1999 and references cited therein.

Compound 6 is then converted to a hydroxamate compound of Formula (I) by treating it with aqueous 50% hydroxylamine in a polar organic solvent such as dioxane and the like. The reaction is carried out at ambient temperature. After the reaction is complete, the resin is filtered, washed with acetonitrile and the filtrates combined and purified by preparative reverse-phase (C18) HPLC to yield compound of Formula (I).

A compound of Formula (I) can be converted to other compounds of Formula (I) by methods well known in the art. Some such methods are described below.

Compounds of Formula (I) containing a hydroxy group may be prepared by de-alkylation/benzylation of an alkyloxy/benzyloxy substituent; and those containing an acid group, by hydrolysis of an ester group. Similarly, a compound of Formula (I) having an alkenyl or alkynyl group can be prepared by reacting a corresponding compound of Formula (I) containing a bromine or iodine atom with trimethylsilylacetylene under the Castro-Stephens reaction conditions. Furthermore, a compound of Formula (I) containing an alkoxy group may be prepared by alkylation of hydroxy substituent. A compound of Formula (I) containing a carboxy group can be prepared by hydrolyzing an ester group in a corresponding compound of Formula (I) under acid hydrolysis reaction conditions. The resulting carboxy group can optionally be converted to an amido group, if desired, by first converting the carboxy group to an activated ester derivative e.g., treating the carboxy compound with dicyclohexyl carbodiimide, diimidazole carbonyl and the like, followed by treatment with an amine. It will be recognized by a person skilled in the art that some of these transformation can be carried out prior to converting the compound of formula 6 to a compound of Formula (I).

Alternatively, a compound of Formula (I) can be prepared as illustrated in Scheme B below.

Scheme B

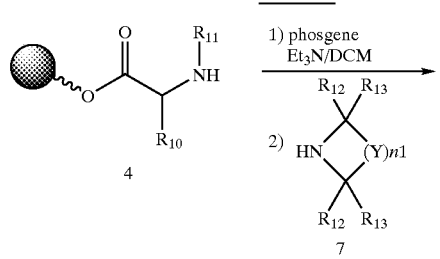

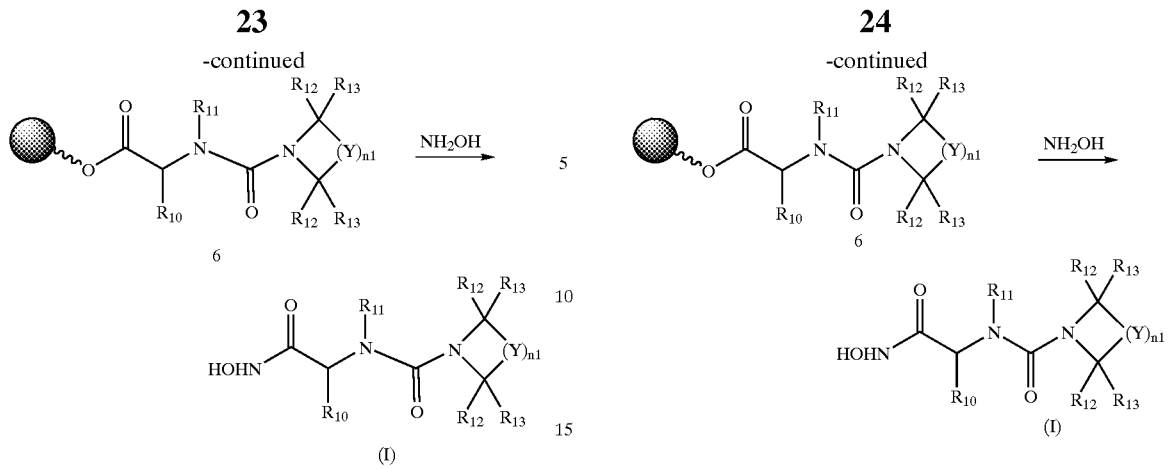

Alternatively, a compound of Formula (I) can be prepared from a compound of formula 4 by acylating it with a suitable acylating agent as described in Scheme A above, followed by treatment of the resulting acylated derivative with an amine of formula 7 to provide a compound of 6 which is then converted to a compound of Formula (I) as described above. Amines of formula 7 such as pyrrolidine, piperidine, piperazine, morpholine, thiomorpholine, homopiperidine, homopiperazine, proline tert-butyl ester, pipecolinic acid, 1,2,3,4-tetrahydroquinoline, 1-hydroxyethylpiperazine, 2-hydroxyethylpiperidine, 3-hydroxypiperidine, 4-hydroxypiperidine, and 4-hydroxyproline are commercially available.

A compound of Formula (I) can also be prepared as illustrated in Scheme C below.

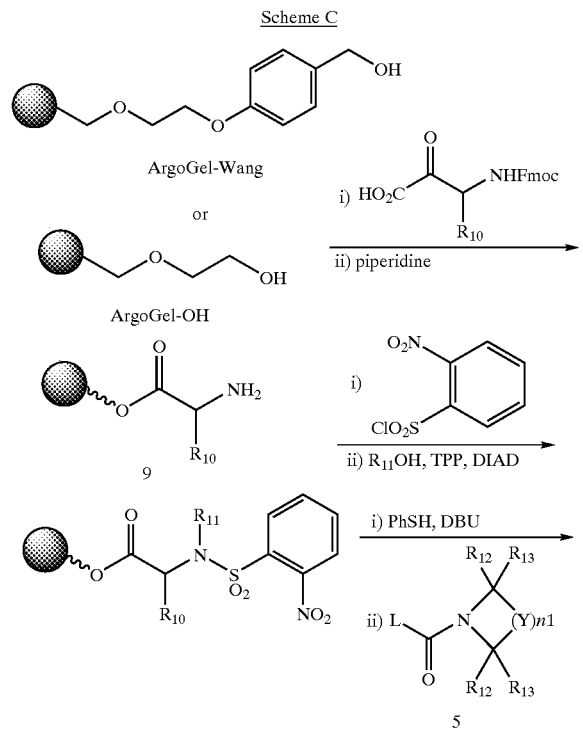

Treatment of a suspension of ArgoGel-Wang or ArgoGel-OH resin with an N-Fmoc-protected amino acid of formula 8 (wherein $R_{10}$ is as defined in the Summary of the Invention) in the presence of a coupling agent such as carbonyldiimidazole and 1-hydroxybenzotriazole, followed by treatment with an amine such as piperidine provides a resin bound amino acid of formula 9. The coupling reaction is carried out in a polar solvent such as dimethylformamide in the presence of a base such as dimethylaminopyridine. The reaction is typically carried out at ambient temperature. Compounds of formula 8 are either commercially available or they can be prepared by methods well known in the art. For example Fmoc-glycine and Fmoc-alanine are commercially available. Others can be prepared from commercially available amino acids as described in T. W. Greene and G. M. Wuts, "Protecting Groups in Organic Synthesis" Third Ed., Wiley, New York, 1999.

Sulfonylation of 9 with 2-nitrophenylsulfonyl chloride, followed by alkylation of the resulting sulfonamido nitrogen provides a compound of formula 10. The sulfonylation reaction is carried out in a chlorinated organic solvent such as dichloromethane, and the like and in the presence of a non-nucleophilic base such as pyridine, 2,4,6-collidine, and the like. The reaction is typically carried out at ambient temperature. The alkylation reaction is carried out in the presence of triphenylphosphine and DIAD (diisopropylazodicarboxylate). DIAD is added after the formation of the triphenylphosphine complex at approximately −78° C. After the addition of DIAD, the reaction temperature is raised to room temperature and stirring is continued till the reaction is complete to provide 10.

Compound 10 was first treated with thiophenol and 1,8-diazabicyclo[4.3.0]undec-7-ene to generate the free amine which upon treatment with a carbomyl halide of formula 5 provides compound 6. Compound 6 is then converted to compounds of Formula (I) as described above.

A compound of Formula (I) can also be prepared as illustrated in Scheme D below.

Scheme D

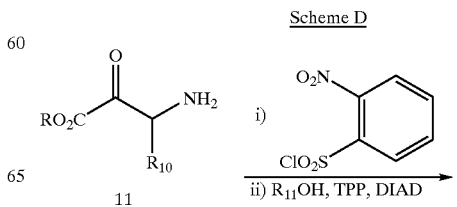

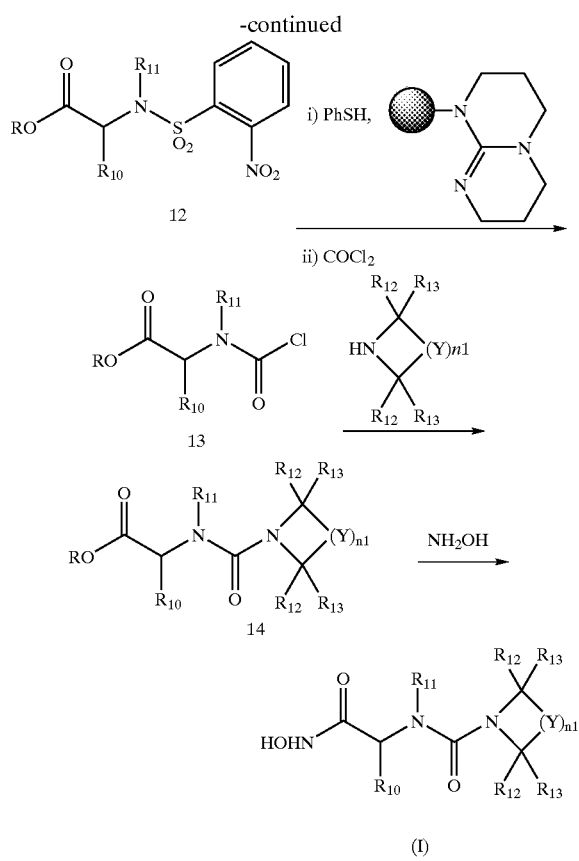

Treatment of an aminoacid ester hydrochloride 11 (where R is alkyl such as methyl, ethyl or tert-butyl) in saturated aqueous base such as $NaHCO_3$ with a solution of 2-nitrobenzenesulfonyl chloride in THF provides a sulfonamido compound which upon treatment with an alcohol of formula $R_{11}OH$ as described above provides a compound of formula 12.

Treatment of 12 with a polymer bound 1,3,4,6,7,8-hexahydro-2H-pyrimidino[1,2-a]pyrimidine (12 mmol) in DMF and thiophenol provides the free amine which is acylated with a suitable acylating agent such as phosgene as described above provides a carbamoyl chloride compound of formula 13. Compound 13 is then converted to a compound of Formula (I) as defined above. Detailed description of a synthesis of a compound of Formula (I) is described in Working Example 36.

Various synthetic methods useful for making compounds of the invention are described herein. Either solid-phase or solution-phase synthesis can be used; solid-phase synthesis provides for convenient separation of intermediates and reagents and is preferred. Resins derivatized with O-protected, N-protected hydroxylamines, such as the resins described in International Patent Application WO 98/18754, provide convenient solid matrixes for support. WO 98/18754 describes resins where the O- and N-protecting groups can be removed orthogonally to each other, that is, removal of one protecting group can be effected under conditions which do not result in removal of the other protecting group.

After preparation of the resin bearing the O-protected, N-protected hydroxylamine, the N-protecting group can then be removed from the resin-bound hydroxylamine moiety. A carboxylic acid-containing compound can then be coupled to the hydroxylamine nitrogen via the carboxylate group to form a hydroxamic acid derivative. Typically, the carboxylic acid-containing compound has additional reactive groups that are protected during the coupling to the hydroxylamine, then deprotected in order to undergo further reaction. The resulting compound is then cleaved from the resin; the O-protecting group can be removed before, during, or after resin cleavage. Purification of the compound can then be effected by methods known in the art, for example high-performance liquid chromatography (HPLC), preparative silica gel columns and other low-pressure chromatography methods, recrystallization of compounds, etc.

Administration, Utility and Testing

Administration and Pharmaceutical Composition

The present invention also provides pharmaceutical compositions which comprise a bioactive hydroxamic acid compound or derivative, or a pharmaceutically acceptable salt thereof, and a pharmaceutically acceptable carrier. The compositions of the invention include those in a form adapted for oral, topical or parenteral use and can be used for the treatment of bacterial infection in animals, preferably mammals, more preferably humans.

The antibiotic compounds, also referred to herein as antimicrobial compounds, according to the invention can be formulated for administration in any convenient way for use in human or veterinary medicine, by analogy with other antibiotics. Such methods are known in the art (see, e.g., *Remington's Pharmaceutical Sciences*, Easton, Pa.: Mack Publishing Co.) and are not described in detail herein.

The composition can be formulated for administration by any route known in the art, such as subdermal, inhalation, oral, topical or parenteral. The compositions can be in any form known in the art, including but not limited to tablets, capsules, powders, granules, lozenges, creams or liquid preparations, such as oral or sterile parenteral solutions or suspensions. The compounds can also be administered in liposome formulations. The compounds can also be administered as prodrugs, where the prodrug administered undergoes biotransformation in the treated mammal to a form which is biologically active.

The topical formulations of the present invention can be presented as, for instance, ointments, creams or lotions, solutions, salves, emulsions, plasters, eye ointments and eye or ear drops, impregnated dressings and aerosols, and can contain appropriate conventional additives such as preservatives, solvents to assist drug penetration and emollients in ointments and creams.

The formulations can also contain compatible conventional carriers, such as cream or ointment bases and ethanol or oleyl alcohol for lotions. Such carriers can be present, for example, from about 1% up to about 99% of the formulation. For example, they can form up to about 80% of the formulation.

Tablets and capsules for oral administration can be in unit dose presentation form, and can contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets can be coated according to methods well known in standard pharmaceutical practice.

Oral liquid preparations can be in the form of, for example, aqueous or oily suspensions, solutions, emulsions, syrups or elixirs, or can be presented as a dry product for reconstitution with water or another suitable vehicle before use. Such liquid preparations can contain conventional additives, such as suspending agents, for example sorbitol, methyl cellulose, glucose syrup, gelatin, hydroxyethyl cellulose, carboxymethyl cellulose, aluminium stearate gel or hydrogenated edible fats; emulsifying agents, for example lecithin, sorbitan monooleate, or acacia; non-aqueous vehicles (which can include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

For parenteral administration, fluid unit dosage forms are prepared utilizing the compound and a sterile vehicle, water being preferred. The compound, depending on the vehicle and concentration used, can be either suspended or dissolved in the vehicle or other suitable solvent. In preparing solutions, the compound can be dissolved in water for injection and filter sterilized before filling into a suitable vial or ampoule and sealing. Advantageously, agents such as a local anesthetic preservative and buffering agents can be dissolved in the vehicle. To enhance the stability, the composition can be frozen after filling into the vial and the water removed under vacuum. The dry lyophilized powder is then sealed in the vial and an accompanying vial of water for injection can be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions can contain, for example, from about 0.1% by weight to about 99% by weight, e.g., from about 10–60% by weight, of the active material, depending on the method of administration. Where the compositions comprise dosage units, each unit will contain, for example, from about 1–500 mg of the active ingredient. The dosage as employed for adult human treatment will range, for example, from about 1 to 3000 mg per day, for instance 1500 mg per day depending on the route and frequency of administration. Such a dosage corresponds to about 0.015 to 50 mg/kg per day. Suitably the dosage is, for example, from about 5 to 20 mg/kg per day.

Utility

The hydroxamate compounds of the present invention can be used for the treatment or prevention of infectious disorders caused by a variety of bacterial or prokaryotic organisms. Examples include Gram positive and Gram negative aerobic and anaerobic bacteria, including Staphylococci, for example *S. aureus* and *S. epeidermidis;* Enterococci, for example *E. faecalis* and *E. faecium;* Streptococci, for example *S. pneumoniae;* Haemophilus, for example *H. influenza;* Moraxella, for example *M. catarrhalis;* and Escherichia, for example *E. coli.* Other examples include Mycobacteria, for example *M. tuberculosis;* intercellular microbes, for example Chlamydia and Rickettsiae; and Mycoplasma, for example *M. pneumoniae.*

In one embodiment, compositions, for treating or preventing infectious disorders are provided, comprising a hydroxamic acid compound or derivative as disclosed herein in combination with a pharmaceutically acceptable carrier.

In another embodiment, there is provided a dosage amount of a hydroxamic acid compound or derivative as disclosed herein in an effective amount for the treatment, prevention or alleviation of a disorder, such as an infectious disorder. Hydroxamic acid compounds or derivatives can be screened for activity against different microbial agents and appropriate dosages can be determined using methods available in the art.

The compounds can be used to treat a subject to treat, prevent, or reduce the severity of an infection. Subjects include animals, plants, blood products, cultures and surfaces such as those of medical or research equipment, such as glass, needles, surgical equipment and tubing, and objects intended for temporary or permanent implantation into an organism. Treating a subject includes, but is not limited to, preventing, reducing, or eliminating the clinical symptoms caused by an infection of a subject by a microorganism; preventing, reducing, or eliminating an infection of a subject by a microorganism; or preventing, reducing, or eliminating contamination of a subject by a microorganism. The microorganism involved is preferably a prokaryote, more preferably a bacterium.

In one embodiment, methods of treating or preventing an infectious disorder in a subject, such as a human or other animal subject, are provided, by administering an effective amount of a hydroxamic acid compound or derivative as disclosed herein to the subject. In one embodiment, the compound is administered in a pharmaceutically acceptable form optionally in a pharmaceutically acceptable carrier. As used herein, an "infectious disorder" is any disorder characterized by the presence of a microbial infection, such as the presence of bacteria. Such infectious disorders include, for example central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients. The compounds and compositions comprising the compounds can be administered by routes such as topically, locally or systemically. Systemic application includes any method of introducing the compound into the tissues of the body, e.g., intrathecal, epidural, intramuscular, transdermal, intravenous, intraperitoneal, subcutaneous, sublingual, nasal, vaginal, rectal, and oral administration. The specific dosage of antimicrobial to be administered, as well as the duration of treatment, can be adjusted as needed.

Representative pharmaceutical formulations containing a compound of Formula (I) are described below.

Testing

The ability of the compounds of this invention to inhibit peptide deformylase was measured by in vitro assay described in detail in Biological Example below. The antimicrobial activity of the compounds of this invention was tested as described in detail in Biological Example 2 below. The selective inhibition of PDF compared to MMP-7 (Matrilysin) by the compounds of this invention was tested as described in detail in Biological Example 3 below.

EXAMPLES

The following preparations and examples are given to enable those skilled in the art to more clearly understand and to practice the present invention. They should not be considered as limiting the scope of the invention, but merely as being illustrative and representative thereof.

Abbreviations

The following abbreviations are used:
AcOH, HOAc=acetic acid
Ac$_2$O=acetic anhydride
BOC, Boc=t-butyloxycarbonyl
DCC=dicyclohexylcarbodiimide
DCM=dichloromethane
DIC=diisopropylcarbodiimide
DIAD=diisopropylazodicarboxylate
DIEA=diisopropylethylamine
DMF=dimethylformamide
EDC=N-(3-Dimethylaminopropyl)-N'-ethylcarbodiimide
Et=ethyl
EtOAc=ethyl acetate
Fmoc, FMOC=9-fluorenylmethyloxycarbonyl
HATU=O-(7-aza-benzotriazol-1-yl)-N,N,N',N'-tetramethyluronium hexafluorophosphate
HBTU=O-(benzotriazol-1-yl)-N,N,N',N'-tetramethyluronium hexafluorophosphate
HHMPA=(4-hydroxymethyl-3-methoxyphenoxy)-alkanoic acid
HMP resin=hydroxymethylphenoxy resin
HOAt=1-hydroxy-7-azabenzotriazole
HOBt=1-hydroxybenzotriazole
Me=methyl
Mem=methoxy ethoxy methyl ether
MeOH=methanol
MMP=matrix metalloproteinase
Mom=methoxy methyl ether
NMM=N-methyl morpholine
NPEOC=4-nitrophenethyloxycarbonyl
NPEOM=4-nitrophenethylmethyloxycarbonyl
NVOC=6-nitroveratryloxycarbonyl
NVOM=nitroveratryloxymethyl ether
PEG-PS resins or PS-PEG resin=polyethylene glycol-polystyrene graft copolymer resins
PFP-OTFA=pentafluorophenyl trifluoroacetate
PyBOP=benzotriazole-1-yl-oxy-tris-pyrrolidinophosphonium hexafluorophosphate
PyBROP=bromotripyrrolidinophosphonium hexafluorophosphate
RT=room temperature
TBP=tributylphosphate
TBS, TBDIMS=t-butyldimethylsilyl
tBu=t-butyl
TES=triethylsilane
TFA=trifluoroacetic acid
TGS resin=TENTAGEL S resin
TGS NH$_2$ resin=TENTAGEL S NH$_2$ resin
THF=tetrahydrofuran
THP=2-tetrahydropyranyl
TMAD=N,N,N',N'-tetramethylazodicarboxamide (1,1'-Azobis(N,N-dimethylformamide))
TMOF=trimethylorthoformate
TPP=triphenyl phosphine
TsCl=tosyl chloride
TsOH=toluenesulfonic acid
Trt=trityl Synthetic Procedures

General Procedure A

Synthesis of ArgoGel-Wang or ArgoGel-OH resin bound 2-bromoacetate 2

Following Scheme A

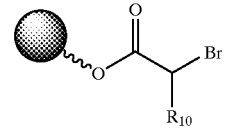

To a suspension of ArgoGel-Wang or ArgoGel-OH resin (20 g, 0.39 mmol/g) and 2,4,6-collidine (30 mL) in DCM (300 mL) at −78° C. was added bromoacetyl bromide 1 (30 mL) dropwise. The ice-bath was removed and the mixture stirred for 40 min, then filtered, washed with MeOH (6×), DCM (2×), and MeOH (2×), and dried to afford ArgoGel-Wang or ArgoGel-OH resin bound bromoacetate 2.

General Procedure B

Synthesis of ArgoGel-Wang or ArgoGel-OH resin bound 2-aminoacetate 4

Following Scheme A

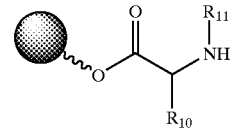

To ArgoGel-Wang or ArgoGel-OH resin bound bromoacetate 2 (0.5 g) was added a solution of amine 3 (2 mmol) in DMF (2 mL). The resin was shaken for 18 h, then drained and washed with DMF (3×), MeOH (3×) and DCM (3×) to give ArgoGel-Wang or ArgoGel-OH resin bound 2-aminooacetate 4.

General Procedure C

Synthesis of ArgoGel-Wang or ArgoGel-OH resin bound 2-ureidoacetate 6

Following Scheme A

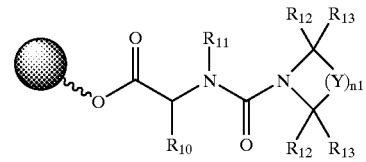

To a solution of phosgene (1 mL, 20% in toluene) in DCM (1 mL) at 0° C. was slowly added a solution of N,N-dialkylamine (1 mmol) and DIEA (0.35 mL, 2 mmol) in DCM (1 mL). The solution was stirred for 15 min and then concentrated to dryness. The solid residue was dissolved in DCM (2 mL), then added to a mixture of ArgoGel-Wang or ArgoGel-OH resin bound 2-aminooacetate 4 (0.5 g) and DIEA (0.2 mL). The suspension was shaken for 24 h, then drained and washed with DCM, methanol and dioxane to afford intermediate ArgoGel-Wang or ArgoGel-OH resin bound 2-ureidoacetate 6.

General Procedure D

Synthesis of N-hydroxy-2-ureidoacetamide (I)

Following Scheme A

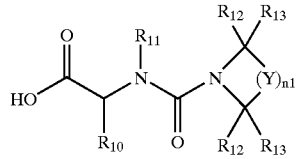

The ArgoGel-Wang or ArgoGel-OH resin bound 2-ureidoacetate 6 (0.25 g) was treated with dioxane (1 mL) and aqueous 50% hydroxylamine (2 mL). After 24 h the resin was filtered, washed with acetonitrile and the filtrates combined and purified by preparative reverse-phase (C18) HPLC to yield product N-hydroxy-2-ureidoacetamide (I).

General Procedure E

Synthesis of N-hydroxy-2-ureidoacetamide (I)

Following Scheme B

A stock solution of triphosgene was prepared from solid triphosgene (1.48 g, 5 mmol) and DCM (20 mL). The solution was cooled to −78° C. and triethylamine (2 mL, 15 mmol) was slowly added. To ArgoGel-Wang or ArgoGel-OH resin bound 2-aminoacetate 4 (0.5 g) was added the triphosgene solution (3.5 mL) and the resin was shaken at rt for 1 h. The resin was drained, washed with DCM (3×) and then suspended in a solution of secondary amine 7 (e.g., pyrrolidine, 2 mmol) and TEA (3 mmol) in DCM (2 mL). After 16 h, the resin was washed with DCM and MeOH (3× each) to yield ArgoGel-Wang or ArgoGel-OH resin bound 2-ureidoacetate 6 which was then treated with a solution of aqueous 50% hydroxylamine (2 mL) and dioxane (1 mL) for 2 days. The resin was filtered, washed with acetonitrile and the filtrates combined and purified by preparative reverse-phase (C18) HPLC to yield product N-hydroxy-2-ureidoacetamide (I).

General Procedure F

Following Scheme C

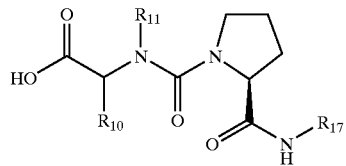

Step 1

To ArgoGel resin (0.46 mmol/g, 9.2 mmol) in DMF (150 mL) was added an Fmoc-protected aminoacid 8 (46 mmol), HOBt (46 mmol) and DMAP (0.46 mmol) and the suspension shaken for 5 min. DIC (46 mmol) was then added in three portions over 10 min, and the resulting suspension shaken 48 h. The reaction was drained, washed with DMF (3×200 mL), DCM/DMF 1:1 (3×200 mL), DCM (3×200 mL), MeOH (3×200 mL), Et$_2$O (2×200 mL) and then dried in vacuo. Fmoc quantitation determined a substitution of 0.35 mmol/g for the resin product. The resin was then treated with 20% piperidine in DMF for 5 min., drained, and then a second aliquot of 20% piperidine in DMF was added. After 20 min., the resin was drained and then washed with DMF (3×200 mL), DCM/DMF 1:1 (3×200 mL), DCM (3×200 mL) to afford an ArgoGel resin bound aminoacetate 9.

Step 2

To ArgoGel resin bound aminoacetate 9 was added 2-nitrobenzenesulfonyl chloride (46 mmol) in DCM (20 mL) and 2,4,6 collidine (46 mmol). The suspension was shaken until a negative Kaiser test was obtained (approximately 4 h), then drained, washed as described in the first reaction step, and then dried over P$_2$O$_5$ in vacuo. To an aliquot of this sulfonamide intermediate (0.4 mmol) was added an alcohol (4.4 mmol) and a solution of triphenylphosphine (2.6 mmol) in THF (4 mL). The suspension was cooled to −78° C., DIAD (2.6 mmol) in THF (2 mL) was added with agitation, and the reaction mixture warmed to room temperature over 20 minutes. After 18 h the solvent and reagents were removed by filtration and the resin was washed as described to afford resin bound N-alkylsulfonamide 10.

Step 3

Resin bound N-alkylsulfonamide 10 (0.40 mmol) was suspended in a DMF solution of 1.8 M thiophenol and 0.9 M DBU (12 mL) and the reaction mixture shaken for 25 minutes. The suspension was drained, then washed with DMF (4×20 mL), DCM/DMF 1:1 (2×20 mL), DCM (3×20 mL), and Et$_2$O (2×20 mL). To the resulting resin-bound secondary amine was added N-chlorocarbamoyl-2-t-butyl ester L-proline 5 (6.2 mmol; prepared from H-Pro-O-t-Bu and phosgene) in DCM/pyridine 1:1 (10 mL). The suspension was shaken for 16 h, drained, and then washed with DCM (3×20 mL), DCM/MeOH 9:1 (3×20 mL), DCM (3×20 mL), and Et$_2$O (2×20 mL) to afford the resin bound 2-[(2-tert-butoxycarbonyl-pyrrolidin-1-carbonyl)amino]acetate. This intermediate was treated with TFA/DCM 1:2 (15 mL) for 40 minutes, then drained and washed with DCM (4×20 mL), Et$_2$O (3×20 mL), and DCM (2×20 mL) to afford resin bound 2-[(2-carboxypyrrolidin-1-carbonyl)amino]acetate 6.

Step 4

To resin bound 2-[(2-carboxypyrrolidin-1-carbonyl) amino]acetate 6 (0.40 mmol) suspended in DMF (2 mL) was added an amine (2 mmol), DIEA (5 mmol) and DMAP (0.2 mmol) followed by a solution of PyBop (3 mmol) in DCM (3 mL). The suspension was shaken for 12 h, then drained and washed with DCM (3×20 mL), DCM/MeOH 9:1 (3×20 mL), DCM (3×20 mL), Et$_2$O (2×20 mL), and dioxane (2×20 mL). The resin was then suspended in a 50% aqueous solution of hydroxylamine in dioxane 1:2 (3 mL) and shaken for 24 h. The filtrate was collected and purified on preparative reverse phase (C18) HPLC to afford N-hydroxy-2-[(2-amidopyrrolidin-1-carbonyl)amino]acetamide.

General Procedure G

Following Scheme D

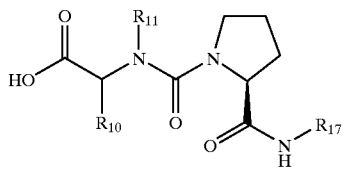

Step 1

To an amino acid methyl ester hydrochloride 11 (R is methyl) (88 mmol) in saturated aqueous NaHCO$_3$ (25 mL) was added with vigorous stirring a solution of 2-nitrobenzene-sulfonyl chloride (77 mmol) in THF (50 mL). Additional NaHCO$_3$ was added over 2 h to maintain a basic pH. The reaction mixture was then extracted with DCM (500 mL) and the organic layer washed with water, dried (Na$_2$SO$_4$), concentrated, and the crude product recrystallized from 2:1 water/isopropanol then dried over P$_2$O$_5$ in vacuo to provide N-2-nitrophenylsulfonyl aminoacid methyl ester hydrochloride as colorless crystals (72%). To a 0° C. solution of N-2-nitrophenylsulfonyl aminoacid methyl ester hydrochloride (28 mmol), an alcohol (25 mmol) and triphenylphosphine (28 mmol) in THF (10 mL) was slowly added DIAD (28 mmol) over 5 minutes. The reaction was allowed to warm to rt then stirred additional 24 h. The solvent was removed and the crude product purified on silica gel (Merck 60; hexanes/DCM/THF 12:6:1) to afford 22 mmol of N-2-nitrophenylsulfonyl-N-alkyl-aminoacid methyl ester hydrochloride 12 (87%).

Step 3

To a stirred suspension of N-2-nitrophenylsulfonyl-N-alkyl-aminoacid methyl ester hydrochloride 12 (11 mmol) and polymer bound 1,3,4,6,7,8-hexahydro-2H-pyrimidino[1,2-a]pyrimidine (12 mmol) in DMF (40 ml) was added thiophenol (22 mmol). After 1 hour the reaction mixture was diluted with ether (300 mL), filtered, and the filtrate washed with brine (5×50 mL) and saturated NaHCO$_3$ (50 mL). The combined basic aqueous washes were then back extracted with DCM (2×50 mL) and the DCM layers combined. The ether phase was then extracted with 0.5 M HCl (5×25 mL), the aqueous extract was made basic with solid NaHCO$_3$, then saturated with NaCl and extracted with (5×50 mL) DCM. All DCM layers were combined, dried (Na$_2$SO$_4$), acidified with 4N HCl in dioxane and evaporated to provide the secondary amine hydrochloride salt. In a separate flask, phosgene (20% in toluene; 0.11 mol) was added to a vigorously stirred 0° C. suspension of NaHCO$_3$ (1 mole) in water (125 mL) and ether (200 mL). To this was added dropwise over 30 minutes the secondary amine HCl salt in water (125 mL) and an additional aliquot of phosgene (0.11 mol). The reaction mixture was allowed to warm to rt then stirred an additional 15 minutes. The phases were separated and the organic phase washed with 1M HCl (2×75 mL), brine (75 mL), dried (MgSO$_4$), and evaporated to provide N-alkyl-aminoacid methyl ester carbamoyl chloride 13 (10 mmol) 91% (2 steps).

Step 4

An aliquot of N-alkyl-aminoacid methyl ester carbamoyl chloride 13 (4 mmol) dissolved in DCM (4 mL) was added to a 0° C. solution of proline t-butyl ester (5.3 mmol) in pyridine (4 mL). After 30 min., the reaction mixture was diluted with ether (100 mL), washed with 10% KHSO$_4$ (2×25 mL), brine (25 mL), dried (NaSO$_4$) and evaporated to provide 3.5 mmol of the desired urea. To the urea was added 1:1 TFA/DCE (50 mL) and the solution stirred for 45 minutes. The reaction was evaporated to dryness, then co-evaporated twice from DCE (10 mL) to provide N-[(2-carboxypyrrolidin-1-carbonyl)amino]aminoacid methyl ester 14 (88% for two steps).

Step 5

To N-[(2-carboxypyrrolidin-1-carbonyl)amino]aminoacid methyl ester 14 (200 μmol) in dioxane (2 mL) was added an amine (200 μmol), DIEA (500 μmol) and HATU (200 μmol) and the reaction stirred for 8 h. The solution was diluted with 50% aqueous hydroxylamine (1 mL), and the reaction stirred for 24–36 h. The crude reaction mixture was then purified by preparative reverse-phase (C18) HPLC to afford N-hydroxy-2-[(2-amidopyrrolidin-1-carbonyl)amino]acetamide.

Example 1

Synthesis of N-hydroxy-2-[N-butyl-N-(2-(S)-tert-butoxycarbonyl)pyrrolidin-1-carbonyl)amino]acetamide

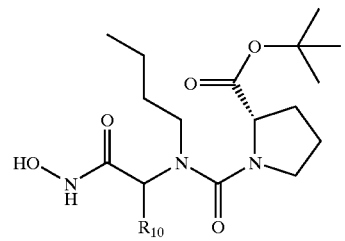

The above compound was prepared according to General Procedures A-D from n-butylamine and L-proline tert-butyl ester. $^1$H NMR (300 MHz, CDCl$_3$) δ0.84 (t, J=7.5 Hz, 3H), 1.22 (hex, J=7.5 Hz, 2H), 1.37 (s, 9H), 1.40–1.60 (m, 2H), 1.67–1.84 (m, 2H), 1.47–1.84 (m, 2H), 1.85–1.99 (m, 1H), 2.12–2.22 (m, 1H), 3.09–3.17 (m, 2H), 3.37–3.45 (m, 1H), 3.72 (d, J=2.4 Hz, 2H), 4.26 (t, J=6.9 Hz, 1H).

Example 2

Synthesis of N-hydroxy-2-[N-butyl-N-(2-(S)-methoxymethyl)pyrrolidin-1-carbonyl)amino]acetamide

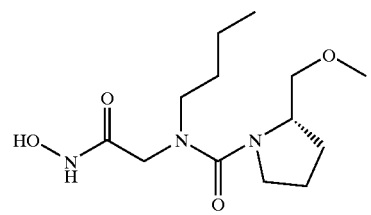

The above compound was prepared according to General Procedures A, B and E from n-butylamine and (S)-(+)-2-(methoxymethyl)pyrrolidine. $^1$H NMR (300 MHz, CDCl$_3$) δ0.92 (t, J=6.3 Hz, 3 H), 1.22–1.36 (m, 2H), 1.45–1.83 (m, 2H), 1.86–2.13 (m, 2H), 3.06–3.29 (m, 2H), 3.3 (s, 3H), 3.38–3.45 (m, 2H), 3.77 (d, J=16.2 Hz, 1 H), 3.93 (d, J=16.2 Hz, 1 H), 4.23 (m, 1 H).

Example 3

Synthesis of N-hydroxy-2-[N-butyl-N-(2-(S)-tert-butylaminocarbonyl)pyrrolidin-1-carbonyl)amino]acetamide

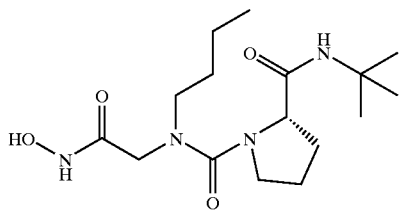

The above compound was prepared according to General Procedures A, B and E from n-butylamine and L-proline t-butyl amide. $^1$H NMR (300 MHz, CDCl$_3$) δ0.92 (t, J=7.5 Hz, 3 H), 1.24–1.37 (m, 4H), 1.34 (s, 9H), 1.47–1.67 (m, 2H), 1.74–1.90 (m, 1H), 1.95–2.08 (m, 2H), 2.11–2.25 (m, 1H), 3.15–3.35 (m, 2H), 3.39–3.57 (m, 2H), 3.79 (d, J=17.1 Hz, 1H), 3.93 (d, J=17.1 Hz, 1 H), 4.32 (m, 1H), 6.06 (s, 1H).

Example 4

Synthesis of N-hydroxy-2-[N-(2-cyclohex-1-enylethyl)-N-(2-(S)-tert-butoxycarbonyl)pyrrolidin-1-carbonyl)amino]acetamide

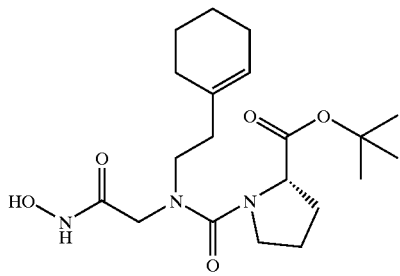

The above compound was prepared according to General Procedures A, B and E from 2-(1-cyclohexenyl)ethylamine and L-proline tert-butyl ester. $^1$H NMR (300 MHz, CDCl$_3$) δ1.11 (t, J=7.1 Hz, 3H), 1.15–1.22 (m, 4H), 1.49–1.66 (m, 4H), 1.87–2.02 (m, 2H), 3.09–3.26 (m, 4H), 3.82 (s, 3H), 5.45 (s, 1H).

Example 5

Synthesis of N-hydroxy-2-[N-(2-(2-fluorophenyl)ethyl)-N-(2-(S)-tert-butoxycarbonyl)pyrrolidin-1-carbonyl)amino]acetamide

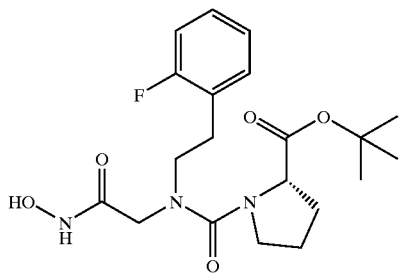

The above compound was prepared according to General Procedures A, B and E from 2-fluorophenethylamine and L-proline tert-butyl ester. $^1$H NMR (300 MHz, CDCl$_3$) δ1.45 (s, 9H), 1.77–2.09 (m, 3H), 2.20–2.34 (m, 1H), 2.88–3.05 (m, 2H), 3.35–3.62 (m, 4H), 3.87–3.99 (m, 2H), 4.33–4.41 (m, 1H), 6.98–7.13 (m, 2H), 7.18–7.28 (m, 2H).

Example 6

Synthesis of N-hydroxy-2-[N-(3-ethoxypropyl)-N-(2-(S)-tert-butoxycarbonyl)pyrrolidin-1-carbonyl)amino]acetamide

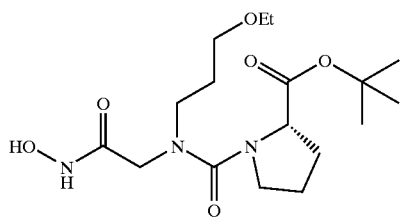

The above compound was prepared according to General Procedures A, B and E from 3-ethoxypropylamine and L-proline t-butyl ester. $^1$H NMR (300 MHz, CDCl$_3$) δ1.20 (t, J=6.0 Hz, 3H), 1.45 (s, 9H), 1.79–2.08 (m, 6H), 2.19–2.32 (m, 1H), 3.21–3.56 (m, 8H), 3.85 (d, J=16.2 Hz, 1 H), 3.94 (d, J=16.2 Hz, 1 H), 4.37 (t, J=6 Hz, 1H).

Example 7

Synthesis of N-hydroxy-2-[N-butyl-N-(2-(R)-tert-butoxycarbonyl)piperidin-1-carbonyl)amino]acetamide

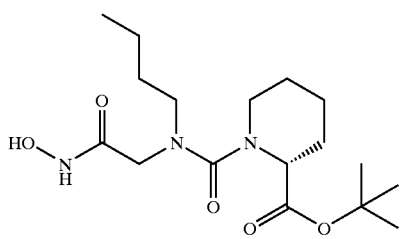

The above compound was prepared according to General Procedures A, B and E from n-butylamine and D-homoproline t-butyl ester. MS (APCI) m/z 358 [M+H].

Example 8

Synthesis of N-hydroxy-2-[N-(2-thiophen-2-ylethyl)-N-(2-(S)-tert-butoxycarbonyl)pyrrolidin-1-carbonyl)amino]acetamide

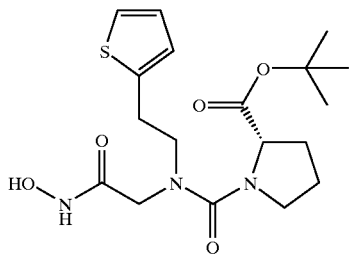

The above compound was prepared according to General Procedures A, B and E from 2-(2-thiophene)ethylamine and L-proline t-butyl ester. MS (APCI) m/z 398 [M+H].

Example 9

Synthesis of N-hydroxy-2-[N-(2-cyclohexylethyl)-N-(2-(S)-tert-butoxycarbonyl)pyrrolidin-1-carbonyl)amino]acetamide

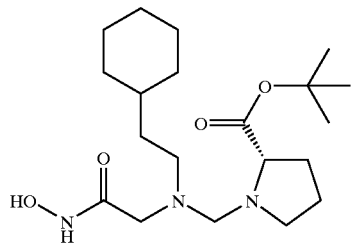

The above compound was prepared according to General Procedures A, B and E from 2-cyclohexane-1-aminoethane and L-proline t-butyl ester. MS (APCI) m/z 398 [M+H].

Example 10

Synthesis of N-hydroxy-2-[N-(napth-1-ylmethyl)-N-(2-(S)-tert-butoxycarbonyl)pyrrolidin-1-carbonyl)amino]acetamide

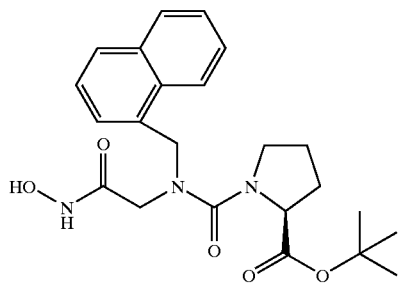

The above compound was prepared according to General Procedures A, B and E from 1-aminomethyl-naphthalene and L-proline t-butyl ester. MS (APCJ) m/z 428 [M+H].

Example 11

Synthesis of N-hydroxy-2-[N-(4-fluorobenzyl)-N-(2-(S)-tert-butoxycarbonyl)pyrrolidin-1-carbonyl)amino]acetamide

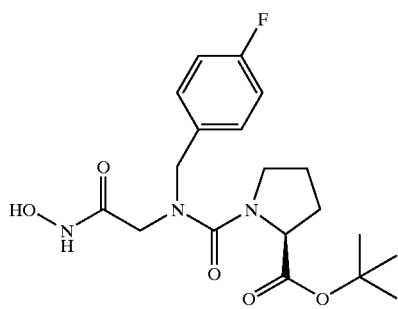

The above compound was prepared according to General Procedures A, B and E from 4-fluorobenzylamine and L-proline t-butyl ester. MS (APCJ) m/z 396 [M+H].

Example 12

Synthesis of N-hydroxy-2-[N-(2-ethylthioethyl)-N-(2-(S)-tert-butoxycarbonyl)pyrrolidin-1-carbonyl)amino]acetamide

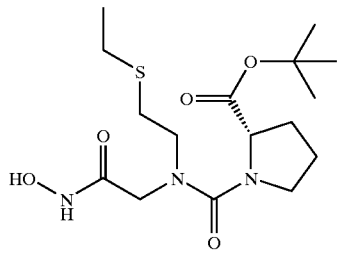

The above compound was prepared according to General Procedures A, B and E from 2-(mercaptoethyl)-ethylamine and L-proline t-butyl ester. MS (APCI) m/z 376 [M+H].

Example 13

Synthesis of N-hydroxy-2-[N-(2(4-chlorophenyl)ethyl)-N-(2-(S)-tert-butoxycarbonyl)pyrrolidin-1-carbonyl)amino]acetamide

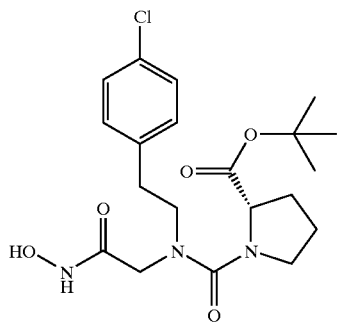

The above compound was prepared according to General Procedures A, B and E from 4-chlorophenethylamine and L-proline t-butyl ester. MS (APCI) m/z 426 [M+H].

Example 14

Synthesis of N-hydroxy-2-[N-(2-cyclohex-1-enylethyl)-N-(2-(S)-methylaminocarbonyl)pyrrolidin1-carbonyl)amino]acetamide

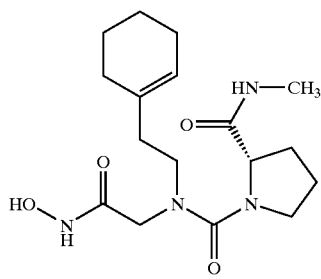

The above compound was prepared according to General Procedures A, B and E from 2-(cyclo-1-hexenyl)-ethylamine and L-proline methylamide. MS (APCI) m/z 353 [M+H].

Example 15

Synthesis of N-hydroxy-2-[N-(butyl)-N-(2-(S)-4-benzylpiperazin-1-ylcarbonyl)pyrrolidin-1-carbonyl)amino]acetamide

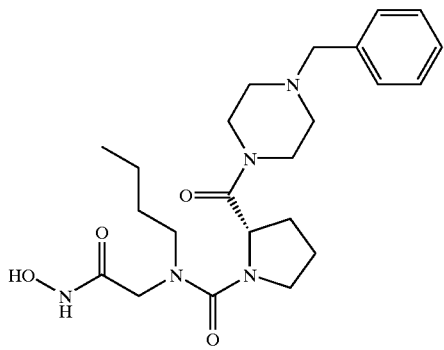

The above compound was prepared according to General Procedures A, B and E from n-butylamine and L-proline N-benzylpiperazineamide. MS (APCI) m/z 446 [M+H].

Example 16

Synthesis of N-hydroxy-2-[N-(pentyl)-N-(2-(S)-tert-butoxycarbonyl)pyrrolidin-1-carbonyl)amino]acetamide

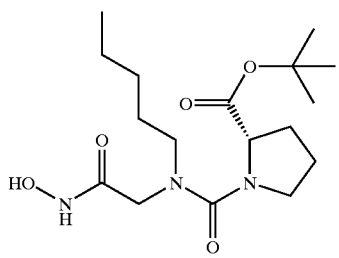

The above compound was prepared according to General Procedures A, B and E from n-pentylamine and L-proline t-butyl ester. MS (APCI) m/z 358 [M+H].

Example 17

Synthesis of N-hydroxy-2-[N-(3-methylbutyl)-N-(2-(S)-tert-butoxycarbonyl)pyrrolidin-1-carbonyl)amino]acetamide

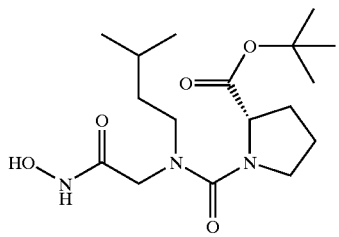

The above compound was prepared according to General Procedures A, B and E from 3-methyl-n-butylamine and L-proline t-butyl ester. MS (APCI) m/z 358 [M+H].

Example 18

Synthesis of N-hydroxy-2-[N-(butyl)-N-(2-(S)-piperidin-1-ylcarbonyl)pyrrolidin-1-carbonyl)amino]acetamide

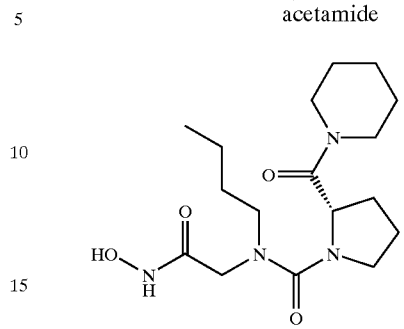

The above compound was prepared according to General Procedures A, B and E from n-butylamine and L-proline piperidineamide. MS (APCI) m/z 355 [M+H].

Example 19

Synthesis of N-hydroxy-2-[N-(2-cyclohex-1-ylethyl)-N-(3-(S)-tert-butoxycarbonylamino)pyrrolidin-1-carbonyl)amino]acetamide

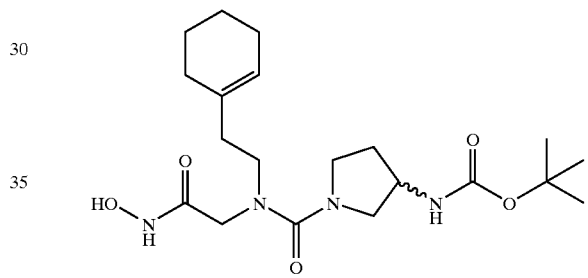

The above compound was prepared according to General Procedures A, B and E from 2-(cyclo-1-hexenyl)-ethylamine and (±)-(3-t-butoxycarbonylamino)pyrrolidine. MS (APCI) m/z 411 [M+H].

Example 20

Synthesis of N-hydroxy-2-[N-(2-(2-fluorophenyl)ethyl)-N-(2-(S)-phenylamino-carbonyl)pyrrolidin-1-carbonyl)amino]acetamide

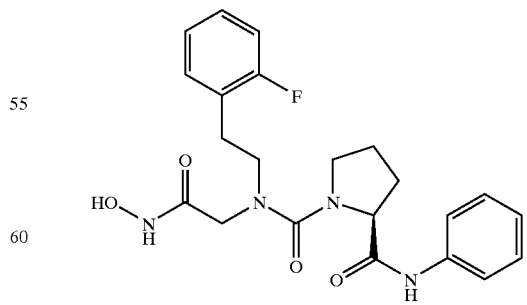

The above compound was prepared according to General Procedures A, B and E from o-fluorophenethylamine and L-proline anilineamide. MS (APCI) m/z 429 [M+H].

Example 21

Synthesis of N-hydroxy-2-[N-(2-(thien-2-yl)ethyl)-N-(2-(S)-phenylamino-carbonyl)pyrrolidin-1-carbonyl)amino]acetamide

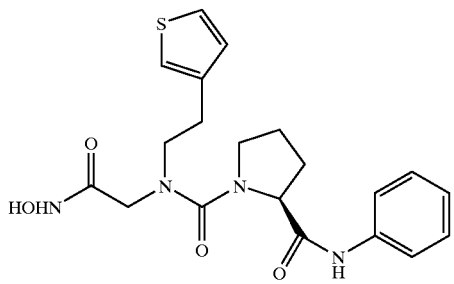

The title compound was prepared according to General Procedure F from glycine, 2-(3-thienyl)ethanol, and aniline. $^1$H NMR (DMSO-d6): δ7.68 (d, J=8.5, 2H), 7.64–7.34 (m, 1H), 7.28 (dd, J=7.4, 7.4, 2H), 7.20–7.18 (m, 1H), 7.05–6.99 (m, 2H), 4.42 (dd, J=7.7, 7.7, 1H), 3.94 (d, J=16.2, 1H), 3.64 (d, J=16.2, 1H), 3.55–3.43 (m, 3H), 3.30–3.23 (m, 1H), 2.84 (dd, J=8.0, 8.0, 2H), 2.22 (br s, 1H), 1.93 (br s, 1H), 1.81–1.64 (m, 2H). ES–MS: calcd. for $C_{20}H_{24}N_4O_4S$ (416.15); found: 415.6 [M−1].

Example 22

Synthesis of N-hydroxy-2-[N-(2-(2-fluorophenyl)ethyl)-N-(2-(S)-methylamino-carbonyl)pyrrolidin-1-carbonyl)amino]acetamide

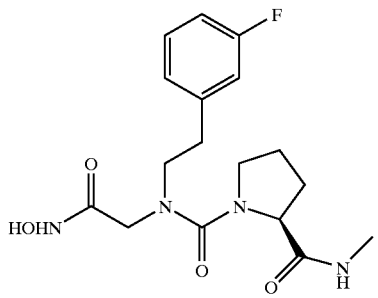

The title compound was prepared according to General Procedure F from glycine, 3-fluorophenethyl alcohol, L-proline, and methylamine. $^1$H NMR (DMSO-d6): δ7.70–7.68 (m, 1H), 7.27 (dd, J=7.7, 14.6, 1H), 7.05–6.94 (m, 3H), 4.22 (dd, J=8.2, 8.2, 1H), 3.85 (d, J=16.5, 1H), 3.56 (d, J=16.5, 1H), 3.47–3.38 (m, 2H), 3.33–3.28 (m, 2H), 3.17–3.08 (m, 1H), 2.83–2.73 (m, 2H), 2.51 (d, J=4.4, 3H), 2.07 (br s, 1H), 1.76 (br s, 1H), 1.63–1.53 (m, 2H); ES–MS: calcd. for $C_{17}H_{23}FN_4O_4$ (366.2); found: 365.5 [M−H].

Example 23

Synthesis of N-hydroxy-2-[N-(2-phenylethyl)-N-(2-(S)-butylaminocarbonyl)pyrrolidin-1-carbonyl)amino]acetamide

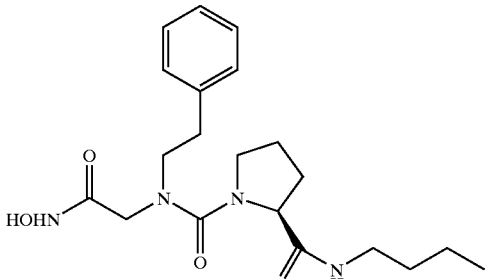

The title compound was prepared according to General Procedure F from glycine, phenethylalcohol and butylamine. $^1$H NMR (DMSO-d6): δ7.74–7.72 (m, 1H), 7.32–7.17 (m, 4H), 4.26 (dd, J=8.2, 8.2, 1H), 3.90 (d, J=16.5, 1H), 3.65 (d, J=16.5, 1H), 3.51–3.37 (m, 3H), 3.25–3.15 (m, 1H), 3.02 (br s, 2H), 2.78 (br s, 2H), 2.12 (br s, 1H), 1.81(br s, 1H), 1.80–1.52 (m, 2H), 1.36 (dd, J=7.1, 12.9, 2H), 1.24 (dd, J=7.7, 15.1, 2H), 1.53 (t, J=7.1, 3H); ES–MS: calcd. for $C_{20}H_{30}N_4O_4$ (390.23); found: 389.5 [M−H].

Example 24

Synthesis of N-hydroxy-2-[N-(2-(4-methylthiazol-5-yl)ethyl)-N-(2-(S)-phenylaminocarbonyl)pyrrolidin-1-carbonyl)amino]acetamide

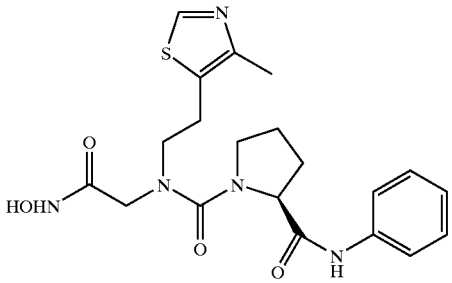

The title compound was prepared according to General Procedure F from 4-methyl-5-thiazole-ethanol, glycine and aniline. $^1$H NMR (DMSO-d6): δ9.07 (s, 1H), 7.88 (d, J=8.5, 2H), 7.47 (dd, J=7.7, 7.7, 2H), 7.25–7.20 (m, 2H), 4.62 (dd, J=8.0, 8.0, 1H), 4.16 (d, J=16.8, 1H), 3.91 (d, J=16.8, 1H), 3.70–3.63 (m, 3H), 3.37–3.30 (m, 1H), 3.22 (dd, J=7.1, 7.1, 2H), 2.69 (s, 3H), 2.43 (br s, 1H), 2.13 (br s, 1H), 2.03–1.85 (m, 1H); ES–MS: calcd. for $C_{20}H_{25}N_5O_4S$ (431.2); found: 430.6 [M−1].

Example 25

Synthesis of N-hydroxy-2-[N-(2-(thiophen-3-yl)ethyl)-N-(2-(S)-pyridin-3-ylaminocarbonyl)pyrrolidin-1-carbonyl)amino]acetamide

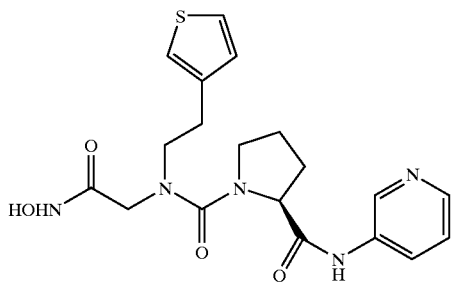

The title compound was prepared according to General Procedure F from glycine, 2-(3-thienyl)ethanol, and 3-amino pyridine. ES–MS: calcd. for $C_{19}H_{23}N_5O_4S$ (417.15); found: 418.6 [M+1].

Example 26

Synthesis of N-hydroxy-2-[N-(3-methylbutyl)-N-(2-(S)-3-methylbutyl-aminocarbonyl)pyrrolidin-1-carbonyl)amino]acetamide

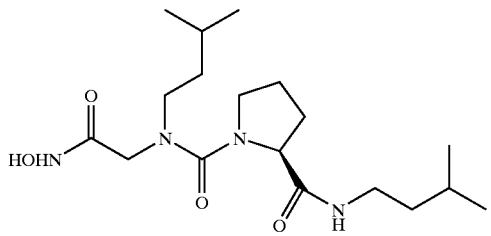

The title compound was prepared according to General Procedures F and G from glycine, 3-methyl-1-butanol, and 3-methy-1-butylamine. $^1$H NMR (DMSO-d6): δ7.88–6.85 (dd, J=5.5 Hz, 1H), 4.46–4.40 (dd, J=8.0 Hz, 1H), 4.07–4.02 (d, J=16.5 Hz, 1H), 3.83–3.77 (d, J=16.5 Hz, 1H), 3.59–3.54 (m, 2H), 3.40–3.17 (m, 4H), 2.30–2.27 (m, 1H), 2.00 (m, 1H), 1.87–1.61 (m, 4H), 1.58–1.54 (m, 2H), 1.50–1.43 (dd, J=7.14 Hz, 1H), 1.06–1.02(m, 12H); ES–MS: calcd. for $C_{18}H_{34}N_4O_4$ (370.3); found: 393.5 [M+Na].

Example 27

Synthesis of N-hydroxy-2-[N-(3-methylbutyl)-N-(2-(S)-phenylaminocarbonyl)pyrrolidin-1-carbonyl)amino]acetamide

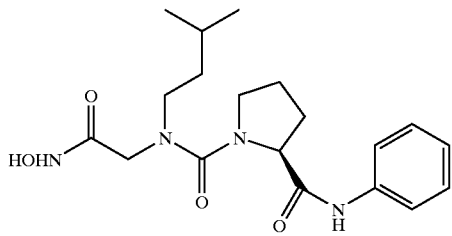

The title compound was prepared according to General Procedures F and G from glycine, 3-methyl-1-butanol, and aniline. $^1$H NMR (DMSO-d6): δ7.86 (dd, J=1.1, 8.2, 2H), 7.47 (ddd, J=1.9, 7.4, 7.4, 2H), 7.21 (ddd, J=1.1, 8.5, 8.5, 1H), 4.60 (dd, J=7.4, 7.4, 1H), 4.11 (d, J=16.5, 1H), 3.79 (d, J=16.5, 1H), 3.66 (m, 2H), 3.45 (ddd, J=7.4, 7.4, 14.0, 2H), 3.21 (ddd, J=7.4, 7.4, 14.6, 2H), 2.40 (m, 1H), 2.11 (m, 1H), 1.94 (m, 2H), 1.67 (ddd, J=6.4, 12.9, 19.2, 1H), 1.58 (dd, J=7.4, 7.4, 2H), 1.04 (d, J=6.3, 3H), 1.03 (d, J=6.3, 3H). ES–MS: calcd. for $C_{19}H_{28}N_4O_4$ (376.2); found: 375.5 [M–1].

Example 28

Synthesis of N-hydroxy-2-[N-(4-methylpentyl)-N-(2-(S)-phenylamino-carbonyl)pyrrolidin-1-carbonyl)amino]acetamide

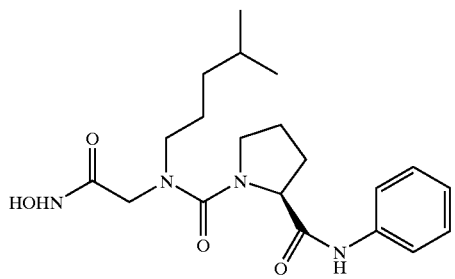

The title compound was prepared according to General Procedure F from glycine, 4-methyl-1-pentanol and aniline. ES–MS: calcd. for $C_{20}H_{30}N_4O_4$ (390.2); found: 389 [M–1].

Example 29

Synthesis of N-hydroxy-2-[N-(2-(thiophen-3-yl)ethyl)-N-(2-(S)-tert-butoxycarbonyl)pyrrolidin-1-carbonyl)amino]acetamide

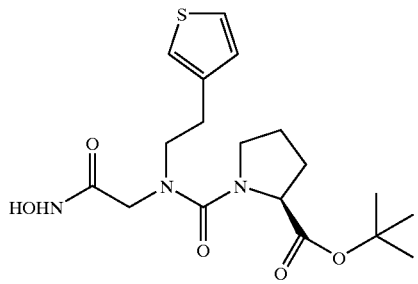

The title compound was prepared according to General Procedure F from glycine and 2-(3-thienyl)ethanol, except the TFA deprotection of the t-butyl ester was ommitted. $^1$H NMR (DMSO-d6): δ7.66–7.64 (m, 1H), 7.39–7.38 (m, 1H), 7.20–7.17 (m, 1H), 4.38 (dd, J=7.4, 1H), 3.98 (d, J=16.5, 1H), 3.79 (d, J=16.5, 1H), 3.61–3.43 (m, 4H), 3.05 (dd, J=7.7, 7.7, 2H), 2.35–2.30 (m, 1H), 2.08–1.99 (m, 1H), 1.96–1.84 (m, 2H), 1.56 (s, 9H). ES–MS: calcd. for $C_{18}H_{27}N_3O_5S$ (397.2); found: 396 [M–1].

Example 30

Synthesis of N-hydroxy-2-[N-(3-methylbutyl)-N-(2-(S)-indan-5-ylamino-carbonyl)pyrrolidin-1-carbonyl)amino]acetamide

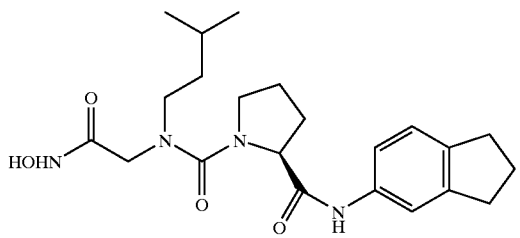

The title compound was prepared according to General Procedure F from glycine, 3-methyl-1-butanol, and 6-aminoindan. $^1$H NMR (DMSO-d6): δ7.77 (s, 1H), 7.55 (d, J 8.0, 1H), 7.29 (d, J=8.0, 1H), 4.58 (dd, J=7.4, 7.4, 1H), 4.09 (d, J=16.5, 1H), 3.79 (d, J=16.5 1H), 3.49–3.39 (m, 1H), 3.27–3.20 (m, 1H), 2.99 (dd, J=6.9, 13.5, 4H), 2.39 (br s, 1H), 2.22–2.10 (m, 3H), 2.05–1.83 (m, 2H), 1.72–1.56 (m, 3H), 1.04 (dd, J=6.3, 6.3, 6H). ES–MS: calcd. for $C_{22}H_{32}N_4O_4$ (416.15); found: 415.6 [M–H].

Example 31

Synthesis of N-hydroxy-2-[N-(4-methylpentyl)-N-(2-(S)-3-methylbutylamino-carbonyl)pyrrolidin-1-carbonyl)amino]acetamide

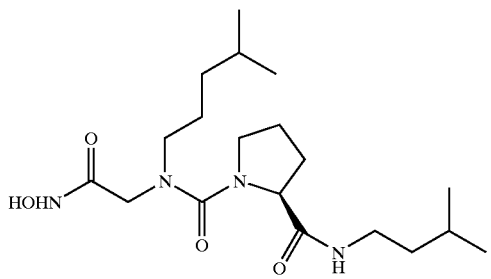

The title compound was prepared according to General Procedure F from glycine, 4-methyl-1-pentanol, and 3-methy-butyl amine. $^1$H NMR (DMSO-d6): δ7.86–7.84 (m, 1H), 4.43 (dd, J=8.0, 8.0, 1H), 4.05 (d, J=16.5, 1H), 3.00 (d, J=16.5, 1H), 3.60–3.54 (m, 2H), 3.33–3.15 (m, 4H), 2.30 (br s, 1H), 2.00 (br s, 1H), 1.90–1.64 (m, 6H), 1.47 (dd, J=7.1, 14.0, 2H), 1.26 (d, J=6.9, 14.0, 2H), 1.04 (d, J=6.6, 3H), 1.03 (d, J=6.6, 3H). ES–MS: calcd. for $C_{19}H_{36}N_4O_4$ (384.3); found: 383 [M–1].

Example 32

Synthesis of N-hydroxy-2-[N-(3,3-dimethylbutyl)-N-(2-(S)-3-methylbutyl-aminocarbonyl)pyrrolidin-1-carbonyl)amino]acetamide

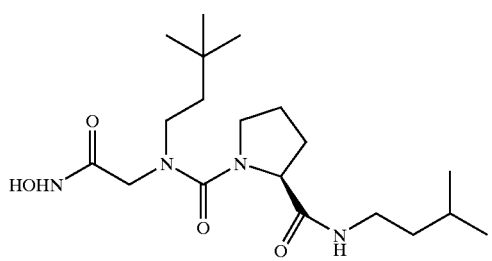

The title compound was prepared according to General Procedure F from glycine, 3,3-dimethylbutanol, and 3-methy-butyl amine. $^1$H NMR (DMSO-d6): δ7.86–7.84 (m, 1H), 4.43 (dd, J=8.0, 8.0, 1H), 4.05 (d, J=16.5, 1H), 3.00 (d, J=16.5, 1H), 3.60–3.54 (m, 2H), 3.33–3.15 (m, 4H), 2.30 (br s, 1H), 2.00 (br s, 1H), 1.90–1.64 (m, 6H), 1.47 (dd, J=7.1, 14.0, 2H), 1.26 (d, J=6.9, 14.0, 2H), 1.04 (d, J=6.6, 3H), 1.03 (d, J=6.6, 3H). ES–MS: calcd. for $C_{19}H_{36}N_4O_4$ (384.3); found: 383 [M–1].

Example 33

Synthesis of N-hydroxy-2-[N-(4-methylpentyl)-N-(2-(S)-3-methylbutyl-aminocarbonyl)pyrrolidin-1-carbonyl)amino]acetamide

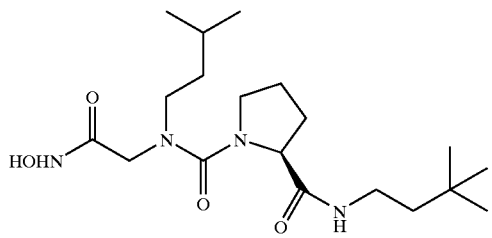

The title compound was prepared according to General Procedure F from glycine, 3-methyl-1-butanol, and 3,3-dimethy-butyl amine. $^1$H NMR (DMSO-d6): δ7.65 (dd, J=5.5, 5.5, 2H), 4.24 (dd, J=8.0, 8.0, 1H), 3.86 (d, J=16.5, 1H), 3.60 (d, J=16.5, 1H), 3.40–3.31 (m, 2H), 3.25–3.15 (m, 1H), 3.07–2.95 (m, 3H), 2.12–2.04 (m, 1H), 1.80 (br s, 1H), 1.70–1.58 (m, 2H), 1.54–1.44 (m, 1H), 1.42–1.28 (m, 4H), 0.87 (s, 9H), 0.86 (d, J=6.6, 3H), 0.85 (d, J=6.6, 3H). ES–MS: calcd. for $C_{19}H_{36}N_4O_4$ (384.3); found: 383 [M–1].

Example 34

Synthesis of N-hydroxy-2-[N-((3-methylbutyl)-N-(2-(S)-4-isopropyl-phenylaminocarbonyl)pyrrolidin-1-carbonyl)amino]acetamide

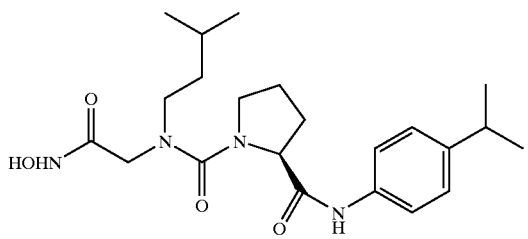

The title compound was prepared according to General Procedure F from glycine, 3-methyl-1-butanol, and 4-isopropyl aniline. $^1$H NMR (DMSO-d6): δ7.57 (d, J=8.5, 2H), 7.14 (d, J=8.5, 2H), 4.40 (dd, J=8.0, 8.0, 1H), 3.91 (d, J=16.5, 1H), 3.60 (d, J=16.5, 1H), 3.51–3.40 (m, 2H), 3.31–3.21 (m, 1H), 3.10–2.98 (m, 1H), 2.87–2.79 (m, 1H), 2.33–2.18 (m, 1H), 2.00–1.80 (m, 1H), 1.77–1.66 (m, 2H), 1.54–1.45 (m, 1H), 1.38 (dd, J=7.7, 15.4, 2H), 1.17 (d, J=6.9, 6H), 0.86 (d, J=6.3, 3H), 0.84 (d, J=6.3, 3H); ES–MS: calcd. for $C_{22}H_{34}N_4O_4$ (418.3); found: 417.5 [M−1].

Example 35

Synthesis of N-hydroxy-2-[N-(3-methylbutyl)-N-(2-(S)-4-biphenylaminocarbonyl)-pyrrolidin-1-carbonyl)amino]acetamide

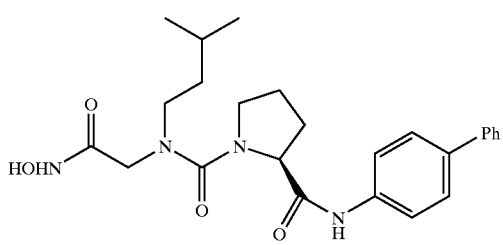

The title compound was prepared according to General Procedure F from glycine, 3-methyl-1-butanol, and 4-amino biphenyl. $^1$H NMR (DMSO-d6): δ7.79 (d, J=8.5, 2H), 7.66–7.52 (m, 4H), 7.46–7.41 (m, 2H), 7.34–7.29 (m, 1H), 4.43 (dd, J=7.7, 7.7, 1H), 3.94 (d, J=16.5, 1H), 3.61 (d, J=16.5, 1H), 3.50–3.38 (m, 2H), 3.50–3.38 (m, 1H), 3.32–3.22 (m, 1H), 3.08–2.99 (m, 1H), 2.23 (br s, 1H), 1.99 (br s, 1H), 1.84–1.75 (m, 2H), 1.50 (dd, J=6.6, 13.2, 2H), 1.40 (dd, J=7.4, 14.8 2H), 0.86 (d, J=6.3, 3H), 0.85 (d, J=6.3, 3H). ES–MS: calcd. for $C_{25}H_{32}N_4O_4$ (452.2); found: 451.4 [M−1].

Example 36

Synthesis of N-hydroxy-2-[N-(3-methylbutyl)-N-(2-(S)-4,5-dimethylthiazol-2-ylaminocarbonyl)pyrrolidin-1-carbonyl)amino]acetamide

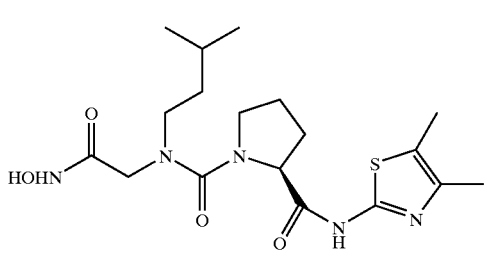

The title compound was prepared according to General Procedures F and G from glycine, 3-methyl-1-butanol, and 2-amino-4,5-dimethylthiazole. $^1$H NMR (DMSO-d6): δ4.66–4.63 (dd, J=8.0, 8.0 Hz, 1H), 3.95 (d, J=16.2 Hz, 1H), 3.83 (d, J=16.5 Hz, 1H), 3.70–3.60 (m, 2H), 3.33 (dd, J=6.0, 9.6, 2H), 2.41 (s, 3H), 2.40–2.33 (m, 2H), 2.33 (s, 3H), 2.11 (m, 1H), 1.98–1.85 (m, 2H), 1.66 (ddd, J=6.6, 6.6, 12.9, 1H), 1.58 (dd, J=5.5, 9.3, 2H), 1.04 (d, J=6.3, 6H). ES–MS: calcd. for $C_{18}H_{29}N_5O_4S$ (411.2); found: 412 [M+1].

Example 37

Synthesis of N-hydroxy-2-[N-(3-methylbutyl)-N-(2-(S)-quinolin-3-yl-aminocarbonyl)pyrrolidin-1-carbonyl)amino]acetamide

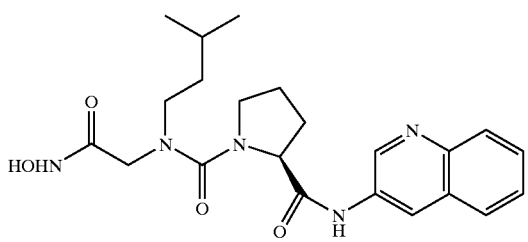

The title compound was prepared according to General Procedure F from glycine, 3-methyl-1-butanol, and 3-amino quinaline. $^1$H NMR (DMSO-d6): δ9.33 (m, 1H), 9.04 (m, 1H), 7.88 (dd, J=8.0, 8.0, 2H), 7.80 (dd, J=6.9, 6.9, 1H), 4.70 (dd, J=7.4, 7.4, 1H), 4.18 (d, J=16.5, 1H), 3.83 (ddd, J=6.9, 6.9, 13.7, 1H), 3.21 (ddd, J=6.6, 6.6, 14.6, 1H), 2.46 (m, 1H), 2.15 (m, 1H), 2.07–1.91 (m, 2H), 1.70 (ddd, J=6.3, 13.2, 13.2, 1H), 1.59 (dd, J=7.4, 14.8, 2H), 1.05 (d, J=6.3, 3H) 1.04 (d, J=6.3, 3H). ES–MS: calcd. for $C_{22}H_{29}N_5O_4$ (427.2); found: 428.4 [M+1].

Example 38

Synthesis of N-hydroxy-2-[N-(3-methylbutyl)-N-(2-(S)-3-phenoxyphenylaminocarbonyl)pyrrolidin-1-carbonyl)amino]acetamide

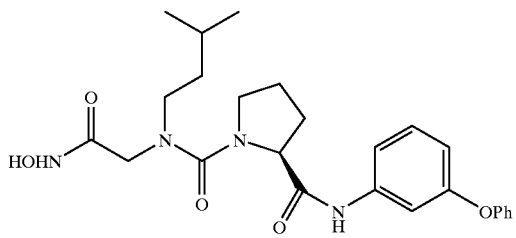

The title compound was prepared according to General Procedure F from glycine, 3-methyl-1-butanol, and 3-phenoxy aniline. $^1$H NMR (DMSO-d6): δ7.66–7.65 (m, 1H), 7.61–7.54 (m, 1H), 7.47 (dd, J=8.0, 8.0, 1H), 7.35–7.30 (m, 1H), 7.21–7.17 (m, 1H), 6.89–6.86 (m, 1H), 4.55 (dd, J=8.0, 8.0, 14.6 1H), 4.07 (d, J=16.8, 1H), 3.78 (d, J=16.8, 1H), 3.69–3.63 (m, 2H), 3.43 (ddd, J=7.7, 7.7, 14.6, 1H), 3.21 (ddd, J=7.7, 7.7, 15.4, 1H), 2.36 (m, 1H), 2.10 (m, 1H), 1.91 (m, 2H), 1.65 (ddd, J=6.6, 6.6, 13.2, 1H), 1.56 (dd, J=7.7, 15.1, 2H), 1.03 (d, J=6.3, 3H) 1.02 (d, J=6.3, 3H). ES–MS: calcd. for $C_{25}H_{32}N_4O_5$ (468.2); found: 467.5 [M−1].

Example 39

Synthesis of N-hydroxy-2-[N-(3-methylbutyl)-N-(2-(S)-4-phenylthiazol-2-ylaminocarbonyl)pyrrolidin-1-carbonyl)amino]acetamide

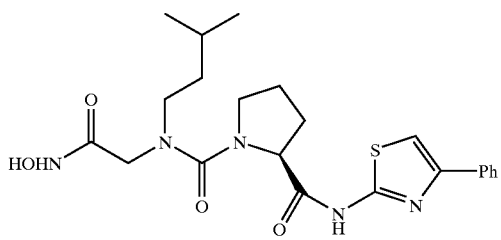

The title compound was prepared according to General Procedure F from glycine, 3-methyl-1-butanol, and 2-amino-4-phenyl thiazole. $^1$H NMR (DMSO-d6): δ7.91 (m, 2H), 7.89 (m, 1H), 7.63–7.61 (m, 2H), 7.45–7.40 (m, 2H), 7.34–7.29 (m, 1H), 4.53 (m, 1H), 3.79 (d, J=16.2, 1H), 3.64 (d, J=16.2, 1H), 3.51 (m, 1H), 3.17–3.15 (m, 1H), 2.23 (m, 1H), 1.98 (m, 1H), 1.77 (m, 2H), 1.50–1.42 (m, 3H), 0.86 (d, J=6.3, 6H). ES–MS: calcd. for $C_{22}H_{29}N_5O_4S$ (459.2); found: 458.4 [M−1].

Example 40

Synthesis of N-hydroxy-2-[N-(3-methylbutyl)-N-(2-(S)-5-phenyl-1,3,4-thiadiazol-2-ylaminocarbonyl)pyrrolidin-1-carbonyl)amino]acetamide

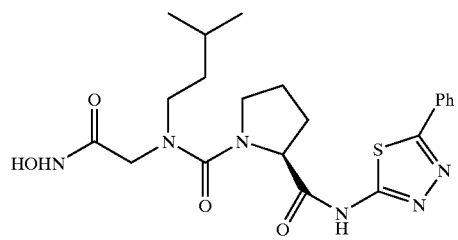

The title compound was prepared according to General Procedure F from glycine, 3-methyl-1-butanol, and 2-amino-5-phenylthiodiazole. $^1$H NMR (DMSO-d6): δ7.95–7.90 (m, 2H), 7.57–7.51 (m, 3H), 4.55 (dd, J=7.4, 7.4, 1H), 3.78 (d, J=16.5, 1H), 3.64 (d, J=16.5, 1H), 3.53–3.45 (m, 2H), 3.16 (ddd, J=8.5, 14.8, 14.8, 2H), 2.30–2.19 (m, 1H), 1.98 (m, 1H), 1.91–1.71 (m, 1H), 1.48 (ddd, J=6.6, 13.2, 19.8, 1H), 1.41 (dd, J=7.7, 7.7, 2H), 0.86 (d, J=6.6, 6H). ES–MS: calcd. for $C_{21}H_{28}N_6O_4S$ (460.2); found: 459.4 [M−1].

Example 41

Synthesis of N-hydroxy-2-[N-(3-methylbutyl)-N-(2-(s)-5-ethyl-1,3,4-thiadiazol-2-ylamninocarbonyl)pyrrolidin-1-carbonyl)amino]acetamide

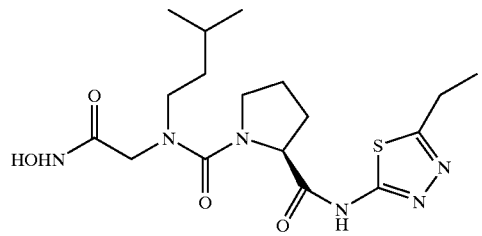

The title compound was prepared according to General Procedure F from glycine, 3-methyl-1-butanol, and 2-amino-5-ethylthiadiazole. ES–MS: calcd. for $C_{17}H_{28}N_6O_4S$ (412.2); found: 413 [M+1].

Example 42

Synthesis of N-hydroxy-2-[N-(3-methylbutyl)-N-(2-(S)-3-trifluoromethoxy-phenylaminocarbonyl)pyrrolidin-1-carbonyl)amino]acetamide

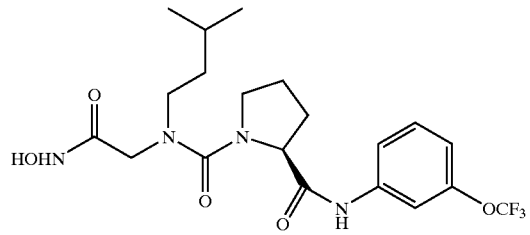

The title compound was prepared according to General Procedure F from glycine, 3-methyl-1-butanol, and 3-trifluoromethoxy aniline. ES–MS: calcd. for $C_{20}H_{27}F_3N_4O_5$ (460.2); found: 459.4 [M−1].

Example 43

Synthesis of N-hydroxy-2-[N-(2-cyclopentylethyl)-N-(2-(S)-4,5-dimethylthiazol-2-ylaminocarbonyl)pyrrolidin-1-carbonyl)amino]acetamide

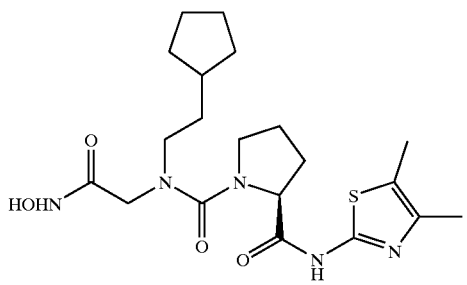

The title compound was prepared according to General Procedures F and G from glycine, 2-cyclopentylethyl alcohol, and 2-amino-4,5-dimethythiazole. $^1$H NMR (DMSO-d6): δ4.66–4.61 (dd, J=8.0 Hz, 1H), 4.00–3.94 (d, J=16.5 Hz, 1H), 3.86–3.80 (d, J=16.5 Hz, 1H), 3.70–3.61 (m, 2H), 3.35–3.29 (dd, J=5.8 Hz & 9.6 Hz, 2H), 2.40 (s, 3H), 2.33 (s, 3H), 2.11 (m, 1H), 1.90–1.83 (m, 5H), 1.81–1.63 (m, 6H), 1.27–1.24 (m, 2H). ES–MS: calcd. for $C_{20}H_{31}N_5O_4S$ (437.2); found: 438.2 [M+1].

Example 44

Synthesis of N-hydroxy-2-[N-(3-methylbutyl)-N-(2-(S)-3,4-methylenedioxy-phenylaminocarbonyl)pyrrolidin-1-carbonyl)amino]acetamide

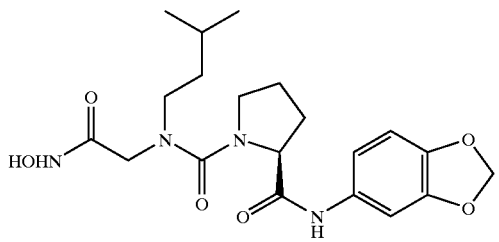

The title compound was prepared according to General Procedure F from glycine, 3-methyl-1-butanol, and 3,4-methylenedioxy aniline. $^1$H NMR (DMSO-d6): δ7.37 (d, J=2.2, 1H), 7.13–7.10 (m, 1H), 6.83 (d, J=8.2, 1H), 5.96 (s, 2H), 4.38 (dd, J=8.0, 8.0, 1H), 3.93 (d, J=16.5, 1H), 3.60 (d, J=16.5, 1H), 3.51–3.40 (m, 2H), 3.32–3.22 (m, 1H), 3.06–2.98 (m, 1H), 2.20 (br s, 1H), 1.91 (br s, 1H), 1.78–1.63 (m, 2H), 1.54–1.34 (m, 3H), 0.86 (d, J=6.6, 3H), 0.85 (d, J=6.6, 3H). ES–MS: calcd. for $C_{20}H_{28}N_4O_6$ (420.2); found: 421 [M+1].

Example 45

Synthesis of N-hydroxy-2-[N-(3-methylbutyl)-N-(2-(S)-thiazol-2-yl-aminocarbonyl)pyrrolidin-1-carbonyl)amino]acetamide

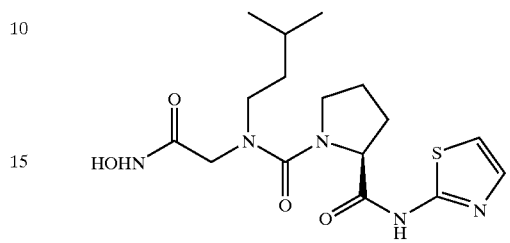

The title compound was prepared according to General Procedure F from glycine, 3-methyl-1-butanol, and 2-aminothiazole. $^1$H NMR (DMSO-d6): δ7.46 (d, J=3.6, 1H), 7.20 (d, J=3.6, 1H), 4.50 (dd, J=7.7, 7.7, 1H), 3.78 (d, J=16.5, 1H), 3.62 (d, J=16.5, 1H) 3.20–3.14 (m, 2H), 2.31–1.87 (m, 2H), 1.51–1.38 (m, 3H), 0.86 (d, J=6.3, 6H). ES–MS: calcd. for $C_{16}H_{25}N_5O_4S$ (383.2); found: 382.6 [M−1].

Example 46

Synthesis of N-hydroxy-2-[N-(2-cyclopentylethyl)-N-(2-(S)-5-phenyl-1,3,4-thiadiazol-2-ylaminocarbonyl)pyrrolidin-1-carbonyl)amino]acetamide

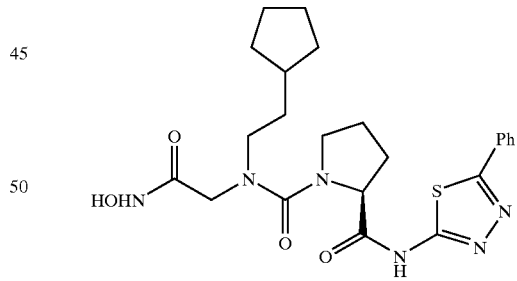

The title compound was prepared according to General Procedures F and G from glycine, 2-cyclopentylethylalcohol, and 2-amino-5-phenylthiodiazole. $^1$H NMR (DMSO-d6): δ8.13–8.10 (m, 2H), 7.73–7.71 (m, 3H), 4.76–4.71 (dd, J=7.7 Hz, 1H), 4.01–3.96 (d, J=16.5 Hz, 1H), 3.86 (m, 1H), 3.34–3.33 (m, 1H), 2.43 (m, 1H), 2.17 (m, 1H), 1.97–1.81 (m, 4H), 1.79–1.63 (m, 6H), 1.25–1.23 (m, 2H). ES–MS: calcd. for $C_{23}H_{30}N_6O_4S$ (486.2); found: 485.9 [M−1].

Example 47

Synthesis of N-hydroxy-2-[N-(2-cyclopentylethyl)-N-(2-(S)-3,4-methylenedioxy-phenylaminocarbonyl) pyrrolidin-1-carbonyl)amino]acetamide

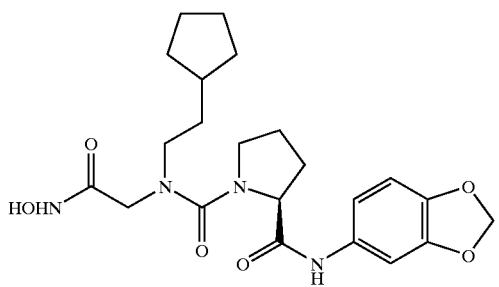

The title compound was prepared according to General Procedure F from glycine, 2-cyclopentylethylalcohol, and 3,4-methylenedioxy aniline. $^1$H NMR (DMSO-d6): δ7.36 (d, J=1.6, 1H), 7.11 (dd, J=1.9, 8.5, 1H), 6.82 (d, J 8.5, 1H), 5.96 (s, 2H), 4.38 (dd, J=7.4, 7.4, 1H), 4.05 (d, J=16.5, 1H), 3.93 (d, J=16.5, 1H), 3.45 (br s, 2H), 3.30–3.20 (m, 1H), 3.06–3.01 (m, 1H), 2.20 (br s, 1H), 1.91 (br s, 1H), 1.73–1.61 (m, 5H), 1.55–1.44 (m, 6H), 1.08–1.05 (m, 2H). ES–MS: calcd. for $C_{22}H_{30}N_4O_6$ (446.2); found: 445.6 [M–1].

Example 48

Synthesis of N-hydroxy-2-[N-(2-(thiophen-2-y)lethyl)-N-(2-(S)-4,5-dimethyl-thiazol-2-ylaminocarbonyl)pyrrolidin-1-carbonyl)amino]acetamide

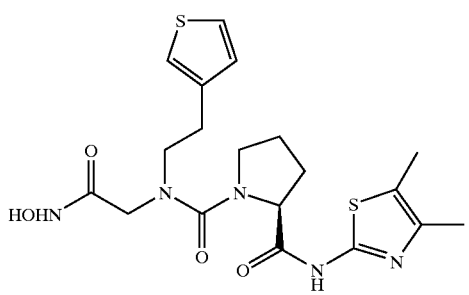

The title compound was prepared according to General Procedure F from glycine, 2-(3-thienyl)ethanol, and 2-amino-4,5-dimethythiazole. $^1$H NMR (DMSO-d6): δ7.44 (dd, J=2.7, 4.7, 1H), 7.20–7.19 (m, 1H), 7.00 (d, J=1.1, 4.7, 1H), 4.47 (dd, J=8.0, 8.0, 1H), 3.81 (d, J=16.5, 1H), 3.65 (d, J=16.5, 1H), 3.51–3.32 (m, 4H), 2.86 (dd, J=7.4, 7.4, 1H), 2.22 (s, 3H), 2.14 (s, 3H), 2.05–1.83 (m, 1H), 1.77–1.66 (m, 2H). ES–MS: calcd. for $C_{19}H_{25}N_5O_4S_2$ (451.1); found: 450.4 [M–1].

Example 49

Synthesis of N-hydroxy-2-[N-(3-methylbutyl)-N-(2-(S)-methylaminocarbonyl)-pyrrolidin-1-carbonyl)amino]acetamide

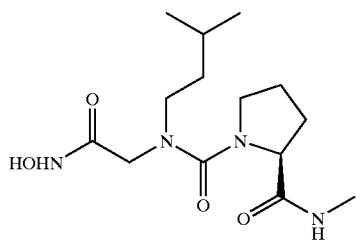

The title compound was prepared according to General Procedure F from glycine, 3-methyl-1-butanol, and methyl amine. ES–MS: calcd. for $C_{19}H_{25}N_5O_4S_2$ (314.2); found: 315 [M+1].

Example 50

Synthesis of N-hydroxy-2-[N-(3-methylbutyl)-N-(2-(S)-5-methyl-thiazol-2-yl-aminocarbonyl)pyrrolidin-1-carbonyl)amino]acetamide

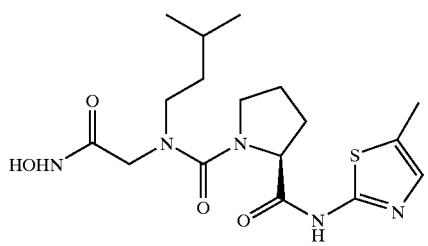

The title compound was prepared according to General Procedure G from glycine, 3-methyl-1-butanol, and 2-amino-5-methylthiazole. $^1$H NMR (DMSO-d6): δ7.30 (d, J=1.1, 1H), 4.66 (dd, J=8.0, 8.0, 1H), 3.97 (d, J=16.2, 1H), 3.65 (d, J=16.2, 1H), 3.70–3.60 (m, 2H), 3.32 (ddd, J=8.5, 14.3, 21.7, 2H), 2.51 (d, J=1.1, 3H). 2.40–2.33 (m, 1H), 2.12–2.10 (m, 1H), 2.02–2.83 (m, 2H), 1.69 (ddd, J=6.9, 13.5, 20.1, 2H), 1.60 (dd, J=5.5, 12.9, 2H), 1.04 (d, J=6.3, 6H). ES–MS: calcd. for $C_{17}H_{27}N_5O_4S$ (397.2); found: 398.7 [M+1].

Example 51

Synthesis of N-hydroxy-2-[N-(3-methylbutyl)-N-(2-(S)-4-methylthiazol-2-yl-aminocarbonyl)pyrrolidin-1-carbonyl)amino]acetamide

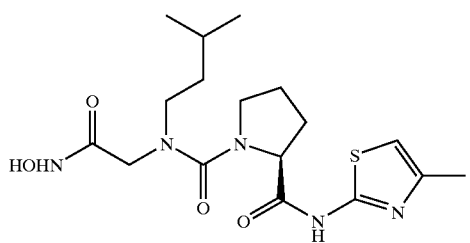

The title compound was prepared according to General Procedure G from glycine, 3-methyl-1-butanol, and 2-amino-4-methythiazole. $^1$H NMR (DMSO-d6): δ6.74 (d, J=1.1, 1H), 4.46 (dd, J=8.0, 8.0, 1H), 3.77 (d, J=16.5, 1H), 3.64 (d, J=16.5, 1H), 3.51–3.42 (m, 2H), 3.14 (dd, J=6.3, 9.6, 2H), 2.25 (s, 3H), 1.94 (br s, 1H), 1.80–1.68 (m, 2H), 1.53–1.44 (m, 1H), 1.40 (dd, J=4.9, 8.8, 2H), 0.86 (d, J=6.3, 6H). ES–MS: calcd. for $C_{17}H_{27}N_5O_4S$ (397.2); found: 398.7 [M+1].

Example 52

Synthesis of N-hydroxy-2-[N-(2-cyclopentylethyl)-N-(2-(S)-5-methyl-1,3,4-thiadiazol-2-yl-aminocarbonyl)pyrrolidin-1-carbonyl)amino]acetamide

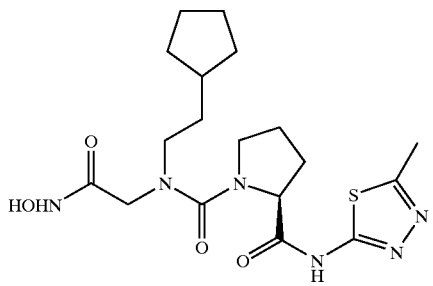

The title compound was prepared according to General Procedure G from glycine, 2-cyclopentylethyl alcohol, and 2-amino-5-methylthiadiazole. $^1$H NMR (DMSO-d6): δ4.50 (dd, J=8.0, 8.0, 1H), 3.78 (d, J=16.4, 1H), 3.63 (d, J=16.4, 1H), 3.57–3.56 (m, 2H), 3.11–3.02 (m, 2H), 2.60 (s, 3H), 2.20–2.10 (m, 1H), 1.95 (s, 1H), 1.80–1.62 (m, 1H), 1.52–1.28 (m, 6H), 1.15–1.00 (m, 1H). ES–MS: calcd. for $C_{22}H_{30}N_4O_6$ (424.2); found: 425.5 [M+1].

Example 53

Synthesis of N-hydroxy-2-[N-(2-cyclopentylethyl)-N-(2-(S)-thiazol-2-yl-aminocarbonyl)pyrrolidin-1-carbonyl)amino]acetamide

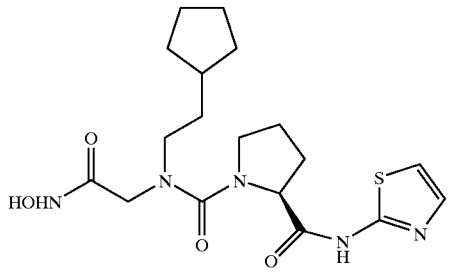

The title compound was prepared according to General Procedure G from glycine, 2-cyclopentylethylalcohol, and 2-amino thiazole. $^1$H NMR (DMSO-d6): δ7.46 (d, J=3.6, 1H), 7.20 (d, J=3.6, 1H), 4.50 (dd, J=7.7, 7.7, 1H), 3.79 (d, J=16.5, 1H), 3.62 (d, J=16.5, 1H), 3.53–3.45 (m, 2H), 3.13 (dd, J=7.1, 13.2, 2H), 2.25–2.15 (m, 3H), 1.95 (br s, 1H). 1.74–1.60 (m, 5H), 1.57–1.41 (m, 6H), 1.08–1.02 (m, 2H). ES–MS: calcd. for $C_{18}H_{27}N_5O_4S$ (409.2); found: 410.4 [M+1].

Example 54

Synthesis of N-hydroxy-2-[N-(2-cyclopentylethyl)-N-(2-(S)-indazol-6-yl-aminocarbonyl)pyrrolidin-1-carbonyl)amino]acetamide

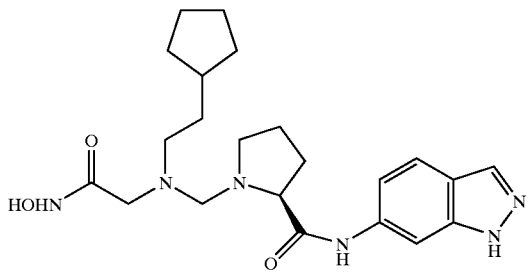

The title compound was prepared according to General Procedure G from glycine, 2-cyclopentylethylalcohol, and 5-aminoindazole. ES–MS: calcd. for $C_{19}H_{28}N_6O_4$ (442.2); found: 443 [M+H].

Example 55

Synthesis of N-hydroxy-2-[N-(2-cyclopentylethyl)-N-(2-(S)-4-morpholin-4-ylphenyl-aminocarbonyl)pyrrolidin-1-carbonyl)amino]acetamide

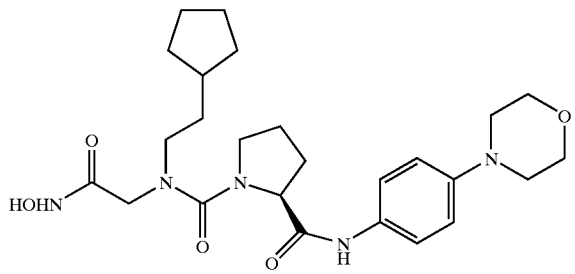

The title compound was prepared according to General Procedure G from glycine, 2-cyclopentylethylalcohol, and 4-(4-morpholino)aniline. $^1$H NMR (DMSO-d6): δ7.56 (d, J=8.8, 1H), 7.20 (d, J=8.8, 1H), 4.39 (dd, J=7.4, 7.4, 1H), 3.93 (d, J=17.9, 1H), 3.76–3.73 (m, 2H), 3.60 (d, J=17.9, 1H), 3.45 (br s, 1H), 3.25–3.22 (m, 1H), 3.10–3.01 (m, 3H), 2.20 (br s, 1H), 1.91 (br s, 1H), 1.73–1.63 (m, 5H), 1.54–1.44 (m, 6H), 1.06–0.93 (m, 2H). ES–MS: calcd. for $C_{25}H_{37}N_5O_5$ (487.3); found: 486.7 [M–1].

Example 56

Synthesis of N-hydroxy-2-[N-(2-cyclopentylethyl)-N-(2-(S)-4-hydroxyphenyl-aminocarbonyl)pyrrolidin-1-carbonyl)amino]acetamide

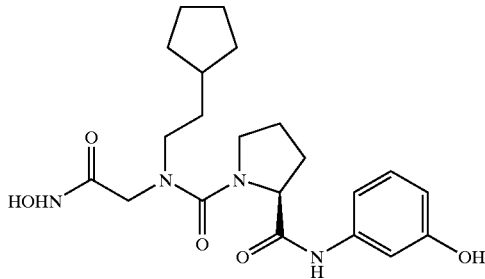

Step 1

To N-Cbz-L-proline (20 mmol) in DCM (100 mL) was added thionylchloride (200 mmol) and the solution heated to reflux for 20 min. The reaction was concentrated to dryness and the residue coevaporated two times with DCM. An aliquot (6.7 mmol) in DCM (3 mL) was added to a 0° C. solution of 3-hydroxyaniline (20 mmol) in pyridine (3 mL) and the reaction stirred 30 min. The reaction was concentrated, the residue dissolved in ethylacetate and then washed with water, 10% citric acid, saturated NaHCO$_3$ and brine, then dried (Na$_2$SO$_4$) to afford N-Cbz-[2-(3-hydroxyphenylaminocarbonyl)]-L-proline, which was used without further purification.

Step 2

To N-Cbz-[2-(3-hydroxyphenylaminocarbonyl)]-L-proline (5.0 mmol) in HOAc (10 mL) was added 30% HBr in acetic acid and the solution stirred for 40 min. The reaction was quenched by addition of 100 mL ethylether, and the resulting precipitate collected and recrystalized from MeOH/Et2O to afford 3.5 mmol 2-(3-hydroxyphenylaminocarbonyl)-L-proline hydrobromide (70%)

Step 3

An aliquot of the carbamoyl chloride N-(2-(cyclopentyl)ethyl)-N-methoxycarbonyl-methyl)carbamoyl chloride (prepared from 2-(cyclopentyl)ethylalcohol as described in General Procedure G, Steps 1–3; 200 μmol) dissolved in DCM (1 mL) was added to a 0° C. solution of 2-(3-hydroxyphenylaminocarbonyl)-L-proline hydrobrmide (200 μmol) in pyridine (1 mL). After 30 minutes the reaction mixture was diluted with ether (10 mL), washed with 10% KHSO$_4$ (2×5 mL), brine (5 mL) dried (NaSO$_4$) and evaporated to provide ethyl 2-[N-(2-(cyclopentyl)ethyl)-N-[2-(3-hydroxyphenyl)aminocarbonylpyrrolidin-1-carbonyl)amino]acetate.

Step 4

To ethyl 2-[N-(2-(cyclopentyl)ethyl)-N-[2-(3-hydroxyphenyl)aminocarbonyl-pyrrolidin-1-carbonyl)amino]acetate (200 μmol) in dioxane (2 mL) was added 50% aqueous hydroxylamine (1 mL), and the reaction stirred for 36 h. The crude reaction mixture was then purified by preparative reverse-phase (C18) HPLC to afford N-hydroxy-{N-[2-(cyclopentyl)ethyl]-N-[2-(3-hydroxyphenyl)aminocarbonylpyrrolidin-1-ylcarbonyl]-amino}acetamide. $^1$H NMR (DMSO-d6): δ9.33 (br s, 1H), 7.25–7.24 (m, 1H), 7.07–6.99 (m, 2H), 6.45–6.41 (m, 1H), 4.38 (dd, J=8.4, 8.4, 1H), 3.88 (d, J=16.5, 1H), 3.66 (d, J=16.5, 1H), 3.48–3.46 (m, 2H), 3.27–3.22 (m, 1H), 3.20–3.01 (m, 1H), 2.19 (br s, 1H), 1.91 (br s, 1H), 1.73–1.68 (m, 5H), 1.63–1.41 (m, 6H), 1.08–1.05 (m, 2H). ES–MS: calcd. for C$_{21}$H$_{30}$N$_4$O$_5$ (418.2); found: 417.7 [M−1].

Example 57

Synthesis of N-hydroxy-2-[N-(2-cyclopentylethyl)-N-(2-(S)-4-phenylpyrimidin-2-yl-aminocarbonyl) pyrrolidin-1-carbonyl)amino]acetamide

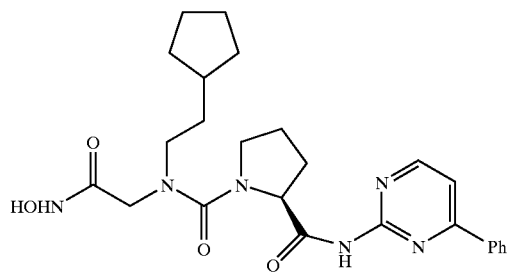

The title compound was prepared from 2-amino-4-phenylpyrimidine using the route described in Example 56. ES–MS: calcd. for C$_{19}$H$_{28}$N$_6$O$_4$ (480.3); found: 481 [M+H].

Example 58

Synthesis of N-hydroxy-2-[N-(2-cyclopentylethyl)-N-(2-(S)-pyrimidin-2-yl-aminocarbonyl)pyrrolidin-1-carbonyl)amino]acetamide

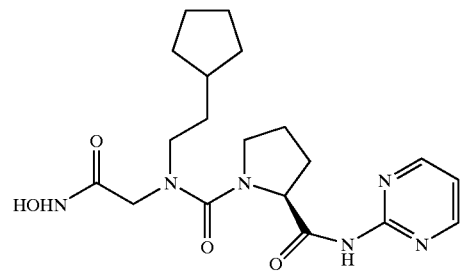

The title compound was prepared from 2-aminopyrimidine using the route described in Example 56. $^1$H NMR (DMSO-d6): δ8.83 (d, J=4.7, 2H), 7.37 (dd, J=4.7, 4.7 1H) 4.79 (dd, J=6.9, 6.9, 1H), 3.97 (d, J=16.2, 1H), 3.78 (d, J=16.2, 1H), 3.47–3.42 (m, 1H), 3.38–3.22 (ddd, J=8.8, 14.9, 14.9, 1H), 2.40 (m, 1H), 2.10 (m, 1H), 1.92–1.83 (m, 5H), 1.81–1.59 (m, 7H), 1.27–1.20 (m, 3H). ES–MS: calcd. for C$_{19}$H$_{28}$N$_6$O$_4$ (404.2); found: 441.7 [M+Na].

Example 59

Synthesis of N-hydroxy-2-[N-(2-cyclopentylethyl)-N-(2-(S)-pyrazin-2-yl-aminocarbonyl)pyrrolidin-1-carbonyl)amino]acetamide

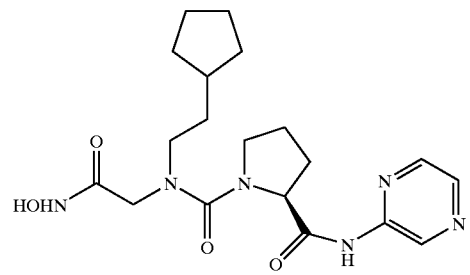

The title compound was prepared from 2-aminopyrazine using the route described in Example 56. ES–MS: calcd. for C$_{19}$H$_{28}$N$_6$O$_4$ (404.4694); found: 427.4 [M+Na].

Example 60

Synthesis of N-hydroxy-2-[N-(2-cyclohex-1-enylethyl)-N-(2-(S)-tert-butoxycarbonylaminocarbonyl)pyrrolidin-1-carbonyl)amino]acetamide

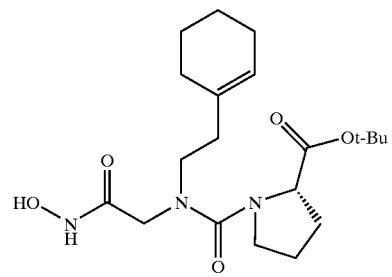

Step 1

To a solution of methyl bromoacetate (5 g, 32.7 mmol) in DCM (150 mL) was added 2-(1-cyclohexenyl)ethylamine (11.4 ml, 81.71 mmol) over 5 min. After 2 h, the solvent was removed and the residue purified on silica gel (Merck 60; (1:9) ethyl acetate/hexane) to afford methyl 2-[N-(2-cyclohex-1-enyl)ethylamino]acetate (5.0 g, 78%).

Step 2

To phosgene (20% in toluene, 15 mL) in DCM (100 mL) was added a solution of methyl 2-[N-(2-cyclohex-1-enyl)ethylamino]acetate (2.4 g, 12.18 mmol) and triethylamine (2.79 mL, 20 mmol) in DCM (30 mL). After 30 min, excess phosgene and solvents were removed in vacuo, the residue dissolved in DCM (100 mL) and then treated with a solution of L-proline t-butyl ester (3.12 g, 18.22 mol) and triethylamine (2.79 mL, 20 mmol) in DCM (30 mL). After 16 h, the solution was washed with HCl (1N, 2×) and brine, dried (Na$_2$SO$_4$), concentrated, and then purified on silica gel (ethyl acetate/hexane) to afford methyl N-{[2-(cyclohex-1-enyl)ethyl]-N-[2-(t-butyloxycarbonyl)-L-pyrrolidin-1-carbonylamino}acetate (4.5 g, 94%).

To N-{[2-(cyclohex-1-enyl)ethyl]-N-[2-(t-butyloxycarbonyl)-L-pyrrolidin-1-carbonylamino}acetate (1.5 g, 3.81 mmol) in dioxane (25 mL) was added aqueous 50% hydroxylamine (50 mL) and the solution stirred for 16 h. Dioxane was removed in vacuo and the aqueous layer was extracted with ethyl acetate (3×). The organic layers were washed with brine, dried over sodium sulfate, and concentrated to give 1.21 g of N-hydroxy-{N-[2-(cyclohex-1-enyl)ethyl]-N-[2-(t-butyloxycarbonyl)-L-pyrrolidin-1-carbonyl)amino}-acetamide (81%).

Example 61

Synthesis of N-hydroxy-2-[N-(2-(thiophen-2-yl)ethyl)-N-(2-(S)-phenyl-aminocarbonyl)pyrrolidin-1-carbonyl)amino]propionamide

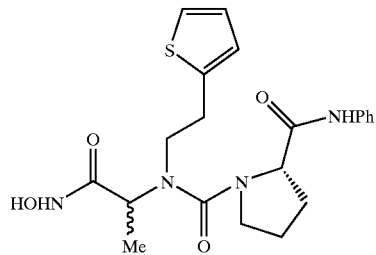

Step 1

Methyl 2-{N-[2-(thiophen-2-yl)ethyl]-N-[2-(t-butyloxycarbonyl)-L-pyrrolidin-1-carbonyl)}-2-methylacetate (0.68 g, 1.67 mmol) was prepared using the method of Example 60 above using methyl (±)-2-bromopropionate, 2-(2-thiophene)ethylamine and L-proline t-butyl ester) was treated with 4N HCl in dioxane (8 mL) for 20 h. Excess HCl and dioxane were removed and the crude acid (200 mg, 0.56 mmol) was treated with aniline (57 μL, 0.62 mmol), PyBOP (293 mg, 0.56 mmol), and DIEA (118 μL, 0.68 mmol) for 16 h. Standard aqueous work-up and purification on silica gel (EtOAc/hexane) afforded methyl 2-{N-[2-(thiophen-2-yl)ethyl]-N-[2-(phenylaminocarbonyl)-L-pyrrolidin-1-carbonyl)amino}-2-methylacetate.

Step 2

To a solution of methyl 2-{N-[2-(thiophen-2-yl)ethyl]-N-[2-(phenylaminocarbonyl)-L-pyrrolidin-1-carbonyl)}-2-methylacetate (20 mg) in dioxane (1 mL) was added aqueous 50% hydroxylamine (2 mL) and the reaction was stirred at room temperature for two days, and then purified by RP-HPLC to give N-hydroxy-2-{N-[2-(thiophen-2-yl)ethyl]-N-[2-(phenylaminocarbonyl)-L-pyrrolidin-1-carbonyl)amino}-2-methylacetamide. MS (APCI) m/z 431 [M+H].

Example 62

Synthesis of N-hydroxy-2-[N-(2-(thiophen-2-yl)ethyl)-N-(2-(S)-phenyl-aminocarbonyl)pyrrolidin-1-carbonyl)amino]acetamide

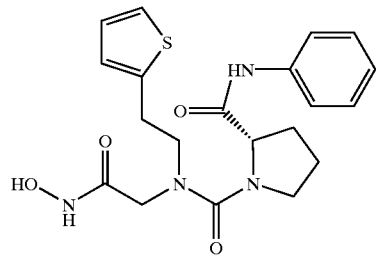

Small-scale Synthesis

To resin bound 2-{N-[2-(thiophen-2-yl)ethyl]-N-[2-(t-butyloxycarbonyl)-L-pyrrolidin-1-carbonyl)amino}acetate (prepared according to General Procedures A–C from ArgoGel-OH, bromoacetyl bromide, 2-(2-thiophene)ethylamine and L-proline t-butyl ester) was added 33% TFA in DCM and the resin shaken for 2 h. The resin was drained, washed with DCM, DMF, MeOH and DCM, and then suspended in DCM. Aniline, DIEA and PyBOP were added and the resin shaken overnight. The suspension was drained, washed as aboved, and then suspended in a 1:1 mixture of dioxane and aqueous 50% hydroxylamine and shaken for 2 d. The resin was filtered and the filtrate purified by preparative reverse-phase (C18) HPLC to afford N-hydroxy-2-{N-[2-(thiophen-2-yl)ethyl]-N-[2-(phenylamino-carbonyl)-L-pyrrolidin-1-carbonyl]amino}acetamide.

Example 63

Synthesis of N-hydroxy-2-[N-(2-(thiophen-2-yl)ethyl)-N-(2-(S)-phenyl-aminocarbonyl)pyrrolidin-1-carbonyl)amino]acetamide

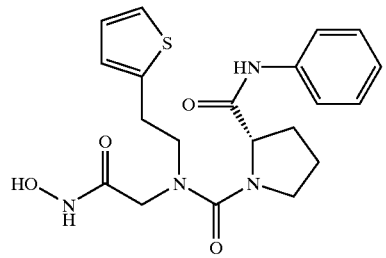

Large-scale Synthesis

Step 1

To a solution of methyl bromoacetate (32.7 mmol) in DCM (150 mL) was added 2-(2-thiophene)ethylamine (81.71 mmol) over 5 min. After 2 h, the solvent was removed and the residue purified on silica gel (Merck 60; ethyl acetate/hexane) to afford methyl 2-[2-(thiophen-2-yl)ethylamine]acetate.

Step 2

To a solution of phosgene (20% in toluene, 3 mL) in DCM (10 mL) at 0° C. was added a solution of methyl 2-[2-(thiophen-2-yl)ethylamine]acetate (2.81 mmol) and Et$_3$N in DCM (2 mL). After 30 min, the phosgene and solvents were removed in vacuo, and the residue dissolved in DCM (20 mL). To the DCM solution was added a solution of L-proline aniline amide (4.21 mmol; prepared in two steps from N-Boc-L-proline) and Et$_3$N in DCM (10 mL). After 18 h, the solution was washed with HCl (1N) and brine, dried (Na$_2$SO$_4$), concentrated and purified on silica gel (EtOAc/hexane) to afford methyl 2-{N-[2-(thiophen-2-yl)ethyl]-N-(2-phenylaminocarbonyl)-L-pyrrolidin-1-carbonyl)amino}acetate.

Step 3

To a solution of methyl 2-{N-[2-(thiophen-2-yl)ethyl]-N-(2-phenylaminocarbonyl)-L-pyrrolidin-1-carbonyl)amino}acetate in dioxane was added aqueous 50% hydroxylamine and the reaction stirred for 48 h. The solution was evaporated to dryness and then purified on silica gel (MeOH/DCM) to provide N-hydroxy-2-{N-[2-(thiophen-2-yl)ethyl]-N-[2-(phenylamino-carbonyl)-L-pyrrolidin-1-carbonyl]amino}acetamide. MS (APCI) m/z 417 [M+H].

Formulation Examples

The following are representative pharmaceutical formulations containing a compound of Formula (I).

Example 1

Tablet Formulation

The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Example 2

Capsule Formulation

The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

Example 3

Suspension Formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 ml |
| colorings | 0.5 mg |
| distilled water | q.s. to 100 ml |

Example 4

Injectable Formulation

The following ingredients are mixed to form an injectable formulation.

| Ingredient | Amount |
|---|---|
| compound of this invention | 0.2 mg–20 mg |
| sodium acetate buffer solution, 0.4 M | 2.0 ml |
| HCl (1N) or NaOH (1N) | q.s. to suitable pH |
| water (distilled, sterile) | q.s. to 20 ml |

Example 5

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| compound of the invention | 500 mg |
|---|---|
| Witepsol ® H-15 | balance |

Biological Examples

Example 1

Inhibition of Peptide Deformylase Activity

The PDF/FDH coupled assay (Lazennec, C. & Meinnel, T., *Anal Biochem.* 224:180–182 (1997)) was used. In this coupled assay, the formate released by PDF from its substrate fMAS is oxidized by the coupling enzyme FDH, reducing one molecule of NAD$^+$ to NADH, which causes an increase in absorption at 340 nm. All assays were carried out at room temperature in a buffer of 50 mM HEPES, pH 7.2, 10 mM NaCl, 0.2 mg/mL BSA, in half-area 96-well microtiter plates (Corning). The reaction was initiated by adding a mixture of 0.5 Unit/mL FDH, 1 mM NAD$^+$, and fMAS at the desired concentration. To determine IC$_{50}$ (the concentration needed to inhibit 50% of enzyme activity) values, PDF was pre-incubated for 10 min. with varying concentrations of actinonin, and the deformylation reaction was initiated by the addition of reaction mixture containing 4 mM FMAS. The initial reaction velocity, y, was measured as the initial rate of absorption increase at 340 nm using a SpectraMax plate reader (Molecular Devices, Sunnyvale, Calif.). The inhibitor concentration [In] at which 50% of the enzyme activity is inhibited, IC$_{50}$, was calculated using the following formula:

$$y=y_o/(1+[In]/IC_{50})$$

where $y_o$ is the reaction velocity in the absence of inhibitor. Solving this equation for $IC_{50}$ at the [In] when $y=y_o/2$ yields $IC_{50}$. The $IC_{50}$ was calculated based on a nonlinear least-square regression fit using a commercial software package (DeltaGraph 4.0).

Using this assay, the $IC_{50}$ of various compounds were determined against deformylase enzyme containing nickel or zinc as the metal ion.

Example 2

Assay for Testing Antimicrobial Activity

Minimum inhibitory concentrations (MICs) were determined using the microdilution method in 96-well format plates. Compounds were suspended in DMSO at 5 or 10 mg/ml and stored at 4° C. until used. They were diluted in Mueller-Hinton Broth (MHB) or Trypticase Soy Broth (TSB) and used for MIC determination. The range of concentrations tested was 64–0.0625 Tg/ml final concentration using a two-fold dilution system.

The inoculum was prepared from cells grown on Trypticase Soy Agar (TSA) and incubated overnight at 35° C., 5 to 10 colonies were used to inoculate MHB or TSB broths, and the culture was incubated overnight at 35° C. The overnight culture was diluted 1:10, incubated for one hour at 35° C., diluted to the appropriate inoculum size and applied to the wells containing broth and test compound. Inoculum sizes were $2 \times 10^4$ CFU/ml.

Plates were incubated at 35° C. for 48 hours and MIC were recorded after 18 hours of incubation for bacteria. MIC was defined as the lowest concentration of compound that does not produce visible growth after incubation.

Minimum inhibitory concentrations for various compounds against *H. influenza* and *S. aureus, S. epidermidis, E. faecium, S. pneumoniae, H. influenzae* acr, *M. catarrhalis, E. coli* and *E. coli* acr were determined. The deformylase enzyme was obtained from *E. coli*.

All the compounds tested showed activity against these microbes.

Example 3

Demonstration of Selective Inhibition of PDF Compared to MMP-7 (Matrilysin)

As noted previously, inhibitors which are selective for peptide deformylase over matrix metalloproteinases are desirable in order to avoid side effects.

In order to test the compounds of the invention for possible inhibitory effects on matrix metalloproteinases, the following assay for MMP-7 (matrilysin) was used. MMP-7 (Matrilysin) Assay:

Matrilysin activity is assayed using a thio-peptide (Pro-Leu-Gly-S-Leu-Leu-Gly) as substrate. Upon enzyme hydrolysis, the thiolate is released as a product. The thiolate thus generated reacts with DTNB (dithionitrobenzene), giving rise to a yellow color which is monitored at 405 nm. The assay is carried out at room temperature; the assay buffer contains 50 mM Tricine, pH 7.5, 0.2 M NaCl, 10 mM $CaCl_2$, and 0.05% Brij, in a half-area 96-well microtiter plate. The reaction is initiated by adding a mixture of 200 TM DTNB and 100 TM thiopeptide in buffer. To determine $IC_{50}$ (the concentration needed to inhibit 50% of enzyme activity) values, MMP-7 was preincubated for 10 minutes with varying concentrations of compounds, and the hydrolysis initiated by the addition of reaction mixture containing thiopeptide and DTNB. The reaction rate was recorded as the absorbance increase in $OD_{405}$ over 30 minutes using a SpectraMax plate reader (Molecular Devices, Sunnyvale, Calif.). The inhibitor concentration [In] at which 50% of the enzyme activity is inhibited, $IC_{50}$, was calculated using the following formula:

$$y=y_o/(1+[In]/IC_{50})$$

where $y_o$ is the reaction velocity in the absence of inhibitor. Solving this equation for $IC_{50}$ at the [In] when $y=y_o/2$ yields $IC_{50}$.

Using this assay, the $IC_{50}$ of various compounds were determined. The compounds provided by the invention showed high selectivity for PDF as compared to their activity against MMP-7. Similar selectivity of the compounds for peptide deformylase over MMP-1, MMP-2, MMP-3, MMP-9, MMP-13, MT-MMP-1, and tissue necrosis factor converting enzyme was observed. Similar selectivity was also observed over other metalloproteinases such as angiotensin converting enzyme.

Example 4

Discontinuous PDF Assay

The gene for PDF was cloned from *S. aureus* and *E. coli* by PCR amplification. The PDF proteins were overexpressed in *E. coli*. The native $Fe^{2+}$-containing PDF or its more stable surrogate $Ni^{2+}$-containing PDF were prepared according to Wagner et al. (1998) *Biochemical & Biophysical Research Communications* 246:342–6. Both enzymes have similar activity as reported in the literature. Discontinuous assay is carried out in a buffer of 10 mM NaCl and 50 mM HEPES, pH 7.2. Typically, 2 nM of PDF was incubated with inhibitor for 30 minutes prior to the addition of 4 mM fMAS substrate. The deformylation proceeded at room temperature for 30 minute. The enzyme activity is directly proportional to the amount of formate released, which can be quantified by monitoring the absorbance increase at 340 nm after the addition of 1 mM of $NAD^+$ and 0.5 U/ml of formate dehydrogenase.

Example 5

Mouse Septicemia Model for Determining in vivo Efficacy

CD1 female out-bred mice (Charles River Laboratories) weighing 18–22 grams each were injected intraperitoneally with 0.5 ml of a suspension containing $5 \times 10^7$ cfu of *S. aureus* (Smith strain) in 7% hog gastric mucosa (mucin). The mice were treated, either subcutaneously (SC), intravenously (IV) or orally (PO), 1 hr and 5 hr after infection. Six groups of six mice each were given different dosage levels representing two-fold dilutions of each compound (range of 100 mg/kg–0.1 mg/kg). Vancomycin was used as the control antibiotic and was administered SC. Compounds were formulated in PBS and untreated controls were dosed with vehicle alone.

Deaths in each group were monitored daily for 6 days and cumulative mortality was used to determine the 50% protective doses ($PD_{50}$), which were calculated using the method of Reed and Muench.

The foregoing invention has been described in some detail by way of illustration and example, for purposes of clarity and understanding. It will be obvious to one of skill in the art that changes and modifications may be practiced within

What is claimed is:

1. A compound of Formula (I):

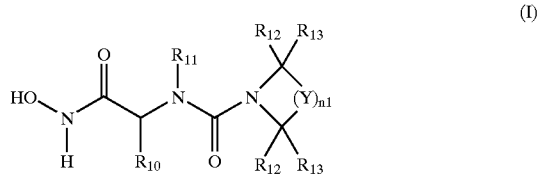

(I)

wherein:

R$_{10}$ is selected from the group consisting of hydrogen, R$_{14}$, R$_{15}$OH, and R$_{15}$—O—R$_{16}$, where R$_{14}$ and R$_{16}$ are independently selected from the group consisting of —(C$_1$–C$_{12}$) alkyl, substituted alkyl, or heteroalkyl, —(C$_1$–C$_{12}$) alkenyl, substituted alkenyl, or heteroalkenyl, —(C$_1$–C$_{12}$) alkynyl, substituted alkynyl, or heteroalkynyl, or —(C$_0$–C$_8$ alkylene or substituted alkylene)-(C$_6$–C$_{12}$ arylene or heteroarylene)-(C$_0$–C$_8$ alkyl or substituted alkyl); and R$_{15}$ is selected from the group consisting of —(C$_1$–C$_{12}$) alkylene, substituted alkylene, or heteroalkylene, —(C$_1$–C$_{12}$) alkenylene, substituted alkenylene, or heteroalkenylene, —(C$_1$–C$_{12}$) alkynylene, substituted alkynylene, or heteroalkynylene, or —(C$_0$–C$_8$ alkylene or substituted alkylene)-(C$_6$–C$_{12}$ arylene or heteroarylene)-(C$_0$–C$_8$ alkylene or substituted alkylene);

R$_{11}$ is selected from the group consisting of hydrogen, —(C$_1$–C$_{12}$) alkyl, substituted alkyl, or heteroalkyl, —(C$_1$–C$_{12}$) alkenyl, substituted alkenyl, or heteroalkenyl, —(C$_1$–C$_{12}$) alkynyl, substituted alkynyl, or heteroalkynyl, or —(C$_0$–C$_{12}$ alkylene or substituted alkylene)-(C$_6$–C$_{12}$ arylene or heteroarylene)-(C$_0$–C$_{12}$ alkyl or substituted alkyl);

n$_1$ is 2;

Y is —CR$_{12}$R$_{13}$—; where R$_{12}$ and R$_{13}$ are each independently hydrogen, R$_{17}$, —OH, —OR$_{17}$, —SH, —SR$_{17}$, —NH$_2$, —NHR$_{17}$, —NR$_{17}$R$_{18}$, —C(=O)R$_{17}$, —C(=O)NR$_{17}$R$_{18}$, —C(=O)SR$_{17}$, —C(=O)CR$_{17}$R$_{18}$R$_{19}$, —C(=O)OCR$_{17}$R$_{18}$R$_{19}$, —S(=O)$_2$NR$_{17}$R$_{18}$, —N(R$_{17}$)C(=O)R$_{18}$, —N(R$_{17}$)C(=O)OR$_{18}$, —N(R$_{17}$)S(=O)$_2$R$_{18}$, or —N(R$_{17}$)S(=O)$_2$OR$_{18}$, or where two vicinal R$_{12}$ or R$_{13}$ groups combine to form a substituted or unsubstituted —(C$_4$–C$_{10}$) cyclic alkyl, cyclic heteroalkyl, aryl or heteroaryl group; where R$_{17}$, R$_{18}$ and R$_{19}$ are each independently hydrogen, —(C$_1$–C$_{12}$) alkyl, substituted alkyl, or heteroalkyl, —(C$_1$–C$_{12}$) alkenyl, substituted alkenyl, or heteroalkenyl, —(C$_1$–C$_{12}$) alkynyl, substituted alkynyl, or heteroalkynyl, alkoxy, or —(C$_0$–C$_8$ alkylene or substituted alkylene)-(C$_6$–C$_{12}$ arylene or heteroarylene)-(C$_6$–C$_8$ alkyl or substituted alkyl, or where, when two or three of R$_{17}$, R$_{18}$ and R$_{19}$ are attached to the same atom, two or three of R$_{17}$, R$_{18}$ and R$_{19}$ can combine to form a substituted or unsubstituted —(C$_4$–C$_{10}$)cyclic alkyl, cyclic heteroalkyl, aryl or heteroaryl group; or a pharmaceutically acceptable salt thereof;

wherein heteroaryl refers to a substituent selected from the group consisting of imidazolyl, prazolyl, pyrazinyl, pyridazinyl, pyrimidinly, pyrrolyl, pyridyl, thiophene, indolyl, quinolinyl, quinazolinyl, benzimidazolyl, indolizinyl, and benzothienyl;

wherein cyclic heteroalkyl refers to a substituent selected from the group consisting of 1-ethyl-6-propylpiperidino, 2-ethylthiophenyl, piperazino, pyrrolidino, piperidino, and morpholino; and wherein each heteroaryl or cyclic heteroalkyl ring is optionally substituted on any atom within the ring from one to three substituents independently selected from the group consisting of alkyl, alkenyl, alkynyl, benzyl, halogen, alkoxy, acyloxy, amino, mono or dialkylamino, hydroxyl, mercapto, carboxy, benzyloxy, phenyl, aryloxy, cyano, nitro, thioalkoxy, carboxaldehyde, carboalkoxy and carboxamide.

2. The compound of claim 1 where R$_{10}$ is hydrogen, alkyl, or —(C$_1$–C$_{12}$) alkylene-OH.

3. The compound of claim 1 where R$_{10}$ hydrogen, methyl, or hydroxymethyl.

4. The compound of claim 1 where R$_{10}$ is hydrogen.

5. The compound of claim 1 where R$_{11}$ is alkyl, substituted alkyl, alkenyl, heteroaralkyl, or heteroalkyl.

6. The compound of claim 1 where R$_{11}$ is methyl, ethyl, butyl, 3-methylbutyl, pentyl, 2-cyclohex-1-enylethyl, 2-(2-fluorophenyl)ethyl, 3-ethoxypropyl, 2-(thiophenyl-2-yl) ethyl, 2-cyclohexylethyl, 1-napthylmethyl, 4-fluorobenzyl, 2-ethylthioethyl, 2-cyclopentylethyl or 2-(4-chlorophenyl) ethyl.

7. The compound of claim 1 where R$_{11}$ is 3-methylbutyl or 2-cyclopentylethyl.

8. The compound of claim 1 where the group:

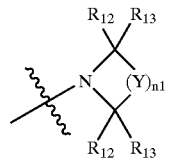

is a group of formula:

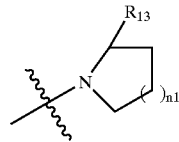

wherein:

n1 is 1; 2215 and

R$_{13}$ is —C(=O)NR$_{17}$R$_{18}$ or —N(R$_{17}$)C(=O)OR$_{18}$ where R$_{17}$ and R$_{18}$ are each independently hydrogen, —(C$_1$–C$_{12}$) alkyl, substituted alkyl, or heteroalkyl, —(C$_1$–C$_{12}$) alkenyl, substituted alkenyl, or heteroalkenyl, —(C$_1$–C$_{12}$) alkynyl, substituted alkynyl, or heteroalkynyl, or —(C$_0$–C$_8$ alkylene or substituted alkylene)-(C$_6$–C$_{12}$ arylene or heteroarylene)-(C$_0$–C$_8$ alkyl or substituted alkyl), or when R$_{16}$ and R$_{17}$ are attached to the same atom, they can combine to form a substituted or unsubstituted —(C$_4$–C$_{10}$)cyclic alkyl, cyclic heteroalkyl, aryl or heteroaryl group.

9. The compound of claim 1 where the group:

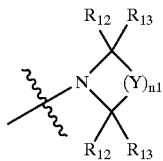

is a group of formula:

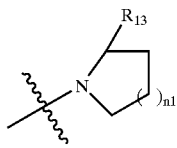

wherein:

n1 is 1; and

R$_{13}$ is —C(=O)NHR$_{18}$ where R$_{18}$ is hydrogen or —(C$_1$–C$_{12}$) alkyl, aryl, or heteroaryl.

10. The compound of claim 8 where R$_{13}$ is 3-phenoxyphenylaminocarbonyl, phenylaminocarbonyl, 2-methyl-1,3,4-thiadiazol-5-ylaminocarbonyl, thiazol-2-ylaminocarbonyl, 6-phenylimidazol-2-ylaminocarbonyl, pyrazin-2-ylaminocarbonyl, 3-methylbutylaminocarbonyl, imidazol-2-ylaminocarbonyl, 4,5-dimethylthiazol-2-ylaminocarbonyl, tert-butoxycarbonylamino, piperidin-1-ylcarbonyl, methylaminocarbonyl, or 4-benzylpiperazin-1-ylcarbonyl.

11. The compound of claim 1 where the group:

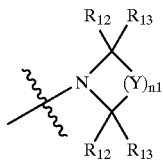

is a group of formula:

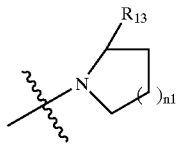

wherein:

n1 is 1; and

R$_{13}$ is 3-phenoxyphenylaminocarbonyl, 2-methyl-1,3,4-thiadiazol-5-ylaminocarbonyl, thiazol-2-ylaminocarbonyl, 6-phenylimidazol-2-ylaminocarbonyl, pyrazin-2-ylaminocarbonyl, 3-methylbutylaminocarbonyl, imidazol-2-ylaminocarbonyl, or 4,5-dimethylthiazol-2-ylaminocarbonyl.

12. A compound of Formula (Ia):

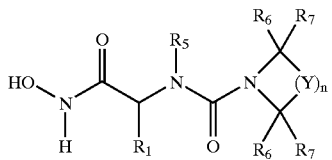

(Ia)

wherein:

R$_1$ is selected from the group consisting of hydrogen, R$_s$, and —R$_t$—O—R$_s$ where R$_s$ is selected from the group consisting of —(C$_1$–C$_{12}$) alkyl, —(C$_1$–C$_{12}$) alkenyl, or —(C$_1$–C$_{12}$) alkynyl; and R$_t$ is selected from the group consisting of —(C$_1$–C$_{12}$) alkylene, —(C$_1$–C$_{12}$) alkenylene, or —(C$_1$–C$_{12}$) alkynylene;

R$_5$ is selected from the group consisting of hydrogen, —(C$_1$–C$_{12}$) alkyl, substituted alkyl, or heteroalkyl, —(C$_1$–C$_{12}$) alkenyl, substituted alkenyl, or heteroalkenyl, —(C$_1$–C$_{12}$) alkynyl, substituted alkynyl, or heteroalkynyl, or —(C$_0$–C$_{12}$ alkylene or substituted alkylene)-(C$_6$–C$_{12}$ arylene or heteroarylene)-(C$_0$–C$_{12}$ alkyl or substituted alkyl);

n is 2;

Y is independently —CR$_6$R$_7$—; where R$_6$ and R$_7$ are each independenly hydrogen, R$_c$, —OH, —OR$_c$, —SH, —SR$_c$, —NH$_2$, —NHR$_c$, —NR$_c$R$_d$, —C(=O)R$_c$, —C(=O)NR$_c$R$_d$, —C(=O)SR$_c$, —C(=O)CR$_c$R$_d$R$_e$, —C(=O)OCR$_c$R$_d$R$_e$, —S(=O)$_2$NR$_c$R$_d$, —N(R$_c$)C(=O)R$_d$, —N(R$_c$)C(=O)OR$_d$, —N(R$_c$)S(=O)$_2$R$_d$, or —N(R$_c$)S(=O)$_2$OR$_d$, or where two vicinal R$_6$ or R$_7$ groups combine to form a substituted or unsubstituted C$_4$–C$_{10}$ cyclic alkyl, cyclic heteroalkyl, aryl or heteroaryl group; where R$_c$, R$_d$ and R$_e$ are each independently hydrogen, —(C$_1$–C$_{12}$) alkyl, substituted alkyl, or heteroalkyl, —(C$_1$–C$_{12}$) alkenyl, substituted alkenyl, or heteroalkenyl, —(C$_1$–C$_{12}$) alkynyl, substituted alkynyl, or heteroalkynyl, or —(C$_0$–C$_8$ alkylene or substituted alkylene)-(C$_6$–C$_{12}$ arylene or heteroarylene)-(C$_0$–C$_8$ alkyl or substituted alkyl), or where, when two or three of R$_c$, R$_d$ and R$_e$ are attached to the same atom, two or three of R$_c$, R$_d$ and R$_e$ can combine to form a substituted or unsubstituted —(C$_4$–C$_{10}$) cyclic alkyl, cyclic heteroalkyl, aryl or heteroaryl group; or a pharmaceutically acceptable salt thereof;

wherein heteroaryl refers to a substituent selected from the group consisting of imidazolyl, pyrazolyl, pyrazinyl, pyridazinyl, pyrimidinly, pyrrolyl, pyridyl, thiopene, indolyl, quinolinyl, quinazolinyl, benzimidazolyl, indolizinyl, and benzothienyl;

wherein cyclic heteroalkyl refers to a substituent selected from the group consisting of 1-ethyl-6-propylpiperidino, 2-ethylthiophenyl, piperazino, pyrrolidino, piperidino, and morpholino; and wherein each heteroaryl or cyclic heteroalkyl ring is optionally substituted on any atom within the ring with from one to three substituents independently selected from the group consisting of alkyl, alkenyl, alkynyl, benzyl, halogen, alkoxy, acyloxy, amino, mono or dialkylamino, hydroxyl, mercapto, carboxy, benzyloxy, phenyl, aryloxy, cyano, nitro, thioalkoxy, carboxaldehyde, carboalkoxy and carboxamide.

13. A compound of the Formula (Ib):

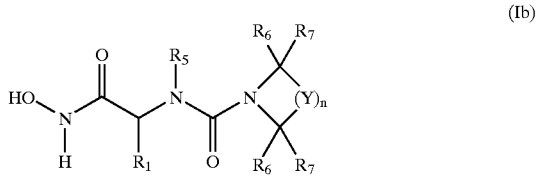

(Ib)

wherein:
R₁ is selected from the group consisting of hydrogen, $R_a$, —$R_b$—OH, and —$R_b$—O—$R_a$ where $R_a$ is selected from the group consisting of —($C_1$-$C_{12}$) alkyl, substituted alkyl, or heteroalkyl, —($C_1$-$C_{12}$) alkenyl, substituted alkenyl, or heteroalkenyl, —($C_1$-$C_{12}$) alkynyl, substituted alkynyl, or heteroalkynyl, or —($C_0$-$C_8$ alkyl or substituted alkyl)-($C_3$-$C_{12}$ aryl or heteroaryl)-($C_0$-$C_8$ alkyl or substituted alkyl); and $R_b$ is selected from the group consisting of —($C_1$-$C_{12}$) alkylene, substituted alkylene, or heteroalkylene, —($C_1$-$C_{12}$) alkenylene, substituted alkenylene, or heteroalkenylene, —($C_1$-$C_{12}$) alkynylene, substituted alkynylene, or heteroalkynylene, or —($C_0$-$C_8$ alkylene or substituted alkylene)-($C_6$-$C_{12}$ arylene or heteroarylene)-($C_0$-$C_8$ alkyl or substituted alkyl);

R₅ is selected from the group consisting of hydrogen, —($C_1$-$C_{12}$) alkyl, substituted alkyl, or heteroalkyl, —($C_1$-$C_{12}$) alkenyl, substituted alkenyl, or heteroalkenyl, —($C_1$-$C_{12}$) alkynyl, substituted alkynyl, or heteroalkynyl, or —($C_0$-$C_{12}$ alkyl or substituted alkyl)-($C_3$-$C_{12}$ aryl or heteroaryl)-($C_0$-$C_{12}$ alkyl or substituted alkyl); n is 2; Y is independently —$CR_6R_7$—; and $R_6$ and $R_7$ are each independently —H, —$R_h$, —OH, —$OR_h$, —SH, —$SR_h$, —$NH_2$, —$NHR_h$, —$NR_hR_i$, —C(=O)H, —C(=O)$OR_h$, —C(=O)$NH_2$, —C(=O)$NHR_h$, —C(=O)$NR_hR_i$, —C(=O)OH, —C(=O)SH, —C(=O)$SR_h$, —C(=O)$CH_3$, —C(=O)$CH_2R_h$, —C(=O)$CHR_hR_i$, —C(=O)$CR_hR_iR_j$, —C(=O)$OCH_3$, —C(=O)$OCH_2R_h$, —C(=O)$OCHR_hR_i$, —C(=O)$OCR_hR_iR_j$, —S(=O)$_2$$NH_2$, —S(=O)$_2$$NHR_h$, —S(=O)$_2$$NR_hR_i$, —NHC(=O)H, —N($R_h$)C(=O)H, —NHC(=O)$R_i$, —NHC(=O)$OR_i$, —N($R_h$)C(=O)$R_i$, —N($R_h$)C(=O)$OR_i$, —NHS(=O)$_2$H, —N($R_h$)S(=O)$_2$H, —NHS(=O)$_2$$OR_i$, —N($R_h$)S(=O)$_2$$OR_i$, —N(H)S(=O)$_2$$R_i$, or —N($R_h$)S(=O)$_2$$R_i$; where $R_h$, $R_i$ and $R_j$ are each independently —($C_1$-$C_{12}$) alkyl, substituted alkyl, or heteroalkyl, —($C_1$-$C_{12}$) alkenyl, substituted alkenyl, or heteroalkenyl, —($C_1$-$C_{12}$) alkynyl, substituted alkynyl, or heteroalkynyl, or ($C_0$-$C_8$ alkylene or substituted alkylene)-($C_6$-$C_{12}$ arylene or heteroarylene)-($C_0$-$C_8$ alkyl or substituted alkyl) or a pharmaceutically acceptable salt thereof;

wherein heteroaryl refers to a substituent selected from the group consisting of imidazolyl, pyrazolyl, pyrazinyl, pyridazinyl, pyriimidinly, pyrrolyl, pyridyl, thiopene, indolyl, quinolinyl, quinazolinyl, benzimidazolyl, indolizinyl, and benzothienyl;

wherein cyclic heteroalkyl refers to a substituent selected from the group consisting of 1-ethyl-6-propylpiperidino, 2-ethylthiophenyl, piperazino, pyrrolidino, piperidino, and morpholino; and wherein each heteroaryl or cyclic heteroalkyl ring is optionally substituted on any atom within the ring with from one to three substituents independently selected from the group consisting of alkyl, alkenyl, alkynyl, benzyl, halogen, alkoxy, acyloxy, amino, mono or dialkylamino, hydroxyl, mercapto, carboxy, benzyloxy, phenyl, aryloxy, cyano, nitro, thioalkoxy, carboxaldehyde, carboalkoxy and carboxamide.

14. A compound selected from the group consisting of:
N-hydroxy-2-[N-(3-methylbutyl)-N-(2-(S)-3-phenoxyphenylaminocarbonyl)-pyrrolidin-1-carbonyl)amino]acetamide;
N-hydroxy-2-[N-(2-cyclopentylethyl)-N-(2-(S)-2-methyl-1,3,4-thiadiazol-5-ylaminocarbonyl)pyrrolidin-1-carbonyl)amino]acetamide;
N-hydroxy-2-[N-(2-cyclopentylethyl)-N-(2-(S)-thiazol-2-ylaminocarbonyl)-pyrrolidin-1-carbonyl)amino]acetamide;
N-hydroxy-2-[N-(2-cyclopentylethyl)-N-(2-(S)-6-phenylimidazol-2-ylaminocarbonyl)-pyrrolidin-1-carbonyl)amino]acetamide;
N-hydroxy-2-[N-(2-cyclopentylethyl)-N-(2-(S)-pyrazin-2-ylaminocarbonyl)-pyrrolidin-1-carbonyl)amino]acetamide;
N-hydroxy-2-[N-(3-methylbutyl)-N-(2-(S)-3-methylbutylaminocarbonyl)-pyrrolidin-1-carbonyl)amino]acetamide;
N-hydroxy-2-[N-(2-cyclopentylethyl)-N-(2-(S)-imidazol-2-ylaminocarbonyl)-pyrrolidin-1-carbonyl)amino]acetamide;
N-hydroxy-2-[N-(2-cyclopentylethyl)-N-(2-(S)-4,5-dimethylthiazol-2-ylaminocarbonyl)-pyrrolidin-1-carbonyl)amino]acetamide; and
N-hydroxy-2-[N-(3-methylbutyl)-N-(2-(S)-4,5-dimethylthiazol-2-yl aminocarbonyl)-pyrrolidin-1-carbonyl)amino]acetamide or a pharmaceutically acceptable salt thereof.

15. A pharmaceutical composition comprising a therapeutically effective amount of a compound of any one of claims 1 to 14 and a pharmaceutically acceptable excipient.

16. A method of treating a prokaryotic microbial infection in a mammal which comprises administration to said mammal of a therapeutically effective amount of a compound of any one of claims 1 to 14.

17. The method of claim 16 wherein the microbial infection is a bacterial infection.

18. A pharmaceutical composition comprising:
(i) a therapeutically effective amount of a compound of Formula (Ic):

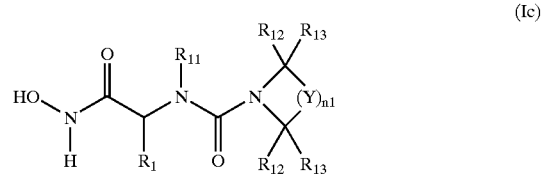

(Ic)

wherein:
R₁₀ is selected from the group consisting of hydrogen, $R_{14}$, $R_{15}$OH, and $R_{15}$—O—$R_{16}$, where $R_{14}$ and $R_{16}$ are independently selected from the group consisting of —($C_1$-$C_{12}$) alkyl, substituted alkyl, or heteroalkyl, —($C_1$-$C_{12}$) alkenyl, substituted alkenyl, or heteroalkenyl, —($C_1$-$C_{12}$) alkynyl, substituted alkynyl, or heteroalkynyl, or —($C_0$-$C_8$ alkylene or substituted alkylene)-($C_6$-$C_{12}$ arylene or heteroarylene)-($C_0$-$C_8$ alkyl or substituted alkyl); and $R_{15}$ is selected from the group consisting of —($C_1$-$C_{12}$) alkylene, substituted alkylene, or heteroalkylene, —($C_1$-$C_{12}$) alkenylene, substituted alkenylene, or heteroalkenylene, —($C_1$-$C_{12}$) alkynylene, substituted alkynylene, or heteroalkynylene, or —($C_0$-$C_8$ alkylene or substituted alkylene)-($C_6$-$C_{12}$arylene or heteroarylene)-($C_0$-$C_8$ alkylene or substituted alkylene);

$R_{11}$ is selected from the group consisting of hydrogen, —($C_1$-$C_{12}$) alkyl, substituted alkyl, or heteroalkyl, —($C_1$-$C_{12}$) alkenyl, substituted alkenyl, or heteroalkenyl, —($C_1$-$C_{12}$) alkynyl, substituted alkynyl, or heteroalkynyl, or —($C_0$-$C_{12}$ alkylene or substituted alkylene)-($C_6$-$C_{12}$ arylene or heteroarylene)-($C_0$-$C_{12}$ alkyl or substituted alkyl);

$n_1$ is 2;

Y is independently —$CR_{12}R_{13}$—; where $R_{12}$ and $R_{13}$ are each independently hydrogen, $R_{17}$, —OH, —$OR_{17}$, —SH, —$SR_{17}$, —$NH_2$, —$NHR_{17}$, —$NR_{17}R_{18}$, —C(=O)$R_{17}$, —C(=O)$NR_{17}R_{18}$, —C(=O)$OR_{17}$, —C(=O)$SR_{17}$, —C(=O)$CR_{17}R_{18}R_{19}$, —C(=O)$OCR_{17}R_{18}R_{19}$, —S(=O)$_2$$NR_{17}R_{18}$, —N($R_{17}$)C(=O)$R_{18}$, —N($R_{17}$)C(=O)$OR_{18}$, —N($R_{17}$)S(=O)$_2$$R_{18}$, or —N($R_{17}$)S(=O)$_2$$OR_{18}$, or —N($R_{17}$)S(=O)$_2$$OR_{18}$, or where two vicinal $R_{12}$ or $R_{13}$ groups combine to form a substituted or unsubstituted —($C_4$-$C_{10}$) cyclic alkyl, cyclic heteroalkyl, aryl or heteroaryl group; where $R_{17}$, $R_{18}$ and $R_{19}$ are each independently hydrogen, —($C_1$-$C_{12}$) alkyl, substituted alkyl, or heteroalkyl, —($C_1$-$C_{12}$) alkenyl, substituted alkyenyl, or heteroalkenyl, —($C_1$-$C_{12}$) alkynyl, substituted alkynyl, or heteroalkynyl, alkoxy, or —($C_0$-$C_8$ alkylene or substituted alkylene)-($C_6$-$C_{12}$ arylene or heteroarylene)-($C_0$-$C_8$ alkyl or substituted alkyl), or where, when two or three of $R_{17}$, $R_{18}$ and $R_{19}$ are attached to the same atom, two or three of $R_{17}$, $R_{18}$ and $R_{19}$ can combine to form a substituted or unsubstituted —($C_4$-$C_{10}$)cyclic alkyl, cyclic heteroalkyl, aryl or heteroaryl group; or a pharmaceutically acceptable salt thereof; and (ii) a pharmaceutically acceptable carrier;

wherein heteroaryl refers to a substituent selected from the group consisting of imidazolyl, pyrazolyl, pyrazinyl, pyridazinyl, pyrimidinyl, pyrrolyl, pyridyl, thiopene, indolyl, quinolinyl, quinazolinyl, benzimidazolyl, indolizinyl, and benzothienyl;

wherein cyclic heteroalkyl refers to a substituent selected from the group consisting of 1-ethyl-6-propylpiperidino, 2-ethylthiophenyl, piperazino, pyrrolidino, piperidino, and morpholino; and wherein each heteroaryl or cyclic heteroalkyl ring is optionally substituted on any atom within the ring with from one to three substituents independently selected from the group consisting of alkyl, alkenyl, alkynyl, benzyl, halogen, alkoxy, acyloxy, amino, mono or dialkylamino, hydroxyl, mercapto, carboxy, benzyloxy, phenyl, aryloxy, cyano, nitro, thioalkoxy, carboxaldehyde, carboalkoxy and carboxamide.

19. The pharmaceutical composition of claim 18, wherein the compound comprises $R_{10}$ which is hydrogen, alkyl, or —($C_1$-$C_{12}$) alkylene-OH.

20. The pharmaceutical composition of claim 18, wherein the compound comprises $R_{11}$ which is alkyl, substituted alkyl, alkenyl, heteroaralkyl, or heteroalkyl.

21. The pharmaceutical composition of claim 18 where the group:

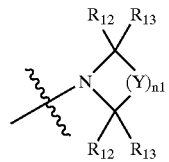

of the compound is a group of formula:

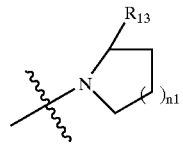

wherein:

n1 is 1; and $R_{13}$ is —C(=O)$NR_{17}R_{18}$, —N($R_{17}$)C(=O)$OR_{18}$ or —C(=O)$OR_{17}$ where $R_{17}$ and $R_{18}$ are each independently hydrogen, —($C_1$-$C_{12}$) alkyl, substituted alkyl, or heteroalkyl, —($C_1$-$C_{12}$) alkenyl, substituted alkenyl, or heteroalkenyl, —($C_1$-$C_{12}$) alkynyl, substituted alkynyl, or heteroalkynyl, or —($C_0$-$C_8$ alkylene or substituted alkylene)-($C_6$-$C_{12}$ arylene or heteroarylene)-($C_0$-$C_8$ alkyl or substituted alkyl), or when $R_{16}$ and $R_{17}$ are attached to the same atom, they can combine to form a substituted or unsubstituted —($C_4$-$C_{10}$)cyclic alkyl, cyclic heteroalkyl, aryl or heteroaryl group.

22. The pharmaceutical composition of claim 21, wherein the compound comprises $R_{13}$ which is 3-phenoxyphenylaminocarbonyl, phenylaminocarbonyl, 2-methyl-1,3,4-thiadiazol-5-ylaminocarbonyl, thiazol-2-ylaminocarbonyl, 6-phenylimidazol-2ylaminocarbonyl, pyrazin-2-ylaminocarbonyl, 3-methylbutylaminocarbonyl, imidazol-2-ylaminocarbonyl, 4,5-dimethylthiazol-2-ylaminocarbonyl, tert-butoxycarbonylamino, piperidin-1-ylcarbonyl, tert-butoxycarbonyl methylaminocarbonyl, or 4-benzylpiperazin-1-ylcarbonyl.

23. A pharmaceutical composition comprising:

(i) a therapeutically effective amount of a compound of Formula (Id):

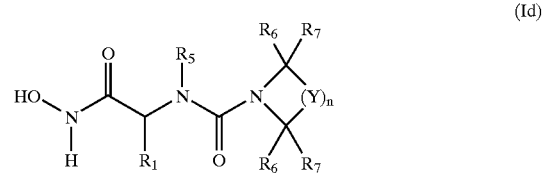

(Id)

wherein:

$R_1$ is selected from the group consisting of hydrogen, $R_s$, and —$R_1$—O—$R_s$ where $R_s$ is selected from the group consisting of —($C_1$-$C_{12}$) alkyl, —($C_1$-$C_{12}$) alkenyl, or —($C_1$-$C_{12}$) alkynyl; and $R_1$ is selected from the group consisting of —($C_1$-$C_{12}$) alkylene, —($C_1$-$C_{12}$) alkenylene, or —($C_1$-$C_{12}$) alkynylene;

$R_5$ is selected from the group consisting of hydrogen, —($C_1$-$C_{12}$) alkyl, substituted alkyl, or heteroalkyl, —($C_1$-$C_{12}$) alkenyl, substituted alkenyl, or heteroalkenyl, —($C_1$-$C_{12}$) alkynyl, substituted alkynyl, or heteroalkyl, or —($C_0$-$C_{12}$ alkylene or substituted alkylene)-($C_6$-$C_{12}$ arylene or heteroarylene)-($C_0$-$C_{12}$ alkyl or substituted alkyl);

n is 2;

Y is independently —$CR_6R_7$—; and where $R_6$ and $R_7$ are each independently hydrogen, $R_c$, —OH, —$OR_c$, —SH, —$SR_c$, —$NH_2$, —$NHR_c$, —$NR_cR_d$, —$C(=O)R_c$, —$C(=O)NR_cR_d$, —$C(=O)OR_c$, —$C(=O)SR_c$, —$C(=O)CR_cR_dR_e$, —$C(=O)OCR_cR_dR_e$, —$S(=O)_2NR_cR_d$, —$N(R_c)C(=O)R_d$, —$N(R_c)C(=O)OR_d$, —$N(R_c)S(=O)_2R_d$, or —$N(R_c)S(=O)_2OR_d$, or where two vicinal $R_6$ or $R_7$ groups combine to form a substituted or unsubstituted $C_4$–$C_{10}$ cyclic alkyl, cyclic heteroalkyl, aryl, or heteroaryl group; where $R_c$, $R_d$ and $R_e$ are each independently hydrogen, —($C_1$–$C_{12}$) alkyl, substituted alkyl, or heteroalkyl, —($C_1$–$C_{12}$) alkenyl, substituted alkyenyl, or heteroalkenyl, —($C_1$–$C_{12}$) alkynyl, substituted alkynyl, or heteroalkynyl, or —($C_0$–$C_8$) alkylene or substituted alkylene)-($C_6$–$C_{12}$ arylene or heteroarylene)-($C_0$–$C_8$ alkyl or substituted alkyl), or where, when two or three of $R_c$, $R_d$ and $R_e$ are attached to the same atom, two or three of $R_c$, $R_d$ and $R_e$ can combine to form a substituted or unsubstituted —($C_4$–$C_{10}$) cyclic alkyl, cyclic heteroalkyl, aryl or heteroaryl group; or a pharmaceutically acceptable salt thereof; and (ii) a pharmaceutically acceptable carrier;

wherein heteroaryl refers to a substituent selected from the group consisting of imidazolyl, pyrazolyl, pyrazinyl, pyridazinyl, pyrimidinyl, pyrrolyl, pyridyl, thiophene, indolyl, quinolinyl, quinazolinyl, benzimidazolyl, indolizinyl, and benzothienyl;

wherein cyclic heteroalkyl refers to a substituent selected from the group consisting of 1-ethyl-6-propylpiperidino, 2-ethylthiophenyl, piperazino, pyrrolidino, piperidino, and morpholino; and wherein each heteroaryl or cyclic heteroalkyl ring is optionally substituted on any atom within the ring with from one to three substituents independently selected from the group consisting of alkyl, alkenyl, alkynyl, benzyl, halogen, alkoxy, acyloxy, amino, mono or dialkylamino, hydroxyl, mercapto, carboxy, benzyloxy, phenyl, aryloxy, cyano, nitro, thioalkoxy, carboxaldehyde, carboalkoxy and carboxamide.

24. A pharmaceutical composition comprising:

a therapeutically effective amount of a compound of Formula (Ic):

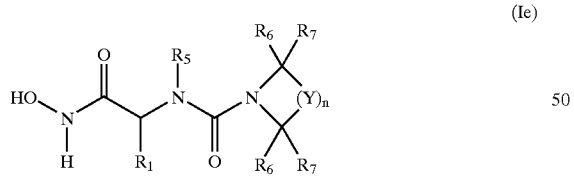

(Ie)

wherein:

$R_1$ is selected from the group consisting of hydrogen, $R_a$, —$R_b$—OH, and —$R_b$—O—$R_a$ where $R_a$ is selected from the group consisting of —($C_1$–$C_{12}$) alkyl, substituted alkyl, or heteroalkyl, —($C_1$–$C_{12}$) alkenyl, substituted alkenyl, or heteroalkenyl, —($C_1$–$C_{12}$) alkynyl, substituted alkynyl, or heteroalkynyl, or —($C_0$–$C_8$ alkyl or substituted alkyl)-($C_3$–$C_{12}$ aryl or heteroaryl)-($C_0$–$C_8$ alkyl or substituted alkyl); and $R_b$ is selected from the group consisting of —($C_1$–$C_{12}$) alkylene, substituted alkylene, or heteroalkylene, —($C_1$–$C_{12}$) alkenylene, substituted alkenylene, or heteroalkenylene, —($C_1$–$C_{12}$) alkynylene, substituted alkynylene, or heteroalkynylene, or —($C_0$–$C_8$ alkylene or substituted alkylene)-($C_6$–$C_{12}$ arylene or heteroarylene)-($C_0$–$C_8$ alkyl or substituted alkyl);

$R_5$ is selected from the group consisting of hydrogen, —($C_1$–$C_{12}$) alkyl, substituted alkyl, or heteroalkyl, –($C_1$–$C_{12}$) alkenyl, substituted alkenyl, or heteroalkenyl, —($C_1$–$C_{12}$) alkynyl, substituted alkynyl, or heteroalkynyl, or —($C_0$–$C_{12}$ alkyl or substituted alkyl)-($C_3$–$C_{12}$ aryl or heteroaryl)-($C_0$–$C_{12}$ alkyl or substituted alkyl);

n is 2;

Y is independently —$CR_6R_7$—; and $R_6$ and $R_7$ are each independently —H, —$R_h$, —OH, —$OR_h$, —SH, —$SR_h$, —$NH_2$, —$NHR_h$, —$NR_hR_i$, —$C(=O)H$, —$C(=O)R_h$, —$C(=O)NH_2$, —$C(=O)NHR_h$, —$C(=O)NR_hR_i$, —$C(=O)OH$, —$C(=O)OR_h$, —$C(=O)SH$, —$C(=O)SR_h$, —$C(=O)CH_3$, —$C(=O)CH_2R_h$, —$C(=O)CHR_hR_i$, —$C(=O)CR_hR_iR_j$, —$C(=O)OCH_3$, —$C(=O)OCH_2R_h$, —$C(=O)OCHR_hR_i$, —$C(=O)OCR_hR_iR_j$, —$S(=O)_2NH_2$, —$S(=O)_2NHR_h$, —$S(=O)_2NR_hR_i$, —$NHC(=O)H$, —$N(R_h)C(=O)H$, —$NHC(=O)R_i$, —$NHC(=O)OR_i$, —$N(R_h)C(=O)R_i$, —$N(R_h)C(=O)OR_i$, —$NHS(=O)_2H$, —$N(R_h)S(=O)_2H$, —$NHS(=O)_2OR_i$, —$N(R_h)S(=O)_2OR_i$, —$N(H)S(=O)_2R_i$ or —$N(R_h)S(=O)_2R_i$; where $R_h$, $R_i$ and $R_j$ are each independently —($C_1$–$C_{12}$) alkyl, substituted alkyl, or heteroalkyl, —($C$–$C_{12}$) alkenyl, substituted alkenyl, or heteroalkenyl, —($C_1$–$C_{12}$) alkynyl, substituted alkynyl, or heteroalkynyl, or ($C_0$–$_8$) alkylene or substituted alkylene)-($C_6$–$C_{12}$ arylene or heteroarylene)-($C_0$–$C_8$ alkyl or substituted alkyl) or a pharmaceutically acceptable salt thereof; and (ii) a pharmaceutically acceptable carrier;

wherein heteroaryl refers to a substituent selected from the group consisting of imidazolyl, pyrazolyl, pyrazinyl, pyridiazinyl, pyrimidinyl, pyrrolyl, pyridyl, thiopene, indolyl, quinolinyl, quinazolinyl, benzimidazolyl, indolizinyl, and benzothienyl;

wherein cyclic heteroalkyl refers to a substituent selected from the group consisting of 1-ethyl-6-propylpiperidino, 2-ethylthiophenyl, piperazino, pyrrolidino, piperidino, and morpholino; and wherein each heteroaryl or cyclic heteroalkyl ring is optionally substituted on any atom within the ring from one to three substituents independently selected from the group consisting of alkyl, alkenyl, alkynyl, benzyl, halogen, alkoxy, acyloxy, amino, mono or dialkylamino, hydroxyl, mercapto, carboxy, benzyloxy, phenyl, aryloxy, cyano, nitro, thioalkoxy, carboxaldehyde, carboalkoxy and carboxamide.

25. A method of treating a prokaryotic microbial infection in a mammal which comprises administration to said mammal of an effective amount of the pharmaceutical composition of claim 18.

26. The method of claim 25 wherein the prokaryotic microbial infection is a bacterial infection.

* * * * *